(12) United States Patent
Ackerman et al.

(10) Patent No.: US 11,400,164 B2
(45) Date of Patent: Aug. 2, 2022

(54) IMMUNOCONJUGATES TARGETING HER2

(71) Applicants: Bolt Biotherapeutics, Inc., Redwood City, CA (US); The Board of Trustees of The Leland Stanford Junior University, Stanford, CA (US)

(72) Inventors: Shelley Erin Ackerman, Redwood City, CA (US); Michael N. Alonso, Redwood City, CA (US); David Y. Jackson, Redwood City, CA (US); Arthur Lee, Redwood City, CA (US); Edgar George Engleman, Atherton, CA (US)

(73) Assignees: Bolt Biotherapeutics, Inc., Redwood City, CA (US); The Board of Trustees of The Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/465,284

(22) Filed: Sep. 2, 2021

(65) Prior Publication Data
US 2022/0001022 A1    Jan. 6, 2022

Related U.S. Application Data

(63) Continuation of application No. PCT/US2020/022645, filed on Mar. 13, 2020.

(60) Provisional application No. 62/819,356, filed on Mar. 15, 2019.

(51) Int. Cl.
*A61K 47/68*     (2017.01)
*A61K 39/395*    (2006.01)
*A61P 35/00*     (2006.01)

(52) U.S. Cl.
CPC ........ *A61K 47/6835* (2017.08); *A61K 39/395* (2013.01); *A61K 47/6801* (2017.08); *A61K 47/6803* (2017.08); *A61K 47/6849* (2017.08); *A61K 47/6851* (2017.08); *A61K 47/6855* (2017.08); *A61K 47/6863* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 4,459,296 A | 7/1984 | Ancher et al. |
| 4,689,338 A | 8/1987 | Gerster |
| 6,069,149 A | 5/2000 | Nanba et al. |
| 6,331,539 B1 | 12/2001 | Crooks et al. |
| 6,451,810 B1 | 9/2002 | Coleman et al. |
| 6,541,485 B1 | 4/2003 | Crooks et al. |
| 6,573,273 B1 | 6/2003 | Crooks et al. |
| 6,677,349 B1 | 1/2004 | Griesgraber |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,888,000 B2 | 5/2005 | Crooks et al. |
| 6,897,221 B2 | 5/2005 | Crooks et al. |
| 6,924,293 B2 | 8/2005 | Lindstrum |
| 7,030,131 B2 | 4/2006 | Crooks et al. |
| 7,112,677 B2 | 9/2006 | Griesgraber |
| 7,157,453 B2 | 1/2007 | Crooks et al. |
| 7,199,131 B2 | 4/2007 | Lindstrom |
| 7,375,180 B2 | 5/2008 | Gorden et al. |
| 7,393,859 B2 | 7/2008 | Coleman et al. |
| 7,427,629 B2 | 9/2008 | Kedl et al. |
| 7,700,321 B2 | 4/2010 | McPherson et al. |
| 7,799,800 B2 | 9/2010 | Wightman |
| 7,923,560 B2 | 4/2011 | Wightman et al. |
| 7,943,609 B2 | 5/2011 | Griesgraber et al. |
| 8,017,779 B2 | 9/2011 | Merrill et al. |
| 8,071,336 B2 | 12/2011 | McPherson et al. |

(Continued)

FOREIGN PATENT DOCUMENTS

| | | |
|---|---|---|
| CN | 103328005 A | 9/2013 |
| EA | 201891040 A1 | 10/2018 |

(Continued)

OTHER PUBLICATIONS

Carter et al., "Induction of CD8+ T cell responses through targeting of antigen to Dectin-2," *Cell Immunol.*, 239(2): 87-91 (2006).

(Continued)

*Primary Examiner* — Daniel C Gamett
(74) *Attorney, Agent, or Firm* — Leydig, Voit & Mayer, Ltd.

(57) ABSTRACT

The invention provides an immunoconjugate of formula:

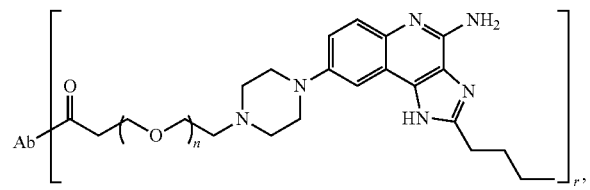

or pharmaceutically acceptable salt thereof, wherein subscript r is an integer from 1 to 10, subscript n is an integer from about 2 to about 25, and "Ab" is an antibody construct that has an antigen binding domain that binds HER2. The invention further provides compositions comprising and methods of treating cancer with the immunoconjugate.

44 Claims, 9 Drawing Sheets
Specification includes a Sequence Listing.

(56) References Cited

U.S. PATENT DOCUMENTS

| | | |
|---|---|---|
| 8,124,085 B2 | 2/2012 | Nielsen et al. |
| 8,198,020 B2 | 6/2012 | Francois et al. |
| 8,207,162 B2 | 6/2012 | Griesgraber et al. |
| 8,277,810 B2 | 10/2012 | Long et al. |
| 8,435,800 B2 | 5/2013 | Gengrinovitch |
| 8,440,192 B2 | 5/2013 | Nielsen et al. |
| 8,470,980 B2 | 6/2013 | Hutchinson et al. |
| 8,481,029 B2 | 6/2013 | Glennie et al. |
| 8,518,405 B2 | 8/2013 | Mukherjee |
| 8,524,702 B2 | 9/2013 | Howbert et al. |
| 8,546,383 B2 | 10/2013 | Griesgraber et al. |
| 8,574,575 B2 | 11/2013 | Govindan et al. |
| 8,637,032 B2 | 1/2014 | Long et al. |
| 8,658,666 B2 | 2/2014 | Rice et al. |
| 8,691,809 B2 | 4/2014 | Howbert et al. |
| 8,709,418 B2 | 4/2014 | Okano et al. |
| 8,728,486 B2 | 5/2014 | David et al. |
| 8,741,291 B2 | 6/2014 | Bhat et al. |
| 8,758,752 B2 | 6/2014 | Govindan et al. |
| 8,828,398 B2 | 9/2014 | Kobayashi et al. |
| 8,841,417 B2 | 9/2014 | Wu et al. |
| 8,871,908 B2 | 10/2014 | Liu et al. |
| 8,911,740 B2 | 12/2014 | Saito et al. |
| 8,937,160 B2 | 1/2015 | Kobayashi et al. |
| 8,951,528 B2 | 2/2015 | Stoermer et al. |
| 8,993,524 B2 | 3/2015 | Bedi et al. |
| 9,115,200 B2 | 8/2015 | Okano et al. |
| 9,126,940 B2 | 9/2015 | Howbert et al. |
| 9,169,325 B2 | 10/2015 | Keler et al. |
| 9,175,074 B2 | 11/2015 | Okano et al. |
| 9,180,188 B2 | 11/2015 | Kobayashi et al. |
| 9,181,334 B2 | 11/2015 | Kobayashi et al. |
| 9,181,348 B2 | 11/2015 | Kobayashi et al. |
| 9,192,667 B2 | 11/2015 | Hoves et al. |
| 9,205,148 B2 | 12/2015 | Langermann et al. |
| 9,242,964 B2 | 1/2016 | Howbert et al. |
| 9,243,069 B2 | 1/2016 | Johnson et al. |
| 9,248,127 B2 | 2/2016 | Perman et al. |
| 9,260,513 B2 | 2/2016 | Kobayashi et al. |
| 9,266,958 B2 | 2/2016 | Kobayashi et al. |
| 9,273,128 B2 | 3/2016 | Okano et al. |
| 9,273,130 B2 | 3/2016 | Kobayashi et al. |
| 9,308,253 B2 | 4/2016 | Kim et al. |
| 9,314,521 B2 | 4/2016 | Ossendorp et al. |
| 9,358,307 B2 | 6/2016 | Pitcovski et al. |
| 9,364,554 B2 | 6/2016 | Hutchinson et al. |
| 9,382,329 B2 | 7/2016 | Chang et al. |
| 9,409,993 B2 | 8/2016 | Minamida et al. |
| 9,416,191 B2 | 8/2016 | Kobayashi et al. |
| 9,416,192 B2 | 8/2016 | Okano et al. |
| 9,416,193 B2 | 8/2016 | Saito et al. |
| 9,428,581 B2 | 8/2016 | Saito et al. |
| 9,441,005 B2 | 9/2016 | David et al. |
| 9,441,044 B2 | 9/2016 | Bedi et al. |
| 9,475,804 B2 | 10/2016 | Wightman |
| 9,498,541 B2 | 11/2016 | Chari et al. |
| 9,522,958 B2 | 12/2016 | Epstein et al. |
| 9,556,167 B2 | 1/2017 | Spiegel et al. |
| 9,573,993 B2 | 2/2017 | Okano et al. |
| 9,617,336 B2 | 4/2017 | Cojocaru et al. |
| 9,623,118 B2 | 4/2017 | Chang et al. |
| 9,655,904 B2 | 5/2017 | Howbert et al. |
| 9,670,286 B2 | 6/2017 | Chang et al. |
| 9,676,849 B2 | 6/2017 | Farrington et al. |
| 9,676,854 B2 | 6/2017 | Liu et al. |
| 9,724,426 B2 | 8/2017 | Graversen et al. |
| 9,751,945 B2 | 9/2017 | Ploegh et al. |
| 9,770,506 B2 | 9/2017 | Ossendorp et al. |
| 9,797,907 B2 | 10/2017 | Goldenberg et al. |
| 9,827,329 B2 | 11/2017 | Li |
| 9,833,511 B2 | 12/2017 | Govindan et al. |
| 9,849,176 B2 | 12/2017 | Govindan et al. |
| 9,878,052 B2 | 1/2018 | Li |
| 9,902,724 B2 | 2/2018 | Wightman |
| 9,926,374 B2 | 3/2018 | Glennie et al. |
| 9,926,380 B2 | 3/2018 | Molldrem et al. |
| 9,999,668 B2 | 6/2018 | Govindan et al. |
| 10,000,539 B2 | 6/2018 | Mahr et al. |
| 10,005,772 B2 | 6/2018 | Stoermer et al. |
| 10,016,412 B2 | 7/2018 | Spiegel et al. |
| 10,105,426 B2 | 10/2018 | Noelle et al. |
| 10,131,713 B2 | 11/2018 | Johnson et al. |
| 10,188,741 B2 | 1/2019 | Pitcovski et al. |
| 10,208,037 B2 | 2/2019 | David et al. |
| 10,227,417 B2 | 3/2019 | Agatsuma et al. |
| 10,328,158 B2 | 6/2019 | Li |
| 10,428,045 B2 | 10/2019 | Coburn et al. |
| 10,434,183 B2 | 10/2019 | Georges |
| 10,457,681 B2 | 10/2019 | Young et al. |
| 10,472,361 B2 | 11/2019 | Poudel et al. |
| 10,472,420 B2 | 11/2019 | Stoermer et al. |
| 10,487,084 B2 | 11/2019 | He et al. |
| 10,494,370 B2 | 12/2019 | Poudel et al. |
| 10,508,115 B2 | 12/2019 | He et al. |
| 10,519,131 B2 | 12/2019 | Coburn et al. |
| 10,533,007 B2 | 1/2020 | Glick et al. |
| 10,548,985 B2 | 2/2020 | Li |
| 10,548,988 B2 | 2/2020 | Li |
| 10,556,903 B2 | 2/2020 | Glick et al. |
| 10,640,499 B2 | 5/2020 | Chin et al. |
| 10,660,971 B2 | 5/2020 | Li |
| 10,662,252 B2 | 5/2020 | Chang et al. |
| 10,675,358 B2 | 6/2020 | Alonso et al. |
| 10,682,365 B2 | 6/2020 | Krieg |
| 10,722,591 B2 | 7/2020 | Coffman et al. |
| 10,744,204 B2 | 8/2020 | Gao et al. |
| 10,744,206 B2 | 8/2020 | Li |
| 10,780,180 B2 | 9/2020 | Li |
| 10,849,984 B2 | 12/2020 | Georges |
| 10,953,073 B2 | 3/2021 | Schellenberger et al. |
| 10,973,826 B2 | 4/2021 | Cortez et al. |
| 11,046,781 B2 | 6/2021 | Li |
| 11,053,240 B2 | 7/2021 | Li et al. |
| 11,110,178 B2 | 9/2021 | Alonso et al. |
| 11,130,812 B2 | 9/2021 | Li et al. |
| 11,136,397 B2 | 10/2021 | Li |
| 2002/0146388 A1 | 10/2002 | Gillies |
| 2002/0155108 A1 | 10/2002 | Barbera-Guillem |
| 2003/0144283 A1 | 7/2003 | Coleman et al. |
| 2004/0038294 A1 | 2/2004 | Evangelista et al. |
| 2004/0091491 A1 | 5/2004 | Kedl et al. |
| 2004/0131587 A1 | 7/2004 | Thomas et al. |
| 2004/0171086 A1 | 9/2004 | Fink et al. |
| 2004/0191833 A1 | 9/2004 | Fink et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0113297 A1 | 5/2005 | Francois et al. |
| 2005/0158325 A1 | 7/2005 | Hammerbeck et al. |
| 2006/0018911 A1 | 1/2006 | Ault-Riche et al. |
| 2006/0142202 A1 | 6/2006 | Alkan et al. |
| 2007/0092521 A1 | 4/2007 | McPherson et al. |
| 2007/0166384 A1 | 7/2007 | Zarraga |
| 2008/0031887 A1 | 2/2008 | Lustgarten |
| 2008/0031900 A1 | 2/2008 | Palucka et al. |
| 2008/0233140 A1 | 9/2008 | Banchereau et al. |
| 2008/0254047 A1 | 10/2008 | Banchereau et al. |
| 2009/0004192 A1 | 1/2009 | Pedersen et al. |
| 2009/0004194 A1 | 1/2009 | Kedl |
| 2009/0035323 A1 | 2/2009 | Stoermer et al. |
| 2009/0123467 A1 | 5/2009 | Bedi et al. |
| 2009/0155289 A1 | 6/2009 | Roberts et al. |
| 2009/0181022 A1 | 7/2009 | Nielsen et al. |
| 2009/0325315 A1 | 12/2009 | Hirai et al. |
| 2010/0004156 A1 | 1/2010 | Kaushal et al. |
| 2010/0129383 A1 | 5/2010 | Suresh et al. |
| 2010/0158928 A1 | 6/2010 | Stoermer et al. |
| 2010/0291109 A1 | 11/2010 | Kedl |
| 2010/0317111 A1 | 12/2010 | Kedl et al. |
| 2011/0064752 A1 | 3/2011 | Hutchinson et al. |
| 2011/0182847 A1 | 7/2011 | Noelle et al. |
| 2011/0274653 A1 | 11/2011 | Banchereau et al. |
| 2011/0274685 A1 | 11/2011 | Keler et al. |

(56) References Cited

U.S. PATENT DOCUMENTS

| | | |
|---|---|---|
| 2011/0274692 A1 | 11/2011 | White et al. |
| 2012/0034213 A1 | 2/2012 | Hellmann |
| 2012/0039916 A1 | 2/2012 | Zurawski et al. |
| 2012/0045414 A1 | 2/2012 | Delucia |
| 2012/0064593 A1 | 3/2012 | Kohler et al. |
| 2012/0177652 A1 | 7/2012 | Nielsen et al. |
| 2012/0213771 A1 | 8/2012 | Keler et al. |
| 2012/0219615 A1 | 8/2012 | Hershberg et al. |
| 2012/0231023 A1 | 9/2012 | Zurawski et al. |
| 2012/0237518 A1 | 9/2012 | Yamaguchi et al. |
| 2012/0301465 A1 | 11/2012 | Dutartre et al. |
| 2012/0328605 A1 | 12/2012 | Larocque et al. |
| 2013/0039911 A1 | 2/2013 | Bedi et al. |
| 2013/0165455 A1 | 6/2013 | Carson et al. |
| 2013/0183311 A1 | 7/2013 | Nielsen et al. |
| 2013/0195794 A1 | 8/2013 | Heath et al. |
| 2013/0202596 A1 | 8/2013 | Salas et al. |
| 2013/0330350 A1 | 12/2013 | Dimasi |
| 2013/0336994 A1 | 12/2013 | Hutchinson et al. |
| 2014/0065096 A1 | 3/2014 | Ichim et al. |
| 2014/0179558 A1 | 6/2014 | Ido et al. |
| 2014/0199293 A1 | 7/2014 | Sabbadini et al. |
| 2014/0199763 A1 | 7/2014 | Dutartre et al. |
| 2014/0205602 A1 | 7/2014 | Long et al. |
| 2014/0294849 A1 | 10/2014 | Larocque et al. |
| 2014/0341978 A1 | 11/2014 | Kim et al. |
| 2014/0363461 A1 | 12/2014 | Bagnoli et al. |
| 2015/0044279 A1 | 2/2015 | Miller et al. |
| 2015/0071948 A1 | 3/2015 | Lazar et al. |
| 2015/0110742 A1 | 4/2015 | Spiegel et al. |
| 2015/0141625 A1 | 5/2015 | Stoermer et al. |
| 2015/0158947 A1 | 6/2015 | Cojocaru et al. |
| 2015/0174268 A1 | 6/2015 | Li |
| 2015/0183881 A1 | 7/2015 | Bedi et al. |
| 2015/0191546 A1 | 7/2015 | Molldrem et al. |
| 2015/0284416 A1 | 10/2015 | Zhao |
| 2015/0299194 A1 | 10/2015 | Hoves et al. |
| 2015/0322155 A1 | 11/2015 | Zhao |
| 2016/0008485 A1 | 1/2016 | Marquette et al. |
| 2016/0015803 A1 | 1/2016 | Kedl |
| 2016/0015821 A1 | 1/2016 | Hubbell et al. |
| 2016/0067351 A1 | 3/2016 | Geierstanger et al. |
| 2016/0068533 A1 | 3/2016 | Ferguson et al. |
| 2016/0108123 A1 | 4/2016 | Freeman et al. |
| 2016/0112466 A1 | 4/2016 | Gunnalan et al. |
| 2016/0130348 A1 | 5/2016 | Langermann et al. |
| 2016/0137608 A1 | 5/2016 | Howbert et al. |
| 2016/0145350 A1 | 5/2016 | Lonberg et al. |
| 2016/0159901 A1 | 6/2016 | Sahin et al. |
| 2016/0194399 A1 | 7/2016 | Irving et al. |
| 2016/0206754 A1 | 7/2016 | Chang et al. |
| 2016/0208020 A1 | 7/2016 | Chang et al. |
| 2016/0208021 A1 | 7/2016 | Chang et al. |
| 2016/0215056 A1 | 7/2016 | Glennie et al. |
| 2016/0279248 A1 | 9/2016 | Hutchinson et al. |
| 2016/0297889 A1 | 10/2016 | Okano et al. |
| 2016/0311903 A1 | 10/2016 | West et al. |
| 2016/0324981 A1 | 11/2016 | Pinkerton et al. |
| 2016/0324983 A1 | 11/2016 | Li |
| 2016/0339109 A1 | 11/2016 | Chang et al. |
| 2016/0339110 A1 | 11/2016 | Chang et al. |
| 2016/0339111 A1 | 11/2016 | Chang et al. |
| 2016/0339115 A1 | 11/2016 | Chang et al. |
| 2016/0339116 A1 | 11/2016 | Chang et al. |
| 2016/0340427 A1 | 11/2016 | Chang et al. |
| 2016/0340430 A1 | 11/2016 | Bedi et al. |
| 2016/0340435 A1 | 11/2016 | Chang et al. |
| 2016/0340439 A1 | 11/2016 | Engleman et al. |
| 2016/0347849 A1 | 12/2016 | Cai et al. |
| 2016/0355587 A1 | 12/2016 | West et al. |
| 2016/0355592 A1 | 12/2016 | Sagert et al. |
| 2016/0355599 A1 | 12/2016 | Sagert et al. |
| 2016/0375148 A1 | 12/2016 | Li |
| 2017/0008971 A1 | 1/2017 | Dennis et al. |
| 2017/0021033 A1 | 1/2017 | Geierstanger et al. |
| 2017/0028079 A1 | 2/2017 | Li |
| 2017/0044259 A1 | 2/2017 | Tipton et al. |
| 2017/0056391 A1 | 3/2017 | Li |
| 2017/0056518 A1 | 3/2017 | Chang et al. |
| 2017/0056519 A1 | 3/2017 | Chang et al. |
| 2017/0073343 A1 | 3/2017 | Galatsis et al. |
| 2017/0073415 A1 | 3/2017 | Urech et al. |
| 2017/0081416 A1 | 3/2017 | Long et al. |
| 2017/0087148 A1 | 3/2017 | Spiegel et al. |
| 2017/0095573 A1 | 4/2017 | Oh et al. |
| 2017/0114137 A1 | 4/2017 | Li |
| 2017/0119790 A1 | 5/2017 | Graversen et al. |
| 2017/0121421 A1 | 5/2017 | Cortez et al. |
| 2017/0145104 A1 | 5/2017 | Wang et al. |
| 2017/0152323 A1 | 6/2017 | Chang et al. |
| 2017/0158770 A1 | 6/2017 | Bedi et al. |
| 2017/0158772 A1 | 6/2017 | Thompson et al. |
| 2017/0173164 A1 | 6/2017 | Wightman |
| 2017/0183408 A1 | 6/2017 | Dimasi |
| 2017/0209574 A1 | 7/2017 | Cao et al. |
| 2017/0216452 A1 | 8/2017 | Ma et al. |
| 2017/0233745 A1 | 8/2017 | Dankers et al. |
| 2017/0290923 A1 | 10/2017 | Li et al. |
| 2017/0298139 A1 | 10/2017 | Thompson et al. |
| 2017/0306038 A1 | 10/2017 | Brogdon et al. |
| 2017/0319712 A1 | 11/2017 | Miller et al. |
| 2017/0368169 A1 | 12/2017 | Loew et al. |
| 2018/0037581 A1 | 2/2018 | McDonald et al. |
| 2018/0044429 A1 | 2/2018 | Keler et al. |
| 2018/0066053 A1 | 3/2018 | Keler et al. |
| 2018/0110874 A1 | 4/2018 | Li |
| 2018/0177887 A1 | 6/2018 | Li |
| 2018/0177888 A1 | 6/2018 | Li |
| 2018/0186792 A1 | 7/2018 | Wightman |
| 2018/0207273 A1 | 7/2018 | Dranoff et al. |
| 2018/0221503 A1 | 8/2018 | Kadiyala et al. |
| 2018/0222982 A1 | 8/2018 | Dranoff et al. |
| 2018/0251557 A1 | 9/2018 | Chui et al. |
| 2018/0258048 A1 | 9/2018 | Coburn et al. |
| 2018/0264133 A1 | 9/2018 | Chang et al. |
| 2018/0273948 A1 | 9/2018 | Kadiyala et al. |
| 2018/0296685 A1 | 10/2018 | Wooster et al. |
| 2018/0303845 A1 | 10/2018 | Dietsch |
| 2018/0303936 A1 | 10/2018 | Cheung et al. |
| 2018/0305357 A1 | 10/2018 | Stoermer et al. |
| 2018/0346572 A1 | 12/2018 | Li |
| 2019/0002583 A1 | 1/2019 | Li |
| 2019/0010236 A1 | 1/2019 | Kenkel et al. |
| 2019/0015516 A1 | 1/2019 | Jackson et al. |
| 2019/0016808 A1 | 1/2019 | Li |
| 2019/0016819 A1 | 1/2019 | Li |
| 2019/0030182 A1 | 1/2019 | Riggs-Sauthier et al. |
| 2019/0048084 A1 | 2/2019 | Li |
| 2019/0055243 A1 | 2/2019 | Poudel et al. |
| 2019/0055244 A1 | 2/2019 | Young et al. |
| 2019/0055245 A1 | 2/2019 | Poudel et al. |
| 2019/0055246 A1 | 2/2019 | He et al. |
| 2019/0055247 A1 | 2/2019 | He et al. |
| 2019/0062306 A1 | 2/2019 | Coburn et al. |
| 2019/0099415 A1 | 4/2019 | Li |
| 2019/0127367 A1 | 5/2019 | Glick et al. |
| 2019/0151462 A1 | 5/2019 | Coffman et al. |
| 2019/0169164 A1 | 6/2019 | Coburn et al. |
| 2019/0169165 A1 | 6/2019 | Coburn et al. |
| 2019/0202925 A1 | 6/2019 | Thompson |
| 2019/0201334 A1 | 7/2019 | Hakim et al. |
| 2019/0269789 A1 | 9/2019 | Li |
| 2019/0269790 A1 | 9/2019 | Li |
| 2019/0336615 A1 | 11/2019 | Thompson et al. |
| 2019/0352468 A1 | 11/2019 | Andrianov et al. |
| 2019/0374650 A1 | 12/2019 | Moon et al. |
| 2019/0381126 A1 | 12/2019 | Hu et al. |
| 2020/0009262 A1 | 1/2020 | White et al. |
| 2020/0016267 A1 | 1/2020 | Rinaldi et al. |
| 2020/0017501 A1 | 1/2020 | Young et al. |
| 2020/0024279 A1 | 1/2020 | Poudel et al. |
| 2020/0030442 A1 | 1/2020 | Cao |
| 2020/0031798 A1 | 1/2020 | Coburn et al. |
| 2020/0031936 A1 | 1/2020 | Hegde et al. |

(56) References Cited

U.S. PATENT DOCUMENTS

| | | |
|---|---|---|
| 2020/0038403 A1 | 2/2020 | Poudel et al. |
| 2020/0038519 A1 | 2/2020 | Georges |
| 2020/0039986 A1 | 2/2020 | Poudel et al. |
| 2020/0048254 A1 | 2/2020 | He et al. |
| 2020/0048255 A1 | 2/2020 | Poudel et al. |
| 2020/0048371 A1 | 2/2020 | Mills et al. |
| 2020/0054762 A1 | 2/2020 | Okano et al. |
| 2020/0055851 A1 | 2/2020 | Li et al. |
| 2020/0069814 A1 | 3/2020 | Zhao et al. |
| 2020/0079860 A1 | 3/2020 | Khalil et al. |
| 2020/0095248 A1 | 3/2020 | He et al. |
| 2020/0108139 A1 | 4/2020 | Levy et al. |
| 2020/0108151 A1 | 4/2020 | Jackson et al. |
| 2020/0113912 A1 | 4/2020 | Odegard et al. |
| 2020/0140547 A1 | 5/2020 | Bedi et al. |
| 2020/0140556 A1 | 5/2020 | Kenkel et al. |
| 2020/0155700 A1 | 5/2020 | Li |
| 2020/0164084 A1 | 5/2020 | Cortez et al. |
| 2020/0179527 A1 | 6/2020 | Li |
| 2020/0190197 A1 | 6/2020 | Calzone et al. |
| 2020/0199242 A1 | 6/2020 | Thompson |
| 2020/0199247 A1 | 6/2020 | Thompson et al. |
| 2020/0206357 A1 | 7/2020 | Alonso et al. |
| 2020/0215206 A1 | 7/2020 | Zhao et al. |
| 2020/0246478 A1 | 8/2020 | Li |
| 2020/0255429 A1 | 8/2020 | He et al. |
| 2020/0276327 A1 | 9/2020 | Li |
| 2020/0291028 A1 | 9/2020 | Poudel et al. |
| 2020/0308175 A1 | 10/2020 | Poudel et al. |
| 2020/0317672 A1 | 10/2020 | He et al. |
| 2020/0338207 A1 | 10/2020 | Geierstanger et al. |
| 2020/0345860 A1 | 11/2020 | Li |
| 2020/0353093 A1 | 11/2020 | Li |
| 2020/0390899 A1 | 12/2020 | Ackerman et al. |
| 2020/0392137 A1 | 12/2020 | He et al. |
| 2020/0405813 A1 | 12/2020 | Yam et al. |
| 2021/0009711 A1 | 1/2021 | Loew et al. |
| 2021/0017172 A1 | 1/2021 | Ahmad et al. |
| 2021/0017274 A1 | 1/2021 | Miao et al. |
| 2021/0024649 A1 | 1/2021 | Engleman et al. |
| 2021/0038643 A1 | 2/2021 | Weissman et al. |
| 2021/0040206 A1 | 2/2021 | Poirier et al. |
| 2021/0040216 A1 | 2/2021 | Chui et al. |
| 2021/0053979 A1 | 2/2021 | Purandare et al. |
| 2021/0069341 A1 | 3/2021 | Gao et al. |
| 2021/0077632 A1 | 3/2021 | Smith et al. |
| 2021/0101902 A1 | 4/2021 | Alper et al. |
| 2021/0115109 A1 | 4/2021 | Thompson et al. |
| 2021/0128737 A1 | 5/2021 | Ren et al. |
| 2021/0128744 A1 | 5/2021 | Kudirka et al. |
| 2021/0130419 A1 | 5/2021 | Nairn et al. |
| 2021/0130467 A1 | 5/2021 | Zalevsky et al. |
| 2021/0130473 A1 | 5/2021 | Baum et al. |
| 2021/0139477 A1 | 5/2021 | Smith et al. |
| 2021/0139604 A1 | 5/2021 | Thompson et al. |
| 2021/0154188 A1 | 5/2021 | Smith et al. |
| 2021/0154214 A1 | 5/2021 | Cooke et al. |
| 2021/0154316 A1 | 5/2021 | Alonso et al. |
| 2021/0154317 A1 | 5/2021 | Thompson et al. |
| 2021/0163600 A1 | 6/2021 | Keyt et al. |
| 2021/0170043 A1 | 6/2021 | Barnett et al. |
| 2021/0179716 A1 | 6/2021 | Chaparro Riggers et al. |
| 2021/0179728 A1 | 6/2021 | Poirier et al. |
| 2021/0187115 A1 | 6/2021 | Alonso et al. |
| 2021/0213010 A1 | 7/2021 | Andresen et al. |
| 2021/0214354 A1 | 7/2021 | Yang |
| 2021/0246211 A1 | 8/2021 | Goldberg et al. |
| 2021/0261548 A1 | 8/2021 | Li et al. |
| 2021/0261549 A1 | 8/2021 | Li et al. |
| 2021/0275683 A1 | 9/2021 | Baum et al. |
| 2021/0284750 A1 | 9/2021 | Jackson et al. |
| 2021/0346387 A1 | 11/2021 | Cortez et al. |
| 2021/0347911 A1 | 11/2021 | Li |
| 2021/0353652 A1 | 11/2021 | Vincent et al. |
| 2021/0363271 A1 | 11/2021 | Li |
| 2022/0001022 A1 | 1/2022 | Ackerman et al. |
| 2022/0016152 A1 | 1/2022 | Li et al. |
| 2022/0016260 A1 | 1/2022 | Strop et al. |

FOREIGN PATENT DOCUMENTS

| | | |
|---|---|---|
| EP | 1689846 B1 | 3/2013 |
| EP | 2674170 A | 12/2013 |
| EP | 2467380 B1 | 11/2016 |
| EP | 2467377 B1 | 12/2016 |
| GB | 2097790 A | 11/1982 |
| JP | 2003-535907 A | 12/2003 |
| JP | 2013-535508 A | 9/2013 |
| WO | WO 90/14844 A2 | 12/1990 |
| WO | WO 00/75605 A1 | 12/2000 |
| WO | WO 00/76518 A1 | 12/2000 |
| WO | WO 00/76519 A1 | 12/2000 |
| WO | WO 01/97843 A2 | 12/2001 |
| WO | WO 02/46749 A2 | 6/2002 |
| WO | WO 03/043572 A2 | 5/2003 |
| WO | WO 2004/028539 A2 | 4/2004 |
| WO | WO 2004/053057 A2 | 6/2004 |
| WO | WO 2004/053452 A2 | 6/2004 |
| WO | WO 2004/058759 A1 | 7/2004 |
| WO | WO 2004/108072 A2 | 12/2004 |
| WO | WO 2005/001022 A2 | 1/2005 |
| WO | WO 2005/003064 A2 | 1/2005 |
| WO | WO 2005/003065 A2 | 1/2005 |
| WO | WO 2005/016275 A2 | 2/2005 |
| WO | WO 2005/018555 A2 | 3/2005 |
| WO | WO 2005/020999 A1 | 3/2005 |
| WO | WO 2005/051324 A2 | 6/2005 |
| WO | WO 2005/094531 A2 | 10/2005 |
| WO | WO 2005/110013 A2 | 11/2005 |
| WO | WO 2005/123080 A2 | 12/2005 |
| WO | WO 2006/028545 A2 | 3/2006 |
| WO | WO 2006/074003 A2 | 7/2006 |
| WO | WO 2006/091394 A2 | 8/2006 |
| WO | WO 2006/091720 A2 | 8/2006 |
| WO | WO 2007/048122 A1 | 4/2007 |
| WO | WO 2007/100634 A2 | 9/2007 |
| WO | WO 2008/009894 A2 | 1/2008 |
| WO | WO 2009/085262 A1 | 7/2009 |
| WO | WO 2010/132622 A2 | 11/2010 |
| WO | WO 2011/022508 A2 | 2/2011 |
| WO | WO 2011/022509 A2 | 2/2011 |
| WO | WO 2012/021834 A1 | 2/2012 |
| WO | WO 2012/092552 A1 | 7/2012 |
| WO | WO 2012/170072 A1 | 12/2012 |
| WO | WO 2013/030378 A1 | 3/2013 |
| WO | WO 2013/067597 A1 | 5/2013 |
| WO | WO 2013/105013 A1 | 7/2013 |
| WO | WO 2013/166110 A1 | 11/2013 |
| WO | WO 2013/180811 A1 | 12/2013 |
| WO | WO 2014/012479 A1 | 1/2014 |
| WO | WO 2014/161887 A1 | 10/2014 |
| WO | WO 2014/177042 A1 | 11/2014 |
| WO | WO 2015/082905 A1 | 6/2015 |
| WO | WO 2015/095418 A1 | 6/2015 |
| WO | WO 2015/103987 A1 | 7/2015 |
| WO | WO 2015/103989 A1 | 7/2015 |
| WO | WO 2015/103990 A1 | 7/2015 |
| WO | WO 2015/112749 A2 | 7/2015 |
| WO | WO 2015/143091 A1 | 9/2015 |
| WO | WO 2015/151078 A2 | 10/2015 |
| WO | WO 2015/151080 A2 | 10/2015 |
| WO | WO 2015/151081 A2 | 10/2015 |
| WO | WO 2015/155753 A2 | 10/2015 |
| WO | WO 2015/165413 A1 | 11/2015 |
| WO | WO 2015/187637 A1 | 12/2015 |
| WO | WO 2016/004875 A1 | 1/2016 |
| WO | WO 2016/004876 A1 | 1/2016 |
| WO | WO 2016/032009 A1 | 3/2016 |
| WO | WO 2016/034085 A1 | 3/2016 |
| WO | WO 2016/055812 A1 | 4/2016 |
| WO | WO 2016/057618 A1 | 4/2016 |
| WO | WO 2016/059622 A2 | 4/2016 |
| WO | WO 2016/064749 A2 | 4/2016 |
| WO | WO 2016/064899 A1 | 4/2016 |

(56) References Cited

FOREIGN PATENT DOCUMENTS

| | | |
|---|---|---|
| WO | WO 2016/085967 A1 | 6/2016 |
| WO | WO 2016/112870 A1 | 7/2016 |
| WO | WO 2016/118754 A1 | 7/2016 |
| WO | WO 2016/141890 A1 | 9/2016 |
| WO | WO 2016/149201 A2 | 9/2016 |
| WO | WO 2016/150899 A2 | 9/2016 |
| WO | WO 2016/161372 A1 | 10/2016 |
| WO | WO 2016/187122 A1 | 11/2016 |
| WO | WO 2016/187656 A1 | 12/2016 |
| WO | WO 2016/198470 A2 | 12/2016 |
| WO | WO 2016/203025 A1 | 12/2016 |
| WO | WO 2016/205551 A2 | 12/2016 |
| WO | WO 2016/205566 A1 | 12/2016 |
| WO | WO 2017/019894 A1 | 2/2017 |
| WO | WO 2017/019896 A1 | 2/2017 |
| WO | WO 2017/019897 A1 | 2/2017 |
| WO | WO 2017/021791 A1 | 2/2017 |
| WO | WO 2017/023779 A1 | 2/2017 |
| WO | WO 2017/024296 A1 | 2/2017 |
| WO | WO 2017/040233 A1 | 3/2017 |
| WO | WO 2017/040234 A1 | 3/2017 |
| WO | WO 2017/044803 A1 | 3/2017 |
| WO | WO 2017/058996 A1 | 4/2017 |
| WO | WO 2017/072662 A1 | 5/2017 |
| WO | WO 2017/079283 A1 | 5/2017 |
| WO | WO 2017/083525 A1 | 5/2017 |
| WO | WO 2017/087280 A1 | 5/2017 |
| WO | WO 2017/100305 A2 | 6/2017 |
| WO | WO 2017/106656 A1 | 6/2017 |
| WO | WO 2017/117269 A1 | 7/2017 |
| WO | WO 2017/118405 A1 | 7/2017 |
| WO | WO 2017/118406 A1 | 7/2017 |
| WO | WO 2017/118407 A1 | 7/2017 |
| WO | WO 2017/165464 A1 | 9/2017 |
| WO | WO 2017/180834 A1 | 10/2017 |
| WO | WO 2017/184746 A1 | 10/2017 |
| WO | WO 2017/210246 A2 | 12/2017 |
| WO | WO 2017/223085 A2 | 12/2017 |
| WO | WO 2018/009916 A1 | 1/2018 |
| WO | WO 2018/045058 A1 | 3/2018 |
| WO | WO 2018/046460 A1 | 3/2018 |
| WO | WO 2018/078620 A1 | 5/2018 |
| WO | WO 2018/086139 A1 | 5/2018 |
| WO | WO 2018/112108 A1 | 6/2018 |
| WO | WO 2018/119474 A2 | 6/2018 |
| WO | WO 2018/119475 A1 | 6/2018 |
| WO | WO 2018/132496 A1 | 7/2018 |
| WO | WO 2018/140831 A2 | 8/2018 |
| WO | WO 2018/144955 A1 | 8/2018 |
| WO | WO 2018/152396 A1 | 8/2018 |
| WO | WO 2018/156617 A2 | 8/2018 |
| WO | WO 2018/166529 A1 | 9/2018 |
| WO | WO 2018/170179 A1 | 9/2018 |
| WO | WO 2018/175854 A1 | 9/2018 |
| WO | WO 2018/176159 A1 | 10/2018 |
| WO | WO 2018/185526 A1 | 10/2018 |
| WO | WO 2018/187515 A1 | 10/2018 |
| WO | WO 2018/191746 A1 | 10/2018 |
| WO | WO 2018/195283 A1 | 10/2018 |
| WO | WO 2018/196823 A1 | 11/2018 |
| WO | WO 2018/198091 A1 | 11/2018 |
| WO | WO 2018/218215 A1 | 11/2018 |
| WO | WO 2018/227018 A1 | 12/2018 |
| WO | WO 2018/227023 A1 | 12/2018 |
| WO | WO 2018/232725 A1 | 12/2018 |
| WO | WO 2019/006038 A1 | 1/2019 |
| WO | WO 2019/023622 A1 | 1/2019 |
| WO | WO 2019/084060 A1 | 5/2019 |
| WO | WO 2019/099412 A1 | 5/2019 |
| WO | WO 2019/118884 A1 | 6/2019 |
| WO | WO 2019/126240 A1 | 6/2019 |
| WO | WO 2019/192454 A1 | 10/2019 |
| WO | WO 2019/222676 A1 | 11/2019 |
| WO | WO 2019/236567 A2 | 12/2019 |
| WO | WO 2020/016662 A2 | 1/2020 |
| WO | WO 2020/023680 A1 | 1/2020 |
| WO | WO 2020/047187 A1 | 3/2020 |
| WO | WO 2020/051356 A1 | 3/2020 |
| WO | WO 2020/056008 A1 | 3/2020 |
| WO | WO 2020/056192 A1 | 3/2020 |
| WO | WO 2020/056194 A1 | 3/2020 |
| WO | WO 2020/056198 A2 | 3/2020 |
| WO | WO 2020/089811 A1 | 5/2020 |
| WO | WO 2020/123425 A1 | 6/2020 |
| WO | WO 2020/139618 A1 | 7/2020 |
| WO | WO 2020/141221 A1 | 7/2020 |
| WO | WO 2020/142659 A2 | 7/2020 |
| WO | WO 2020/168017 A1 | 8/2020 |
| WO | WO 2020/190690 A1 | 9/2020 |
| WO | WO 2020/190725 A1 | 9/2020 |
| WO | WO 2020/190731 A1 | 9/2020 |
| WO | WO 2020/190734 A1 | 9/2020 |
| WO | WO 2020/190760 A1 | 9/2020 |
| WO | WO 2020/190762 A1 | 9/2020 |
| WO | WO 2020/206354 A1 | 10/2020 |
| WO | WO 2020/252015 A1 | 12/2020 |
| WO | WO 2020/252254 A1 | 12/2020 |
| WO | WO 2020/252294 A1 | 12/2020 |
| WO | WO 2020/257235 A1 | 12/2020 |
| WO | WO 2020/257407 A1 | 12/2020 |
| WO | WO 2021/026009 A1 | 2/2021 |
| WO | WO 2021/030665 A1 | 2/2021 |
| WO | WO 2021/046112 A1 | 3/2021 |
| WO | WO 2021/046347 A1 | 3/2021 |
| WO | WO 2021/061867 A1 | 4/2021 |
| WO | WO 2021/067242 A1 | 4/2021 |
| WO | WO 2021/067261 A1 | 4/2021 |
| WO | WO 2021/067644 A1 | 4/2021 |
| WO | WO 2021/081402 A1 | 4/2021 |
| WO | WO 2021/081407 A1 | 4/2021 |
| WO | WO 2021/113679 A1 | 6/2021 |
| WO | WO 2021/136475 A1 | 7/2021 |
| WO | WO 2021/136483 A1 | 7/2021 |
| WO | WO 2021/150701 A1 | 7/2021 |
| WO | WO 2021/150702 A1 | 7/2021 |
| WO | WO 2021/168274 A1 | 8/2021 |
| WO | WO 2021/173832 A1 | 9/2021 |
| WO | WO 2021/202921 A1 | 10/2021 |
| WO | WO 2021/207701 A1 | 10/2021 |
| WO | WO 2021/222894 A1 | 11/2021 |
| WO | WO 2021/226440 A1 | 11/2021 |

OTHER PUBLICATIONS

Feinberg et al., "Mechanism of pathogen recognition by human dectin-2," *J. Biol. Chem.*, 292(32): 13402-13414 (2017).
Kishishita et al., "Trends in the Research and Development of Adjuvants and Vaccines," *Journal of Pharmaceutical Science and Technology*, Japan, 76(1): 46-50 (2016).
Sharma et al., "Preliminary results from a phase 1/2 study of BDC-1001, a novel HER2 targeting TLR7/8 immune-stimulating antibody conjugate (ISAC), in patients (pts) with advanced HER2-expressing solid tumors," *ESMO Immuno-Oncology Congress*, Poster Abstract 164P (2021).
Sharma et al., "Preliminary results from a Phase 1/2 study of BDC-1001, a novel HER2 targeting TLR7/8 immune-stimulating antibody conjugate (ISAC), in patients (pts) with advanced HER2-expressing solid tumors," *American Society of Clinical Oncology* (*ASCO*), Poster 2549 (2021).
Singh et al., "Design of neo-glycoconjugates that target the mannose receptor and enhance TLR-independent cross-presentation and Th1 polarization," *Eur. J. Immunol.*, 41: 916-925 (2011).
Bruno et al., "Population pharmacokinetics of trastuzumab in patients with HER2+ metastatic breast cancer," *Cancer Chemother. and Pharmacol.*, 56: 361-369 (2005).
Kenkel et al., "Dectin-2, a Novel Target for Tumor Macrophage Reprogramming in Cancer Immunotherapy," Poster, Abstract 862 (2021).
Kenkel et al., "PD-L1-targeted ISAC Combines Myeloid Cell Activation, Immune Checkpoint Inhibition and ADCP to Improve

(56) References Cited

OTHER PUBLICATIONS

Anti-tumor Efficacy Over Anti-PD-L1 Antibodies in Preclinical Models," Poster, Abstract 782 (2021).

Mallet et al., "BDC-2034: Discovery of a CEA-targeting Immune-Stimulating Antibody Conjugate (ISAC) for Solid Tumors," Poster, Abstract 784 (2021).

Quartino et al., "Population pharmacokinetic and covariate analyses of intravenous trastuzumab (Herceptin®), a HER2-targeted monoclonal antibody, in patients with a variety of solid tumors," Cancer Chemother. and Pharmacol., 83: 329-340 (2019).

Sharma et al., "Phase 1/2 study of a novel HER2 targeting TLR7/8 immune-stimulating antibody conjugate (ISAC), BDC-1001, alone and in combination with anti-PD1 antibody in patients (pts) with HER2-expressing advanced solid tumors," AACR Poster, Abstract CT218 (2021).

Urban-Wojciuk et al., "The Role of TLRs in Anti-cancer Immunity and Tumor Rejection," Frontiers in Immunology, 10: 2388 (2019).

Abes et al., "Long-lasting antitumor protection by anti-CD20 antibody through cellular immune response," Blood, 116(6): 926-934 (2010).

Ackerman, "Antibody-Adjuvant Conjugates Elicit Robust Myeloid Activation and Durable Anti-Tumor Immunity—A Dissertation Submitted to the Department of Bioengineering and a Committee on Graduate Studies of Stanford University in Partial Fulfillment of the Requirements for the Degree of Doctor of Philosophy," http://purl.stanford.edu/xf251nx6820 (2018).

Ackerman et al., "HER2-Targeting TLR7/8 immune-stimulating antibody conjugates elicit robust myeloid activation and anti-tumor immune responses in a TLR- and FcR-dependent manner," Poster Presented at Society for Immunotherapy of Cancer (2019).

Ackerman et al., "TLR7/8 immune stimulating antibody conjugates elicit robust myeloid activation and durable anti-tumor immunity," Poster Presented at American Association for Cancer Research (2019).

Ackerman et al., "Covalent attachment of a TLR7/8 agonist to tumor-targeting antibodies drives potent anti-tumor efficacy by synergistically activating FcγR- and TLR-signaling and enables safe systemic administration," Poster Presented at Society for Immunotherapy of Cancer (2020).

Ackerman et al., "Immune-stimulating antibody conjugates elicit robust myeloid activation and durable antitumor immunity," Nature Cancer, 2(1): 18-33 (2021).

Adams, "Toll-like receptor agonists in cancer therapy," Immunotherapy, 1(6): 949-964 (2009).

Altin et al., "Targeting dendritic cells with antigen-containing liposomes: antitumor immunity," Expert Opin. Biol. Ther., 4(11): 1735-1747 (2004).

Andreu et al., "FcRy Activation Regulates Inflammation-Associated Squamous Carcinogenesis," Cancer Cell, 17: 121-134 (2010).

Apostolopoulos, et al., "Targeting Antigens to Dendritic Cell Receptors for Vaccine Development," Journal of Drug Delivery, 2013: Article ID 869718 (2013), 22 pp.

Barbuto et al., "Induction of innate and adaptive immunity by delivery of poly dA:dT to dentritic cells," Nature Chemical Biology, 9: 250-56 (2013).

Beesu et al., "Identification of High-Potency Human TLR8 and Dual TLR7/TLR8 Agonists in Pyrimidine-2,4-diamines," Journal of Medicinal Chemistry, 60(5): 2084-98 (2017).

Bensinger et al., "A phase 1 study of lucatumumab, a fully human anti-CD40 antagonist monoclonal antibody administered intravenously to patients with relapsed or refractory multiple myeloma," British Journal of Haematology, 159: 58-66 (2012).

Blumhagen et al., "Alternative pre-mRNA splicing of Toll-like receptor signaling components in peripheral blood mononuclear cells from patients with ARDS," Am. J. Physiol. Lung Cell. Mol. Physiol., 313(5): L930-L939 (2017).

Bolt Biotherapeutics, Inc., "A First-in-human Study Using BDC-1001 in Advanced HER2-Expressing Solid Tumors," ClinicalTrials.gov, https://clinicaltrials.gov/ct2/show/record/NCT04278144?term=Bolt+Investigative+Site&draw=2&rank=1, downloaded Aug. 16, 2021, 9 pp.

Borghaei et al., "Immunotherapy of cancer," European Journal of Pharmacology, 625(1-3): 41-54 (2009).

Brunswick et al., "Surface immunoglobulin crosslinking activates a tyrosine kinase pathway in B cells that is independent of protein kinase C," Proc. Nat. Acad. Sci., 88(4): 1311-1314 (1991).

Carmi et al., "Allogeneic IgG combined with dendritic cell stimuli induce antitumour T-cell immunity," ePub, 521(7550): 99-104 (2015).

Castiglia et al., "Labelling techniques of biomolecules for targeted radiotherapy—Final report of a co-ordinated research project—1998-2002," IAEA-TECDOC-1359, International Atomic Energy Agency (IAEA) (Jul. 2003), 198 pp.

Chabre et al., "Design and creativity in synthesis of multivalent neoglycoconjugates," Advances in Carbohydrate Chemistry and Biochemistry, 2(63): 165-393 (2010).

Cross et al., "Gene Therapy for Cancer Treatment: Past, Present and Future," Clinical Medicine and Research, 4(3): 218-27 (2006).

Crudo et al., "Labeling of the anti-melanoma 14f7 monoclonal antibody with rhenium-188-MAG$_3$ chelate: Conjugation optimization, in vitro stability and animal studies," J. of Radioanal. Nucl., 261(2): 337-342 (2004).

Devisser et al., "De novo carcinogenesis promoted by chronic inflammation is B lymphocyte dependent," Cancer Cell, 7: 411-423 (2005).

Ducancel et al., "Molecular engineering of antibodies for therapeutic and diagnostic purposes," mAbs, 4(4): 445-57 (2012).

Dumbrava et al., "Phase 1/2 study of novel HER2-targeting, TLR7/8 immune-stimulating antibody conjugate (ISAC) BDC-1001 as a single agent and in combination with an immune checkpoint inhibitor in patients with advanced HER2-expressing solid tumors," Poster Presented at San Antonio Breast Cancer Symposium (2020).

Elluru et al., "Regulation of Human Dendritic Cell Functions by Natural Anti-CD40 Antibodies," The TNF Superfamily. Methods in Molecular Biology (Methods and Protocols, Humana Press, New York, NY, 1155: 47-54 (2014).

Esteva et al., "CD40 signaling predicts response to preoperative trastuzumab and concomitant paclitaxel followed by 5-fluorouracil, epirubicin, and cyclophosphamide in HER-2-overexpressing breast cancer," Breast Cancer Research, 9(6): 1-8, R87 (2007).

European Patent Office, International Search Report in International Patent Application No. PCT/US2020/022645, dated Jul. 3, 2020.

European Patent Office, Written Opinion in International Patent Application No. PCT/US2020/022645, dated Jul. 3, 2020.

Fiaux, "Development of New Anticancer Agents based on α-Mannosidase Inhibition," École Polytechnique Fédérale de Lausanne Thèse No. 3793 (Jun. 1, 2007).

Fong et al., "Dendritic Cells in Cancer Immunology," Annu. Rev. Immunol., 18: 245-273 (2000).

Fong et al., "Dendritic cells injected via different routes induce immunity in cancer patients," J. Immunol., 166(6): 4254-4259 (2001).

Friedberg et al., "Combination immunotherapy with a CpG oligonucleotide (1018 ISS) and rituximab in patients with non-Hodgkin lymphoma: increased interferon-1-inducible gene expression, without significant toxicity," Blood, 105(2): 489-495 (2005).

Fritzberg et al., "Specific and stable labeling of antibodies with technetium-99m with a diamide dithiolate chelating agent," Proc. Natl. Acad. Sci. USA, 85: 4025-4029 (1988).

Gadd et al., "Targeted Activation of Toll-Like Receptors: Conjugation of a Toll-Like Receptor 7 Agonist to a Monoclonal Antibody Maintains Antigen Binding and Specificity," Bioconjugate Chemistry, 26: 1743-52 (2015).

Gavino et al., "Identification and expression profiling of a human C-type lectin, structurally homologous to mouse dectin-2," Experimental dermatology, 14(4): 281-288 (2005).

Gerber-Lemaire et al., "Studies toward new anti-cancer strategies based on alpha-mannosidase inhibition," CHIMIA International Journal for Chemistry, 64(9): 634-639 (2010).

Gilboa, "DC-based cancer vaccines," J. Clin. Invest., 117(5): 1195-1203 (2007).

(56) References Cited

OTHER PUBLICATIONS

Gladue et al., "The CD40 agonist antibody CP-870,893 enhances dendritic cell and B-cell activity and promotes anti-tumor efficacy in SCID-hu mice," *Cancer Immunol. Immunother.*, 60(7): 1009-1017 (2011).
Goldwater et al., "A Phase 1, Randomized Ascending Single-Dose Study of Antagonist Anti-Human CD40 ASKP1240 in Healthy Subjects," *American Journal of Transplantation*, 13: 1040-46 (2013).
Hamblett et al., "Altering Antibody-Drug Conjugate Binding to the Neonatal Fc Receptor Impacts Efficacy and Tolerability," *Molecular Pharmaceutics*, 13: 2387-96 (2016).
Hirano et al., "Inhibition of human breast carcinoma growth by a soluble recombinant human CD40 ligand," *Blood*, 93(9): 2999-3007 (1999).
Houot et al., "Targeting immune effector cells to promote antibody-induced cytotoxicity in cancer immunotherapy," *Trends in Immunology*, 32(11): 510-516 (2011).
Hsu et al., "Vaccination of patients with B-cell lymphoma using autologous antigen-pulsed dendritic cells," *Nat. Med.*, 2(1): 52-58 (1996).
Hudziak et al., "p185HER2 monoclonal antibody has antiproliferative effects in vitro and sensitizes human breast tumor cells to tumor necrosis factor," *Mol. Cell. Biol.*, 9(3): 1165-1172 (1989).
Ishikawa et al., "Identification of Distinct Ligands for the C-type Lectin Receptors Mincle and Dectin-2 in the Pathogenic Fungus Malassezia," *Cell Host & Microbe*, 13: 477-88 (2013).
Jain et al., "Engineering antibodies for clinical applications," *TRENDS in Biotechnology*, 25(7): 307-16 (2007).
Jefferis et al., "Human immunoglobulin allotypes," *mAbs*, 1(4): 332-38 (2009).
Jiang et al., "A novel peptide isolated from a phage display peptide library with trastuzumab can mimic antigen epitope of HER-2," *J. Biol. Chem.*, 280(6): 4656-4662 (2005).
Kalinski et al., "Dendritic cells in cancer immunotherapy: vaccines and combination immunotherapies," *Expert Rev. Vaccines*, 12(3): 285-295 (2013).
Kato et al., "Selective and Efficient Gene Delivery of CD40-Ligand by a Fiber-Modified Adenovirus Vector with Specific Antibody to Human Leukemia and Myeloma," *Blood*, 104(11): 5263 (2004).
Kerscher et al., "The Dectin-2 family of C-type lectin-like receptors: an update," *International Immunology*, 25(5): 271-77 (2013).
Khalil et al., "Anti-CD40 agonist antibodies: Preclinical and clinical experience," *Update on Cancer Therapeutics*, 2(2): 61-65 (2007).
Khong et al., "The Use of Agonistic Anti-CD40 Therapy in Treatments for Cancer," *International Reviews of Immunology*, 31(4): 246-266 (2012).
Khong et al., "Agonistic Anti-CD40 Antibody Therapy is Effective Against Postoperative Cancer Recurrence and Metastatis in a Murine Tumor Model," *J. Immunother.*, 36(7): 365-372 (2013).
Kim et al., "Anti-cancer effect and structural characterization of endo-polysaccharide from cultivated mycelia of *Inonotus obliquus*," *Life Sciences*, 79: 72-80 (2006).
Kim et al., "Fcγ receptors enable anticancer action of proapoptotic and immune-modulatory antibodies," *JEM*, 210(9): 1647-1651 (2013).
Kimura et al., "The Innate Immune Receptor Dectin-2 Mediates the Phagocytosis of Cancer Cells by Kupffer Cells for the Suppression of Liver Metastasis," *PNAS*, 113(49): 14097-14102 (2016).
Kokatla et al., "Structure-Based Design of Novel Human Toll-Like Receptor 8 Agonists," *ChemMedChem*, 9: 719-723 (2014).
Kramer et al., "Chemically tunable mucin chimeras assembled on living cells," *PNAS*, 112(41): 12574-12579 (2018).
Krieg et al., "Toll-like receptor 9 (TLR9) agonists in the treatment of cancer," *Oncogene*, 27(2): 161-167 (2008).
Kurts et al., "Cross-priming in health and disease," *Nat. Rev. Immunol.*, 10(6): 4Mar. 414(2010).
Kwekkeboom, "Modulation of Dentritic Cells and Regulatory T Cells by Naturally Occurring Antibodies," *Naturally Occurring Antibodies (Nabs)*, Chapter 10, Landes Bioscience and Springer Science+Business Media, pp. 133-144 (2012).

Leblanc et al., "Systemically administered HER2-targeted ISACs provoke a rapid, local response that engages the innate and adaptive arms of the immune system to eradicate tumors in preclinical models," Poster Presented at Society for Immunotherapy of Cancer (2020).
Li et al., "Generation of tumor-targeted antibody-CpG conjugates," *Journal of Immunological Methods*, 389: 45-51 (2013).
Lim et al., "TLR3 agonists improve the immunostimulatory potential of cetuximab against EGFR + head and neck cancer cells," *Oncolmmunology*, 2(6): e24677-1-e24677-10 (2013).
Loskog et al., "CD40L—A Multipotent Molecule for Tumor Therapy," *Endocrine, Metabolic & Immune Disorders—Drug Targets*, 7(1): 23-28 (2007).
Lu et al., "1-Deoxymannojirimycin, the $\alpha$1,2-mannosidase inhibitor, induced cellular endoplasmic reticulum stress in human hepatocarcinoma cell 7721," *Biochemical and Biophysical Research Communications*, 344: 221-25 (2006).
Lu et al., "Site-specific Antibody-polymer Conjugates for siRNA Delivery," *J. Am. Chem. Soc.*, 135(37): 13885-891 (2013).
Mantovani et al., "Macrophages, innate immunity and cancer: balance, tolerance, and diversity," *Current opinion in immunology*, 22(2): 231-237 (2010).
McDonagh et al., "Engineered anti-CD70 antibody-drug conjugate with increased therapeutic index," *Mol. Cancer. Ther.*, 7(9): 2913-23 (2008).
McGreal et al., "The carbohydrate-recognition domain of Dectin-2 is a C-type lectin with specificity for high mannose," *Glycobiology*, 16(5): 422-30 (2006).
Melief, "Cancer immunotherapy by dendritic cells," *Immunity*, 29(3): 372-383 (2008).
Moga et al., "NK cells stimulated with IL-15 or CpG ODN enhance rituximabdependent cellular cytotoxicity against B-cell lymphoma," *Experimental Hematology*, 36(1): 69-77 (2007).
Mohrbacher et al., "Synergy of CD40L and IL2 Fusion Antibodies in Killing of Malignant B Cells," *Blood*, p. 55b, Abstract #3398 (1999).
Müller et al., "Trastuzumab emtansine (T-DM1) renders HER2+ breast cancer highly susceptible to CTLA-4/PD-1 blockade," *Science Translational Medicine*, 7(315): 5-13 (2015).
Nagengast et al., "In Vivo VEGF Imaging with Radiolabeled Bevacizumab in a Human Ovarian Tumor Xenograft," *J. Nucl. Med.*, 48: 1313-1319 (2007).
Nunez-Prado et al., "The coming of age of engineered multivalent antibodies," *Drug discovery today*, 20(5): 588-594 (2015).
Palucka et al., "Dendritic-cell-based therapeutic cancer vaccines," *Immunity*, 39(1): 38-48 (2013).
Palucka et al., "Cancer Immunotherapy via dendritic cells," *Nature Reviews/Cancer*, 12: 265-277 (2012).
Park et al., "The Therapeutic Effect of Anti-HER2/neu Antibody Depends on Both Innate and Adaptive Immunity," *Cancer Cell*, 18(2): 160-170 (2010).
Perk et al., "$^{89}$Zr as a PET Surrogate Radioisotope for Scouting Biodistribution of the Therapeutic Radiometals $^{90}$Y and $^{177}$Lu in Tumor-Bearing Nude Mice After Coupling to the Internalizing Antibody Cetuximab," *J. Nucl. Med.*, 46: 1898-1906 (2005).
Pham et al., "Tuning a Protein-Labeling Reaction to Achieve Highly Site Selective Lysine Conjugation," *ChemBioChem*, 19: 799-804 (2018).
Pincetic et al., "Type I and type II Fc receptors regulate innate and adaptive immunity," *Nature immunology*, 15: 707-716 (2014).
Pinzon-Charry et al., "The key role of CD40 ligand is overcoming tumor-induced dendritic cell dysfunction," *Breast Cancer Res.*, 8(1): 402 (2006).
Presta, "Engineering of therapeutic antibodies to minimize immunogenicity and optimize function," *Advanced Drug Delivery Reviews*, 58: 640-56 (2006).
Poon et al., "Preclinical safety profile of trastuzumab emtansine (T-DM1): mechanism of action of its cytotoxic component retained with improved tolerability," *Toxicol. Appl. Pharmacol.*, 273(2): 298-313 (2013).
Quanta Biodesign, Ltd., "TFP Esters Have More Hydrolytic Stability and Greater Reactivity Than NHS Esters," Flyer (2014), 2 pp.

(56) References Cited

OTHER PUBLICATIONS

Rafiq et al., "Immune complex-mediated antigen presentation induces tumor immunity," *The Journal of Clinical Investigation*, 110(1): 71-79 (2002).
Riemer et al., "Matching of trastuzumab (Herceptin®) epitope mimics onto the surface of Her-2/neu—a new method of epitope definition," *Mol. Immunol.* 42: 1121-24 (2005).
Rycyzyn et al., "The Use of an Anti-CD40 Agonist Monoclonal Antibody During Immunizations Enhances Hybridoma Generation," *Hybridoma*, 27(1): 25-30 (2008).
Sancho et al., "Signaling by Myeloid C-Type Lectin Receptors in Immunity and Homeostasis," *Annu. Rev. Immunol.*, 30: 491-529 (2012).
Sato et al., "Dectin-2 Is a Pattern Recognition Receptor for Fungi That Couples with the Fc Receptor γ Chain to Induce Innate Immune Responses," *The Journal of Biological Chemistry*, 281(50): 38854-66 (2006).
Schettini et al., "Intratumoral delivery of CpG-conjugated anti-MUC1 antibody enhances NK cell anti-tumor activity," *Cancer Immunology*, 61(11): 2055-2065 (2012).
Schuurhuis et al., "Immune Complex-Loaded Dendritic Cells Are Superior to Soluble Immune Complexes as Antitumor Vaccine," *J. Immunol.*, 176(8): 4573-4580 (2006).
Schwenk et al., "IgG2 Antibodies against a Clinical Grade Plasmodium falciparum CSP Vaccine Antigen Associate with Protection against Transgenic Sporozoite Challenge in Mice," *PLoS One*, 9(10): e111020 (2014).
Sharma et al., "Phase 1/2 study of novel HER2-targeting, TLR7/8 immune-stimulating antibody conjugate (ISAC) BDC-1001 with or without immune checkpoint inhibitor in patients with advanced HER2-expressing solid tumors," Poster Presented at Society for Immunotherapy of Cancer (2020).
Sharma et al., "Phase 1/2 study of novel HER2-targeting, TLR7/8 immune-stimulating antibody conjugate (ISAC) BDC-1001 with or without immune checkpoint inhibitor in patients with advanced HER2-expressing solid tumors," *Journal for Immunotherapy of Cancer*, 8(Suppl. 3): A244 (2020).
Shi et al., "Engagement of immune effector cells by trastuzumab induces HER2/ERBB2 downregulation in cancer cells through STAT1 activation," *Breast Cancer Research*, 16: R33 (2014).
Shoenfeld et al., "Gamma-globulin inhibits tumor spread in mice," *International Immunology*, 11(8): 1247-51 (1999).
Shukla et al., "Toward self-adjuvanting subunit vaccines: Model peptide and protein antigens incorporating covalently bound toll-like receptor-7 agonistic imidazoquinolines," *Bioorganic & Medicinal Chemistry Letters*, 21 (11): 3232-3236 (2011).
Somlai et al., "Synthesis and Use of Pentafluorophenyl 6-(Biotinylamido)hexanoate—An Alternative Reagent for Labelling of Proteins with Biotin Moiety," *Z. Naturforsch*, 48b: 511-516 (1993).
Spitzer et al., "Systemic Immunity Is Required for Effective Cancer Immunotherapy," *Cell*, 168: 1-16 (2017).
Stancovski et al., "Mechanistic aspects of the opposing effects of monoclonal antibodies to the ERBB2 receptor on tumor growth," *Proc. Natl. Acad. Sci. USA*, 88(19): 8691-8695 (1991).
Steinman et al., "Taking dendritic cells into medicine," *Nature*, 449(7161): 419-426 (2007).
Suzuki et al., "Antitumor Activity of Polysaccharides. II. Growth-Inhibitory Activity of Mannan Fractions Isolated From Several Species of Yeasts Against Sarcoma-180 Solid Tumor," *GANN*, 60: 65-69 (1969).
Tham et al., "Melanoma-initiating cells exploit M2 macrophage TGFβ and arginase pathway for survival and proliferation," *Oncotarget*, 5(23): 12027-12042 (2014).
Thermo Fisher Scientific Inc., "Thermo Scientific Avidin-Biotin Technical Handbook," www.thermo.com/perbio (2009), 51 pp.
Trombetta et al., "Cell Biology of Antigen Processing In Vitro and In Vivo," *Annu. Rev. Immunol.*, 23: 975-1028 (2005).
Tseng et al., "Anti-CD47 antibody-mediated phagocytosis of cancer by macrophages primes an effective antitumor T-cell response," *Proc. Natl. Acad. Sci. USA*, 110(27): 111Mar. 11108 (2013).
Turpin et al., "The ErbB2ΔEx16 splice variant is a major oncogenic driver in breast cancer that promotes a pro-metastatic tumor microenvironment," *Oncogene*, 35(47): 6053-6054 (2016).
Upchurch et al., "Preclinical Assessment of the Effectiveness of α-Dectin-1-Pam3 Conjugate in Controlling $T_H2$ Responses," *J. Allergy Clin. Immunol.*, Abstract No. 326, 135(2): AB101 (2015).
Vacchelli et al., "Toll-like receptor agonists for cancer therapy," *OncoImmunology*, 2(8): e25238-1-e25238-14 (2013).
Van Berkel et al., "Rapid production of recombinant human IgG with improved ADCC effector function in a transient expression system," *Biotechnology and bioengineering*, 105(2): 350-357 (2010).
Van Gog et al., "Monoclonal Antibodies Labeled with Rhenium-186 Using the MAG3 Chelate: Relationship between the Number of Chelated Groups and Biodistribution Characteristics," *J. Nucl. Med.*, 37: 352-362 (1996).
Verel et al., "$_{89}$Zr Immuno-PET: Comprehensive Procedures for the Production of $^{89}$Zr-Labeled Monoclonal Antibodies," *J. Nucl. Med.*, 44: 1271-1281 (2003).
Visser et al., "Labeling of Monoclonal Antibodies with Rhenium-186 Using the MAG3 Chelate for Radioimmunotherapy of Cancer: A Technical Protocol," *J. Nucl. Med.*, 34: 1953-1963 (1993).
Vonderheide et al., "Agonistic CD40 Antibodies and Cancer Therapy," *Clin. Cancer Res.*, 19(5): 1035-1043 (2013).
Vrouenraets et al., "Development of meta-Tetrahydroxyphenylchlorin-Monoclonal Antibody Conjugates for Photoimmunotherapy," *Cancer Research*, 59: 1505-1513 (1999).
Vrouenraets et al., "Targeting of Aluminum (III) Phtalocyanine Tetrasulfonate by Use of Internalizing Monoclonal Antibodies: Improved Efficacy in Photodynamic Therapy," *Cancer Research*, 61: 1970-1975 (2001).
Vrouenraets et al., "Targeting of a Hydrophilic Photosensitizer by Use of Internalizing Monoclonal Antibodies: A New Possibility for Use in Photodynamic Therapy," *Int. J. Cancer*, 88: 108-114 (2000).
Wakim et al. "High does intravenous immunoglobulin in atopic dermatitis and hyper-IgE syndrome," *Ann. Allergy Asthma Immunol.*, 81(2): 153-158 (1998).
Wang et al. "Effective antibody therapy induces host-protective antitumor immunity that is augmented by TLR4 agonist treatment," *Cancer Immunology Immunotherapy*, 61(1): 49-61 (2012).
Wang et al., "Antigen targeting to dendritic cells with bispecific antibodies," *J. Immunol. Methods*, 306(1-2): 80-92 (2005).
Warren et al., "Synergism Between Cytosine-Guanine Oligodeoxynucleotides and Monoclonal Antibody in the Treatment of Lymphoma," *Seminars in Oncology*, 29(1, Suppl. 2): 93-97 (2002).
Willimsky et al., "Immunogenicity of premalignant lesions is the primary cause of general cytotoxic T lymphocyte unresponsiveness," *J. Exp. Med.*, 205(7): 1687-1700 (2008).
Wingett et al., "CD40 is functionally expressed on human breast carcinomas: variable inducibility by cytokines and enhancement of Fas-mediated apoptosis," *Breast Cancer Res. Treat.*, 50(1): 27-36 (1998).
Wooldridge et al., "T-cell activation induced by anti-CD3 x anti-B-cell lymphoma monoclonal antibody is enhanced by pretreatment of lymphoma cells with soluble CD40 ligand," *Cancer Immunol. Immunother.*, 45(3-4): 174-179 (1997).
Yan et al., "Targeting C-type lectin receptors for cancer immunity," *Frontiers in Immunology*, 6(408): 1-9 (2015).
Yang et al., "M-CSF cooperating with $NF_KB$ induces macrophage transformation from M1 to M2 by upregulating c-Jun," *Cancer Biology & Therapy*, 15(1): 99-107 (2014).
Yao et al., "Methods to Design and Synthesize Antibody-Drug Conjugates (ADCs)," *International Journal of Molecular Sciences*, 17, 194 (2016).
Zambianchi et al., "Microwave-Assisted Synthesis of Thiophene Fluorophores, Labeling and Multilabeling of Monoclonal Antibodies, and Long Lasting Staining of Fixed Cells," *J. Am. Chem. Soc.*, 131: 10892-10900 (2009).

(56) References Cited

OTHER PUBLICATIONS

Zhou et al., "Development of a simple and rapid method for producing nonfucosylated oligomannose containing antibodies with increased effector function," *Biotechnology and bioengineering*, 99(3): 652-665 (2008).

Zhou et al., "N-Carboxyanhydride Polymerization of Glycopolypeptides That Activate Antigen-Presenting Cells through Dectin-1 and Dectin-2," *Angew. Chem. Int. Ed.*, 57: 3137-3142 (2018).

SEQUENCE LISTING

```
<160> NUMBER OF SEQ ID NOS: 33

<210> SEQ ID NO 1
<211> LENGTH: 1255
<212> TYPE: PRT
<213> ORGANISM: Homo sapiens

<400> SEQUENCE: 1

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255
```

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg

-continued

```
            675                 680                 685
Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095
```

```
Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 2
<211> LENGTH: 11
<212> TYPE: PRT
<213> ORGANISM: Homo sapiens

<400> SEQUENCE: 2

Arg Ala Ser Gln Asp Val Asn Thr Ala Val Ala
1               5                   10

<210> SEQ ID NO 3
<211> LENGTH: 7
<212> TYPE: PRT
<213> ORGANISM: Homo sapiens

<400> SEQUENCE: 3

Ser Ala Ser Phe Leu Tyr Ser
1               5

<210> SEQ ID NO 4
<211> LENGTH: 9
<212> TYPE: PRT
<213> ORGANISM: Homo sapiens

<400> SEQUENCE: 4

Gln Gln His Tyr Thr Thr Pro Pro Thr
1               5

<210> SEQ ID NO 5
<211> LENGTH: 5
<212> TYPE: PRT
<213> ORGANISM: Homo sapiens

<400> SEQUENCE: 5

Asp Thr Tyr Ile His
1               5
```

```
<210> SEQ ID NO 6
<211> LENGTH: 17
<212> TYPE: PRT
<213> ORGANISM: Homo sapiens

<400> SEQUENCE: 6

Arg Ile Tyr Pro Thr Asn Gly Tyr Thr Arg Tyr Ala Asp Ser Val Lys
1               5                   10                  15

Gly

<210> SEQ ID NO 7
<211> LENGTH: 11
<212> TYPE: PRT
<213> ORGANISM: Homo sapiens

<400> SEQUENCE: 7

Trp Gly Gly Asp Gly Phe Tyr Ala Met Asp Tyr
1               5                   10

<210> SEQ ID NO 8
<211> LENGTH: 23
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 9
<211> LENGTH: 15
<212> TYPE: PRT
<213> ORGANISM: Homo sapiens

<400> SEQUENCE: 9

Trp Tyr Gln Gln Lys Pro Gly Lys Ala Pro Lys Leu Leu Ile Tyr
1               5                   10                  15

<210> SEQ ID NO 10
<211> LENGTH: 32
<212> TYPE: PRT
<213> ORGANISM: Homo sapiens

<400> SEQUENCE: 10

Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 11
<211> LENGTH: 10
<212> TYPE: PRT
<213> ORGANISM: Homo sapiens

<400> SEQUENCE: 11

Phe Gly Gln Gly Thr Lys Val Glu Ile Lys
1               5                   10

<210> SEQ ID NO 12
<211> LENGTH: 30
<212> TYPE: PRT
<213> ORGANISM: Homo sapiens
```

<400> SEQUENCE: 12

Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys
            20                  25                  30

<210> SEQ ID NO 13
<211> LENGTH: 14
<212> TYPE: PRT
<213> ORGANISM: Homo sapiens

<400> SEQUENCE: 13

Trp Val Arg Gln Ala Pro Gly Lys Gly Leu Glu Trp Val Ala
1               5                   10

<210> SEQ ID NO 14
<211> LENGTH: 32
<212> TYPE: PRT
<213> ORGANISM: Homo sapiens

<400> SEQUENCE: 14

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 15
<211> LENGTH: 11
<212> TYPE: PRT
<213> ORGANISM: Homo sapiens

<400> SEQUENCE: 15

Trp Gly Gln Gly Thr Leu Val Thr Val Ser Ser
1               5                   10

<210> SEQ ID NO 16
<211> LENGTH: 11
<212> TYPE: PRT
<213> ORGANISM: Homo sapiens

<400> SEQUENCE: 16

Lys Ala Ser Gln Asp Val Ser Ile Gly Val Ala
1               5                   10

<210> SEQ ID NO 17
<211> LENGTH: 7
<212> TYPE: PRT
<213> ORGANISM: Homo sapiens

<400> SEQUENCE: 17

Ser Ala Ser Tyr Arg Tyr Thr
1               5

<210> SEQ ID NO 18
<211> LENGTH: 9
<212> TYPE: PRT
<213> ORGANISM: Homo sapiens

<400> SEQUENCE: 18

Gln Gln Tyr Tyr Ile Tyr Pro Tyr Thr
1               5

<210> SEQ ID NO 19

```
<211> LENGTH: 5
<212> TYPE: PRT
<213> ORGANISM: Homo sapiens

<400> SEQUENCE: 19

Asp Tyr Thr Met Asp
1               5

<210> SEQ ID NO 20
<211> LENGTH: 17
<212> TYPE: PRT
<213> ORGANISM: Homo sapiens

<400> SEQUENCE: 20

Asp Val Asn Pro Asn Ser Gly Gly Ser Ile Tyr Asn Gln Arg Phe Lys
1               5                   10                  15

Gly

<210> SEQ ID NO 21
<211> LENGTH: 10
<212> TYPE: PRT
<213> ORGANISM: Homo sapiens

<400> SEQUENCE: 21

Asn Leu Gly Pro Ser Phe Tyr Phe Asp Tyr
1               5                   10

<210> SEQ ID NO 22
<211> LENGTH: 23
<212> TYPE: PRT
<213> ORGANISM: Homo sapiens

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 23
<211> LENGTH: 15
<212> TYPE: PRT
<213> ORGANISM: Homo sapiens

<400> SEQUENCE: 23

Trp Tyr Gln Gln Lys Pro Gly Lys Ala Pro Lys Leu Leu Ile Tyr
1               5                   10                  15

<210> SEQ ID NO 24
<211> LENGTH: 32
<212> TYPE: PRT
<213> ORGANISM: Homo sapiens

<400> SEQUENCE: 24

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 25
<211> LENGTH: 10
<212> TYPE: PRT
<213> ORGANISM: Homo sapiens

<400> SEQUENCE: 25
```

```
Phe Gly Gln Gly Thr Lys Val Glu Ile Lys
1               5                   10
```

<210> SEQ ID NO 26
<211> LENGTH: 30
<212> TYPE: PRT
<213> ORGANISM: Homo sapiens

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr
            20                  25                  30
```

<210> SEQ ID NO 27
<211> LENGTH: 14
<212> TYPE: PRT
<213> ORGANISM: Homo sapiens

<400> SEQUENCE: 27

```
Trp Val Arg Gln Ala Pro Gly Lys Gly Leu Glu Trp Val Ala
1               5                   10
```

<210> SEQ ID NO 28
<211> LENGTH: 32
<212> TYPE: PRT
<213> ORGANISM: Homo sapiens

<400> SEQUENCE: 28

```
Arg Phe Thr Leu Ser Val Asp Arg Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 29
<211> LENGTH: 11
<212> TYPE: PRT
<213> ORGANISM: Homo sapiens

<400> SEQUENCE: 29

```
Trp Gly Gln Gly Thr Leu Val Thr Val Ser Ser
1               5                   10
```

<210> SEQ ID NO 30
<211> LENGTH: 214
<212> TYPE: PRT
<213> ORGANISM: Homo sapiens

<400> SEQUENCE: 30

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 450
<212> TYPE: PRT
<213> ORGANISM: Homo sapiens

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                245                 250                 255
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 32
<211> LENGTH: 214
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 33
<211> LENGTH: 448
<212> TYPE: PRT
<213> ORGANISM: Homo sapiens

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

IMMUNOCONJUGATES TARGETING HER2

CROSS-REFERENCE TO RELATED APPLICATIONS

This patent application is a continuation of International Patent Application PCT/US2020/022645, filed Mar. 13, 2020, which claims the benefit of U.S. Provisional Patent Application No. 62/819,356, filed Mar. 15, 2019, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 28,649 Byte ASCII (Text) file named "756420 ST25.txt," created Aug. 31, 2021.

BACKGROUND OF THE INVENTION

It is now well appreciated that tumor growth necessitates the acquisition of mutations that facilitate immune evasion. Even so, tumorigenesis results in the accumulation of mutated antigens, or neoantigens, that are readily recognized by the host immune system following ex vivo stimulation. Why and how the immune system fails to recognize neoantigens are beginning to be elucidated. Groundbreaking studies by Carmi et al. (Nature, 521: 99-104 (2015)) have indicated that immune ignorance can be overcome by delivering neoantigens to activated dendritic cells via antibody-tumor immune complexes. In these studies, simultaneous delivery of tumor binding antibodies and dendritic cell adjuvants via intratumoral injections resulted in robust anti-tumor immunity. New compositions and methods for the delivery of antibodies and dendritic cell adjuvants are needed in order to reach inaccessible tumors and/or to expand treatment options for cancer patients and other subjects. The invention provides such compositions and methods.

BRIEF SUMMARY OF THE INVENTION

The invention provides an immunoconjugate of formula:

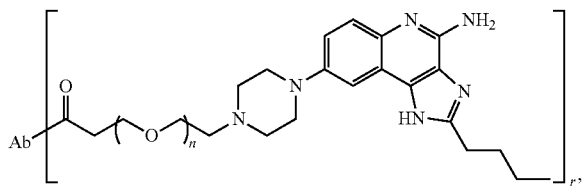

or pharmaceutically acceptable salt thereof, wherein subscript r is an integer from 1 to 10, subscript n is an integer from about 2 to about 25, and "Ab" is an antibody construct that has an antigen binding domain that binds the protein human epidermal growth factor receptor 2 ("HER2").

The invention provides a composition comprising a plurality of immunoconjugates described herein.

The invention provides a method for treating cancer in a subject comprising administering a therapeutically effective amount of an immunoconjugate or a composition described herein to a subject in need thereof.

DETAILED DESCRIPTION OF THE INVENTION

Figure 1A:
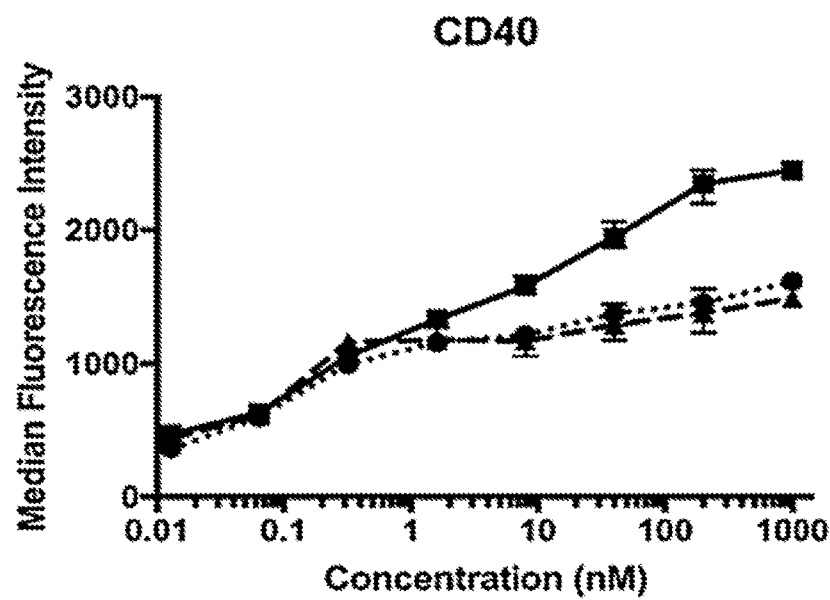
FIG. 1A shows the effect of Immunoconjugate A on myeloid activation in myeloid APC-tumor co-cultures, using the HCC1954 human ductal carcinoma tumor cell line. Median fluorescence intensity of co-stimulatory molecule CD40 (cells gated on viable CD45+CD11c+HLA-DR+) was measured by flow cytometry and is shown for trastuzumab (dotted line, circle), trastuzumab+Compound 7 (dashed line, triangle) or Immunoconjugate A (solid line, square).

The invention provides an immunoconjugate of formula:

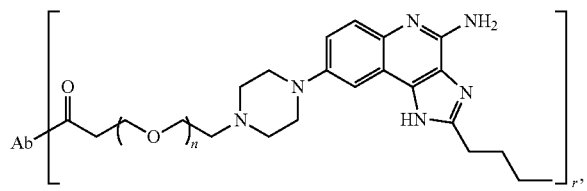

or pharmaceutically acceptable salt thereof, wherein subscript r is an integer from 1 to 10, subscript n is an integer from about 2 to about 25, and "Ab" is an antibody construct that has an antigen binding domain that binds human epidermal growth factor receptor 2 ("HER2").

Antibody-adjuvant immunoconjugates of the invention, comprising an antibody construct that has an antigen binding domain that binds HER2 linked to one or more adjuvant of formula:

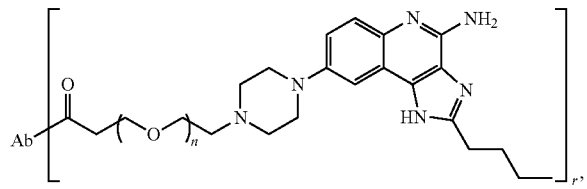

demonstrate superior pharmacological properties over conventional antibody conjugates. The polyethylene glycol-based linker ("PEG linker") is the preferred linker to provide adequate purification and isolation of the immunoconjugate, maintain function of the one or more adjuvant moieties and antibody construct, and produce ideal pharmacokinetic ("PK") properties of the immunoconjugate. Additional embodiments and benefits of the inventive antibody-adjuvant immunoconjugates will be apparent from description herein.

Definitions

As used herein, the term "immunoconjugate" refers to an antibody construct that is covalently bonded to an adjuvant moiety via a linker.

As used herein, the phrase "antibody construct" refers to an antibody or a fusion protein comprising (i) an antigen binding domain and (ii) an Fc domain.

As used herein, the term "antibody" refers to a polypeptide comprising an antigen binding region (including the complementarity determining region (CDRs)) from an immunoglobulin gene or fragments thereof that specifically binds and recognizes HER2.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa) connected by disulfide bonds. Each chain is composed of structural domains, which are referred to as immunoglobulin domains. These domains are classified into different categories by size and function, e.g., variable domains or regions on the light and heavy chains ($V_L$ and $V_H$, respectively) and constant domains or regions on the light and heavy chains ($C_L$ and $C_H$, respectively). The N-terminus of each chain defines a variable region of about 100 to 110 or more amino acids, referred to as the paratope, primarily responsible for antigen recognition, i.e., the antigen binding domain. Light chains are classified as either kappa or lambda. Heavy chains are classified as gamma, mu, alpha, delta, or epsilon, which in turn define the immunoglobulin classes, IgG, IgM, IgA, IgD and IgE, respectively. IgG antibodies are large molecules of about 150 kDa composed of four peptide chains. IgG antibodies contain two identical class γ heavy chains of about 50 kDa and two identical light chains of about 25 kDa, thus a tetrameric quaternary structure. The two heavy chains are linked to each other and to a light chain each by disulfide bonds. The resulting tetramer has two identical halves, which together form the Y-like shape. Each end of the fork contains an identical antigen binding domain. There are four IgG subclasses (IgG1, IgG2, IgG3, and IgG4) in humans, named in order of their abundance in serum (i.e., IgG1 is the most abundant). Typically, the antigen binding domain of an antibody will be most critical in specificity and affinity of binding to cancer cells.

Antibodies can exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_H$1 by a disulfide bond. The F(ab)'2 may be reduced under mild conditions to break the disulfide linkage in the hinge region, thereby converting the F(ab)'2 dimer into a Fab' monomer. The Fab' monomer is essentially Fab with part of the hinge region (see, e.g., *Fundamental Immunology* (Paul, editor, 7th edition, 2012)). While various antibody fragments are defined in terms of the digestion of an intact antibody, such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv), or those identified using phage display libraries (see, e.g., McCafferty et al., *Nature*, 348: 552-554 (1990)).

The term "antibody" specifically encompasses monoclonal antibodies (including full length monoclonal antibodies), polyclonal antibodies, multi specific antibodies (e.g., bispecific antibodies), and antibody fragments that exhibit the desired biological activity.

As used herein, the term "epitope" means any antigenic determinant or epitopic determinant of an antigen to which an antigen binding domain binds (i.e., at the paratope of the antigen binding domain). Antigenic determinants usually consist of chemically active surface groupings of molecules, such as amino acids or sugar side chains, and usually have specific three dimensional structural characteristics, as well as specific charge characteristics.

As used herein, "HER2" refers to the protein human epidermal growth factor receptor 2 (SEQ ID NO: 1), or an antigen with least about 70%, about 75%, about 80%, about 85%, about 90%, about 91%, about 92%, about 93%, about 94%, about 95%, about 96%, about 97%, about 98%, about 99%, or more sequence identity to SEQ ID NO: 1.

Percent (%) identity of sequences can be calculated, for example, as $100\times[(identical\ positions)/min(TG_A, TG_B)]$, where $TG_A$ and $TG_B$ are the sum of the number of residues and internal gap positions in peptide sequences A and B in the alignment that minimizes $TG_A$ and $TG_B$. See, e.g., Russell et al., *J. Mol Biol.*, 244: 332-350 (1994).

As used herein, the term "adjuvant" refers to a substance capable of eliciting an immune response in a subject exposed to the adjuvant. The phrase "adjuvant moiety" refers to an adjuvant that is covalently bonded to an antibody construct, e.g., through a linker, as described herein. The adjuvant moiety can elicit the immune response while bonded to the antibody construct or after cleavage (e.g., enzymatic cleavage) from the antibody construct following administration of an immunoconjugate to the subject.

As used herein, the terms "Toll-like receptor" and "TLR" refer to any member of a family of highly-conserved mammalian proteins which recognizes pathogen-associated molecular patterns and acts as key signaling elements in innate immunity. TLR polypeptides share a characteristic structure that includes an extracellular domain that has leucine-rich repeats, a transmembrane domain, and an intracellular domain that is involved in TLR signaling.

The terms "Toll-like receptor 7" and "TLR7" refer to nucleic acids or polypeptides sharing at least about 70%, about 80%, about 90%, about 95%, about 96%, about 97%, about 98%, about 99%, or more sequence identity to a publicly-available TLR7 sequence, e.g., GenBank accession number AAZ99026 for human TLR7 polypeptide, or GenBank accession number AAK62676 for murine TLR7 polypeptide.

The terms "Toll-like receptor 8" and "TLR8" refer to nucleic acids or polypeptides sharing at least about 70%, about 80%, about 90%, about 95%, about 96%, about 97%, about 98%, about 99%, or more sequence identity to a publicly-available TLR7 sequence, e.g., GenBank accession number AAZ95441 for human TLR8 polypeptide, or GenBank accession number AAK62677 for murine TLR8 polypeptide.

A "TLR agonist" is a substance that binds, directly or indirectly, to a TLR (e.g., TLR7 and/or TLR8) to induce TLR signaling. Any detectable difference in TLR signaling can indicate that an agonist stimulates or activates a TLR. Signaling differences can be manifested, for example, as changes in the expression of target genes, in the phosphorylation of signal transduction components, in the intracellular localization of downstream elements such as nuclear factor-κB (NF-κB), in the association of certain components (such as IL-1 receptor associated kinase (IRAK)) with other proteins or intracellular structures, or in the biochemical activity of components such as kinases (such as mitogen-activated protein kinase (MAPK)).

As used herein, "Ab" refers to an antibody construct that has an antigen-binding domain that binds HER2 (e.g., trastuzumab (also known as HERCEPTIN™), a biosimilar thereof, or a biobetter thereof.

As used herein, the term "biosimilar" refers to an approved antibody construct that has active properties similar to the antibody construct previously approved (e.g., trastuzumab).

As used herein, the term "biobetter" refers to an approved antibody construct that is an improvement of a previously approved antibody construct (e.g., trastuzumab). The biobetter can have one or more modifications (e.g., an altered glycan profile, or a unique epitope) over the previously approved antibody construct.

As used herein, the term "amino acid" refers to any monomeric unit that can be incorporated into a peptide, polypeptide, or protein. Amino acids include naturally-occurring α-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid). The amino acids can be glycosylated (e.g., N-linked glycans, O-linked glycans, phosphoglycans, C-linked glycans, or glypiation) or deglycosylated.

Naturally-occurring amino acids are those encoded by the genetic code, as well as those amino acids that are later modified, e.g., hydroxyproline, γ-carboxyglutamate, and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, and methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either the commonly known three letter symbols or by the one-letter symbols recommended by the IUPAC-IUB Biochemical Nomenclature Commission.

As used herein, the term "linker" refers to a functional group that covalently bonds two or more moieties in a compound or material. For example, the linking moiety can serve to covalently bond an adjuvant moiety to an antibody construct in an immunoconjugate.

As used herein, the terms "treat," "treatment," and "treating" refer to any indicia of success in the treatment or amelioration of an injury, pathology, condition (e.g., cancer), or symptom (e.g., cognitive impairment), including any objective or subjective parameter such as abatement; remission; diminishing of symptoms or making the symptom, injury, pathology, or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter, including, for example, the result of a physical examination.

The terms "cancer," "neoplasm," and "tumor" are used herein to refer to cells which exhibit autonomous, unregulated growth, such that the cells exhibit an aberrant growth phenotype characterized by a significant loss of control over cell proliferation. Cells of interest for detection, analysis, and/or treatment in the context of the invention include cancer cells (e.g., cancer cells from an individual with cancer), malignant cancer cells, pre-metastatic cancer cells, metastatic cancer cells, and non-metastatic cancer cells. Cancers of virtually every tissue are known. The phrase "cancer burden" refers to the quantum of cancer cells or cancer volume in a subject. Reducing cancer burden accordingly refers to reducing the number of cancer cells or the cancer cell volume in a subject. The term "cancer cell" as used herein refers to any cell that is a cancer cell (e.g., from any of the cancers for which an individual can be treated, e.g., isolated from an individual having cancer) or is derived from a cancer cell, e.g., clone of a cancer cell. For example, a cancer cell can be from an established cancer cell line, can be a primary cell isolated from an individual with cancer, can be a progeny cell from a primary cell isolated from an individual with cancer, and the like. In some embodiments, the term can also refer to a portion of a cancer cell, such as a sub-cellular portion, a cell membrane portion, or a cell lysate of a cancer cell. Many types of cancers are known to those of skill in the art, including solid tumors such as carcinomas, sarcomas, glioblastomas, melanomas, lymphomas, and myelomas, and circulating cancers such as leukemias.

As used herein, the term "cancer" includes any form of cancer, including but not limited to, solid tumor cancers (e.g., lung, prostate, breast, gastric, bladder, colon, ovarian, pancreas, kidney, liver, glioblastoma, medulloblastoma, leiomyosarcoma, head & neck squamous cell carcinomas, melanomas, and neuroendocrine) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors. Any HER2 expressing cancer is a suitable cancer to be treated by the subject methods and compositions. As used herein "HER2 expression" refers to a cell that has a HER2 receptor on the cell's surface. For example, a cell may have from about 20,000 to about 50,000 HER2 receptors on the cell's surface. As used herein "HER2 overexpression" refers to a cell that has more than about 50,000 HER2 receptors. For example, a cell 2, 5, 10, 100, 1,000, 10,000, 100,000, or 1,000,000 times the number of HER2 receptors as compared to corresponding non-cancer cell (e.g., about 1 or 2 million HER2 receptors). It is estimated that HER2 is overexpressed in about 25% to about 30% of breast cancers.

Carcinomas are malignancies that originate in the epithelial tissues. Epithelial cells cover the external surface of the body, line the internal cavities, and form the lining of glandular tissues. Examples of carcinomas include, but are not limited to, adenocarcinoma (cancer that begins in glandular (secretory) cells such as cancers of the breast, pancreas, lung, prostate, stomach, gastroesophageal junction, and colon) adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostate, pancreas, colon, brain (usually as secondary metastases), lung, breast, and skin.

Soft tissue tumors are a highly diverse group of rare tumors that are derived from connective tissue. Examples of soft tissue tumors include, but are not limited to, alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DF SP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; pleomorphic adenoma of soft tissue; and neoplasias derived from fibroblasts, myofibroblasts, histiocytes, vascular cells/endothelial cells, and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to, askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; and undifferentiated pleomorphic sarcoma).

A teratoma is a type of germ cell tumor that may contain several different types of tissue (e.g., can include tissues derived from any and/or all of the three germ layers: endoderm, mesoderm, and ectoderm), including, for example, hair, muscle, and bone. Teratomas occur most often in the ovaries in women, the testicles in men, and the tailbone in children.

Melanoma is a form of cancer that begins in melanocytes (cells that make the pigment melanin). Melanoma may begin in a mole (skin melanoma), but can also begin in other pigmented tissues, such as in the eye or in the intestines.

Leukemias are cancers that start in blood-forming tissue, such as the bone marrow, and cause large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is affected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to, Acute myeloid leukemia (AML), Acute lymphoblastic leukemia (ALL), Chronic myeloid leukemia (CIVIL), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One category of lymphoma is Hodgkin lymphoma (HL), which is marked by the presence of a type of cell called the Reed-Sternberg cell. There are currently 6 recognized types of HL. Examples of Hodgkin lymphomas include nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to, AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to, gliomas (e.g., glioblastomas, astrocytomas, oligodendrogliomas, ependymomas, and the like), meningiomas, pituitary adenomas, and vestibular schwannomas, primitive neuroectodermal tumors (medulloblastomas).

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, and invasion of surrounding or distant tissues or organs, such as lymph nodes.

As used herein, the phrases "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs, therefore, tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part that is not directly connected to the organ of the original cancerous tumor. Metastasis can also be defined as several steps of a process, such as the departure of cancer cells from an original tumor site, and migration and/or invasion of cancer cells to other parts of the body.

As used herein the phrases "effective amount" and "therapeutically effective amount" refer to a dose of a substance such as an immunoconjugate that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); *Goodman & Gilman's The Pharmacological Basis of Therapeutics,* 11th Edition (McGraw-Hill, 2006); and *Remington: The Science and Practice of Pharmacy,* $22^{nd}$ Edition, (Pharmaceutical Press, London, 2012)).

As used herein, the terms "recipient," "individual," "subject," "host," and "patient" are used interchangeably and refer to any mammalian subject for whom diagnosis, treatment, or therapy is desired (e.g., humans). "Mammal" for purposes of treatment refers to any animal classified as a mammal, including humans, domestic and farm animals, and zoo, sports, or pet animals, such as dogs, horses, cats, cows, sheep, goats, pigs, camels, etc. In certain embodiments, the mammal is human.

The phrase "synergistic adjuvant" or "synergistic combination" in the context of this invention includes the combination of two immune modulators such as a receptor agonist, cytokine, and adjuvant polypeptide, that in combination elicit a synergistic effect on immunity relative to either administered alone. Particularly, the immunoconjugates disclosed herein comprise synergistic combinations of the claimed adjuvant and antibody construct. These synergistic combinations upon administration elicit a greater effect on immunity, e.g., relative to when the antibody construct or adjuvant is administered in the absence of the other moiety. Further, a decreased amount of the immunoconjugate may be administered (as measured by the total number of antibody constructs or the total number of adjuvants administered as part of the immunoconjugate) compared to when either the antibody construct or adjuvant is administered alone.

As used herein, the term "administering" refers to parenteral, intravenous, intraperitoneal, intramuscular, intratumoral, intralesional, intranasal, or subcutaneous administration, oral administration, administration as a suppository, topical contact, intrathecal administration, or the implantation of a slow-release device, e.g., a mini-osmotic pump, to the subject.

The terms "about" and "around," as used herein to modify a numerical value, indicate a close range surrounding the numerical value. Thus, if "X" is the value, "about X" or "around X" indicates a value of from 0.9X to 1.1X, e.g., from 0.95X to 1.05X or from 0.99X to 1.01X. A reference to "about X" or "around X" specifically indicates at least the values X, 0.95X, 0.96X, 0.97X, 0.98X, 0.99X, 1.01X, 1.02X, 1.03X, 1.04X, and 1.05X. Accordingly, "about X" and "around X" are intended to teach and provide written description support for a claim limitation of, e.g., "0.98X."

Antibody Adjuvant Conjugates

The invention provides an immunoconjugate of formula:

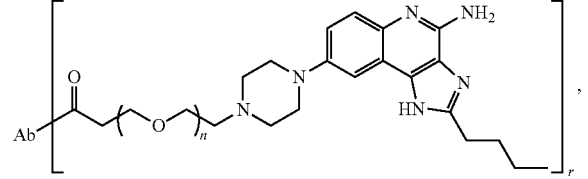

or pharmaceutically acceptable salt thereof, wherein subscript r is an integer from 1 to 10, subscript n is an integer from about 2 to about 25 (e.g., about 2 to about 16, about 6 to about 25, about 6 to about 16, about 8 to about 25, about 8 to about 16, about 6 to about 12, or about 8 to about 12), and "Ab" is an antibody construct that has an antigen binding domain that binds human epidermal growth factor receptor 2 ("HER2"). "Ab" can be any suitable antibody construct that has an antigen binding domain that binds HER2, such as, for example, trastuzumab and pertuzumab. In certain embodiments, "Ab" is trastuzumab (also known as HERCEPTIN™), a biosimilar thereof, or a biobetter thereof. For example, "Ab" can be MYL-14010, ABP 980, BCD-022, CT-P6, EG12014, HD201, ONS-1050, PF-05280014, Ontruzant, Saiputing, Herzuma, or HLX02. In preferred embodiments, "Ab" is trastuzumab (also known as HERCEPTIN™).

Generally, the immunoconjugates of the invention comprise about 1 to about 10 adjuvants, each adjuvant linked via a PEG linker to the antibody construct, as designated with subscript "r." Each of the adjuvants linked via a PEG linker to the antibody construct is conjugated to the antibody construct at an amine of a lysine residue of the antibody construct. In an embodiment, r is 1, such that there is a single adjuvant linked via a PEG linker to the antibody construct. In some embodiments, r is an integer from about 2 to about 10 (e.g., about 2 to about 9, about 3 to about 9, about 4 to about 9, about 5 to about 9, about 6 to about 9, about 3 to about 8, about 3 to about 7, about 3 to about 6, about 4 to about 8, about 4 to about 7, about 4 to about 6, about 5 to about 6, about 1 to about 6, about 1 to about 4, about 2 to about 4, or about 1 to about 3). Accordingly, the immunoconjugates can have (i.e., subscript "r" can be) 1, 2, 3, 4, 5, 6, 7, 8, 9, or 10 adjuvants linked via a PEG linker. In preferred embodiments, the immunoconjugates have (i.e., subscript "r" can be) 1, 2, 3, or 4 adjuvants linked via a PEG linker. The desirable adjuvant to antibody construct ratio (i.e., the value of the subscript "r") can be determined by a skilled artisan depending on the desired effect of the treatment.

Generally, the immunoconjugates of the invention comprise about 2 to about 25 (e.g., about 2 to about 16, about 6 to about 25, about 6 to about 16, about 8 to about 25, about 8 to about 16, about 6 to about 12, or about 8 to about 12) ethylene glycol units, as designated with subscript "n." Accordingly, the immunoconjugates of the invention can comprise at least 2 ethylene glycol groups (e.g., at least 3 ethylene glycol groups, at least 4 ethylene glycol groups, at least 5 ethylene glycol groups, at least 6 ethylene glycol groups, at least 7 ethylene glycol groups, at least 8 ethylene glycol groups, at least 9 ethylene glycol groups, or at least 10 ethylene glycol groups). Accordingly, the immunoconjugate can comprise from about 2 to about 25 ethylene glycol units, for example, from about 6 to about 25 ethylene glycol units, from about 6 to about 16 ethylene glycol units, from about 8 to about 25 ethylene glycol units, from about 8 to about 16 ethylene glycol units, from about 8 to about 12 ethylene glycol units, or from about 8 to about 12 ethylene glycol units. In certain embodiments, the immunoconjugate comprises a di(ethylene glycol) group, a tri(ethylene glycol) group, a tetra(ethylene glycol) group, 5 ethylene glycol groups, 6 ethylene glycol groups, 7 ethylene glycol groups, 8 ethylene glycol groups, 9 ethylene glycol groups, 10 ethylene glycol groups, 11 ethylene glycol groups, 12 ethylene glycol groups, 13 ethylene glycol groups, 14 ethylene glycol groups, 15 ethylene glycol groups, 16 ethylene glycol groups, 24 ethylene glycol groups, or 25 ethylene glycol groups. In preferred embodiments, the immunoconjugate comprises 6 ethylene glycol groups, 8 ethylene glycol groups, 10 ethylene glycol groups, or 12 ethylene glycol groups (i.e., about 6 ethylene glycol groups to about 12 ethylene glycol groups).

The PEG linker can be linked to the antibody construct that has an antigen binding domain that binds HER2 (e.g., trastuzumab, pertuzumab, biosimilars thereof, and biobetters thereof) via an amine of a lysine residue of the antibody construct. Accordingly, the immunoconjugates of the invention can be represented by the following formula:

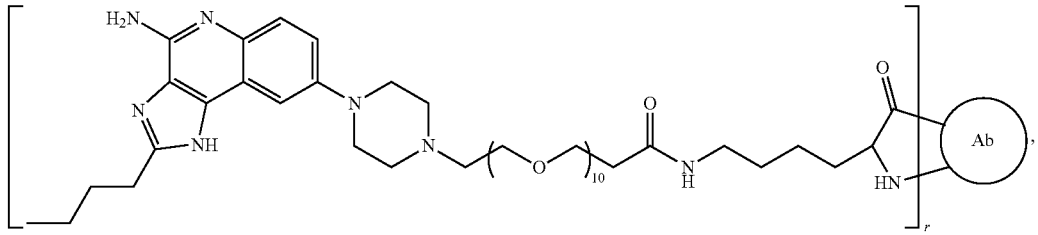

wherein

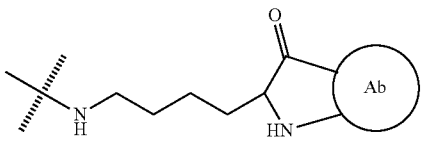

is an antibody construct that has an antigen binding domain that binds HER2 with residue

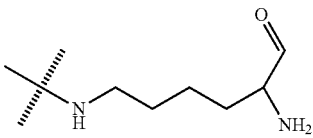

representing a lysine residue of the antibody construct, wherein " ⌇ " represents a point of attachment to the linker.

The adjuvant can be linked via the PEG linker to any suitable residue of the antibody construct, but desirably is linked to any lysine residue of the antibody construct. For example, the adjuvant can be linked via the PEG linker to one or more of K103, K107, K149, K169, K183, and/or K188 of the light chain of the antibody construct, as numbered using the Kabat numbering system. Alternatively, or additionally, the adjuvant can be linked via the PEG linker to one or more of K30, K43, K65, K76, K136, K216, K217, K225, K293, K320, K323, K337, K395, and/or K417 of the heavy chain of the antibody construct, as numbered using the Kabat numbering system. Generally, the adjuvant is predominantly linked via the PEG linker at K107 or K188 of the light chain of the antibody construct, or K30, K43, K65, or K417 of the heavy chain of the antibody construct. In certain embodiments, the adjuvant is linked via the PEG linker at K188 of the light chain of the antibody construct, and optionally one or more other lysine residues of the antibody construct.

Immunoconjugates as described herein can provide an unexpectedly increased activation response of an antigen presenting cell ("APC"). This increased activation can be detected in vitro or in vivo. In some embodiments, the increased APC activation can be detected in the form of a reduced time to achieve a specified level of APC activation. For example, in an in vitro assay, % APC activation can be achieved at an equivalent dose with an immunoconjugate within about 1%, about 10%, about 20%, about 30%, about 40%, or about 50% of the time required to obtain the same or similar percentage of APC activation with a mixture of unconjugated antibody construct and adjuvant, under otherwise identical concentrations and conditions. In some embodiments, an immunoconjugate can activate APCs (e.g., dendritic cells) and/or NK cells in a reduced amount of time. For example, in some embodiments, a mixture of unconjugated antibody construct and adjuvant can activate APCs (e.g., dendritic cells) and/or NK cells and/or induce dendritic cell differentiation after incubation with the mixture for 2, 3, 4, 5, 1-5, 2-5, 3-5, or 4-7 days, while, in contrast, immunoconjugates described herein can activate and/or induce differentiation within 4 hours, 8 hours, 12 hours, 16 hours, or 1 day, under otherwise identical concentrations and conditions. Alternatively, the increased APC activation can be detected in the form of a reduced concentration of immunoconjugate required to achieve an amount (e.g., percent APCs), level (e.g., as measured by a level of upregulation of a suitable marker) or rate (e.g., as detected by a time of incubation required to activate) of APC activation.

In some embodiments, the immunoconjugates of the invention provide more than an about 5% increase in activity compared to a mixture of unconjugated antibody construct and adjuvant, under otherwise identical conditions. In other embodiments, the immunoconjugates of the invention provide more than an about 10%, about 15%, about 20%, about 25%, about 30%, about 35%, about 40%, about 45%, about 50%, about 55%, about 60%, about 65%, or about 70% increase in activity compared to a mixture of unconjugated antibody construct and adjuvant, under otherwise identical conditions. The increase in activity can be assessed by any suitable means, many of which are known to those ordinarily skilled in the art and can include myeloid activation, assessment by cytokine secretion, or a combination thereof.

In some embodiments, the invention provides an immunoconjugate of formula:

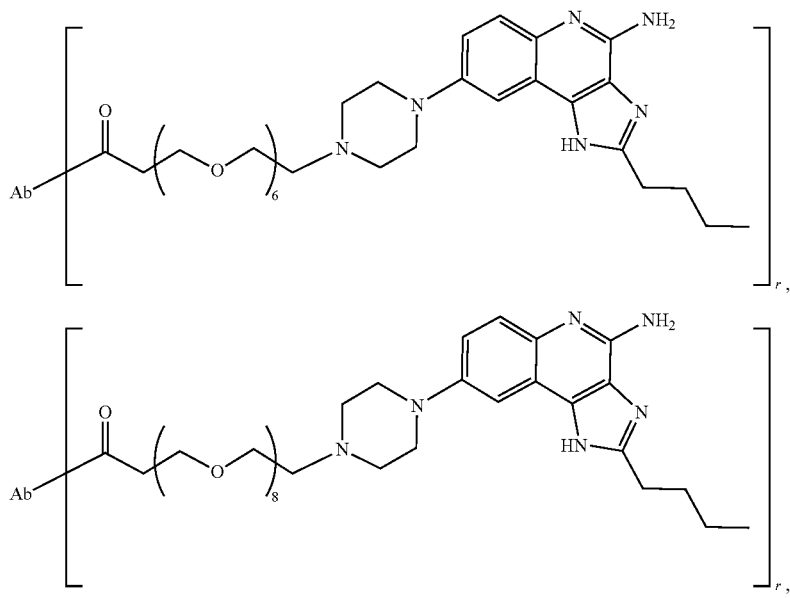

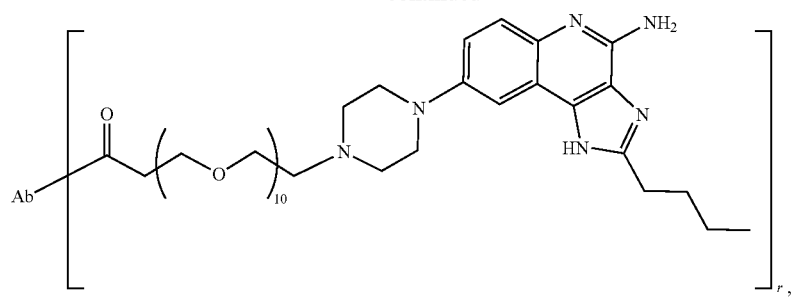
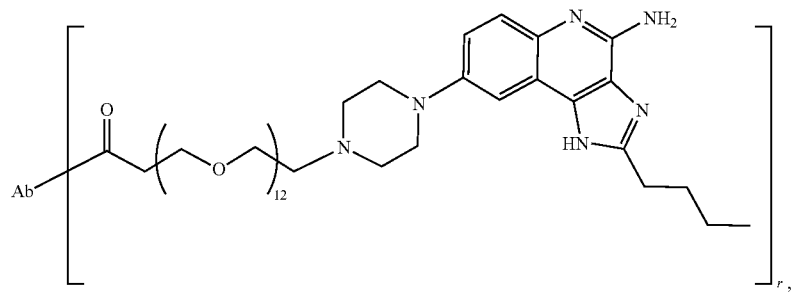
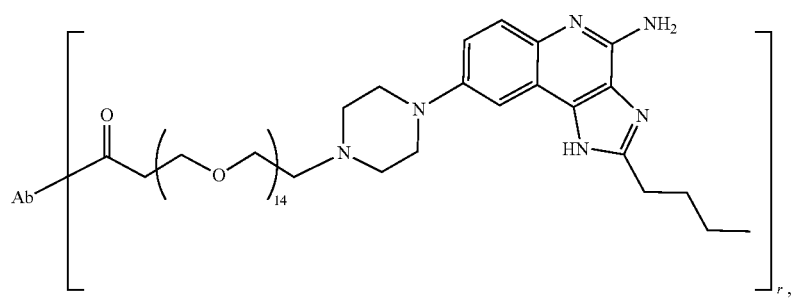
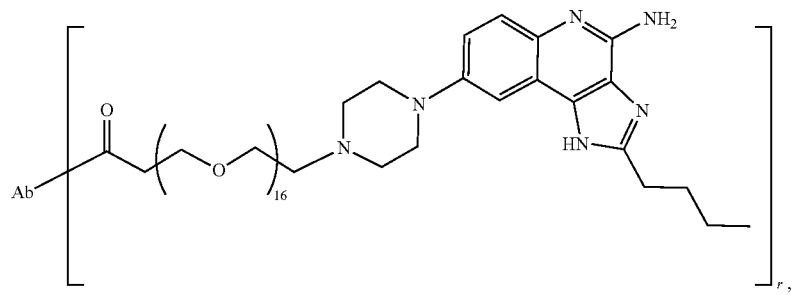
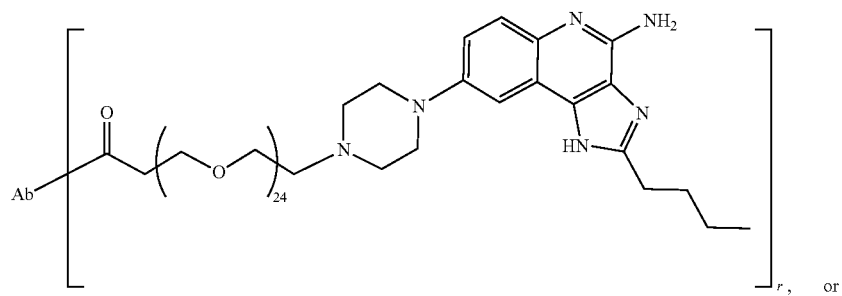

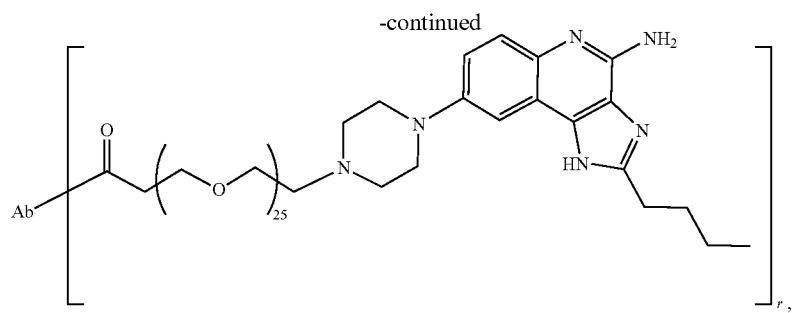
or pharmaceutically acceptable salt thereof, wherein subscript r is an integer from 1 to 10 and "Ab" is an antibody construct that has an antigen binding domain that binds human epidermal growth factor receptor 2 ("HER2").
In certain embodiments, the invention provides an immunoconjugate of formula:
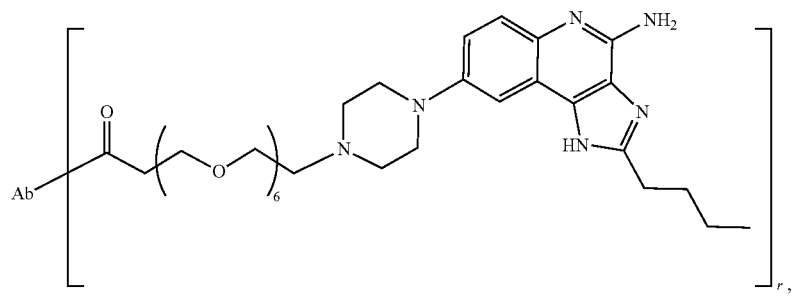
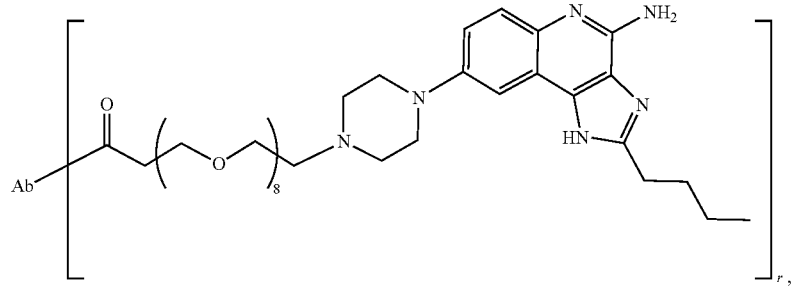
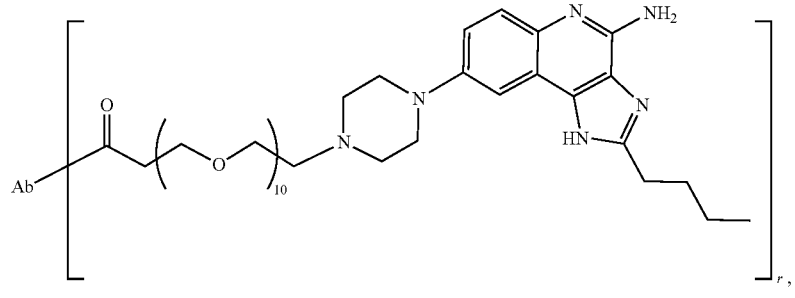
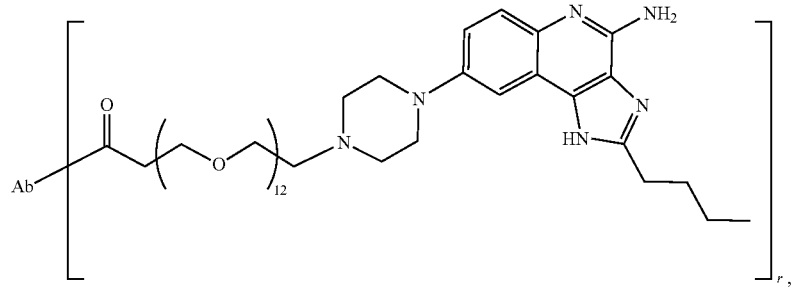

-continued
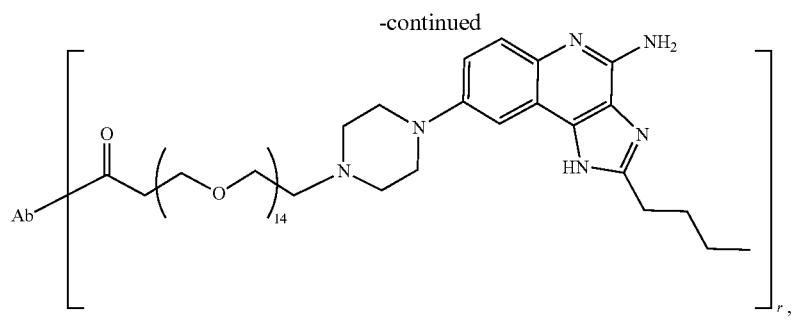
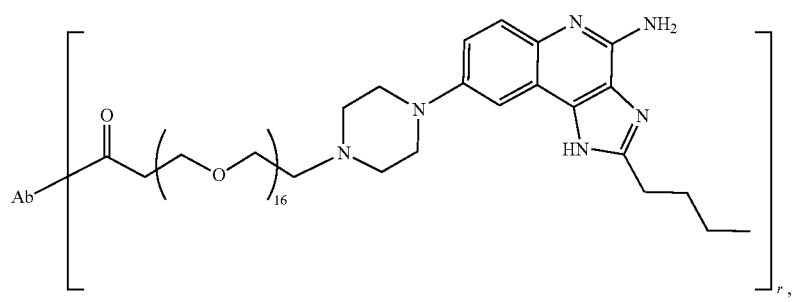
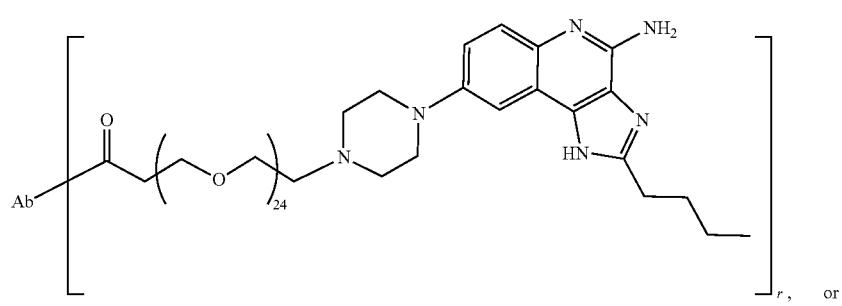
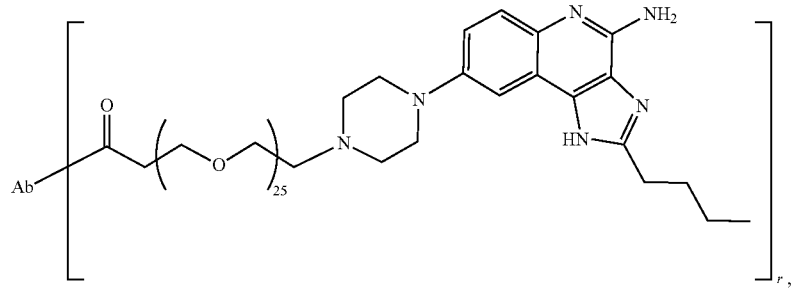
or pharmaceutically acceptable salt thereof, wherein subscript r is an integer from 1 to 10 and "Ab" is trastuzumab (also known as HERCEPTIN™), pertuzumab, biosimilars thereof, and biobetters thereof. For example, "Ab" can be MYL-14010, ABP 980, BCD-022, CT-P6, EG12014, HD201, ONS-1050, PF-05280014, Ontruzant, Saiputing, Herzuma, or HLX02.

In preferred embodiments, the invention provides an immunoconjugate of formula:
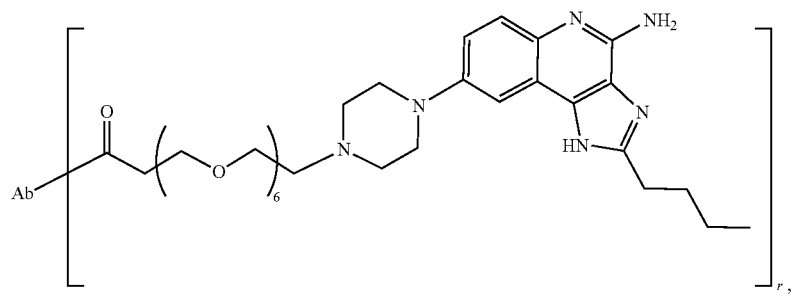
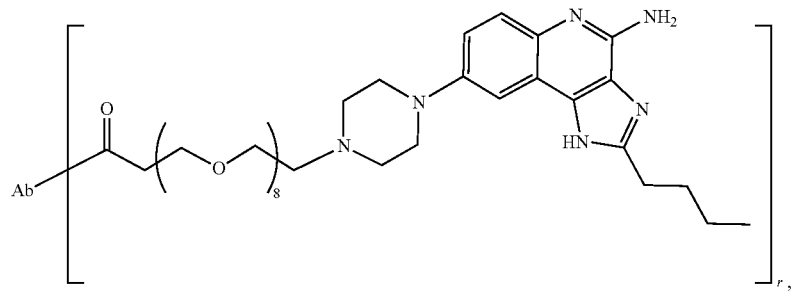
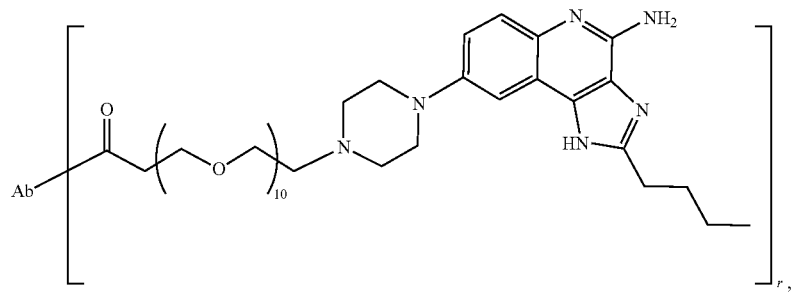
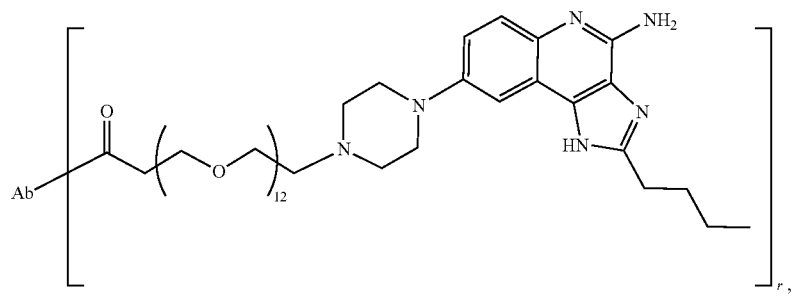
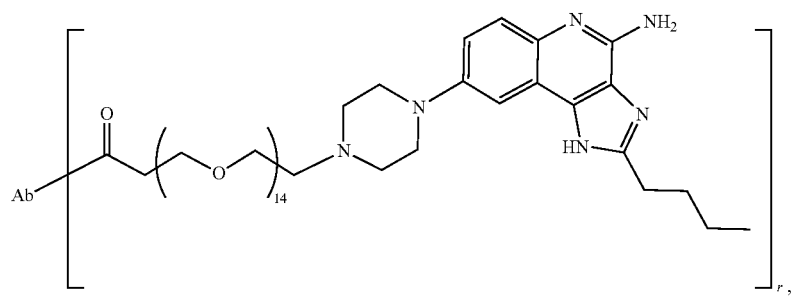

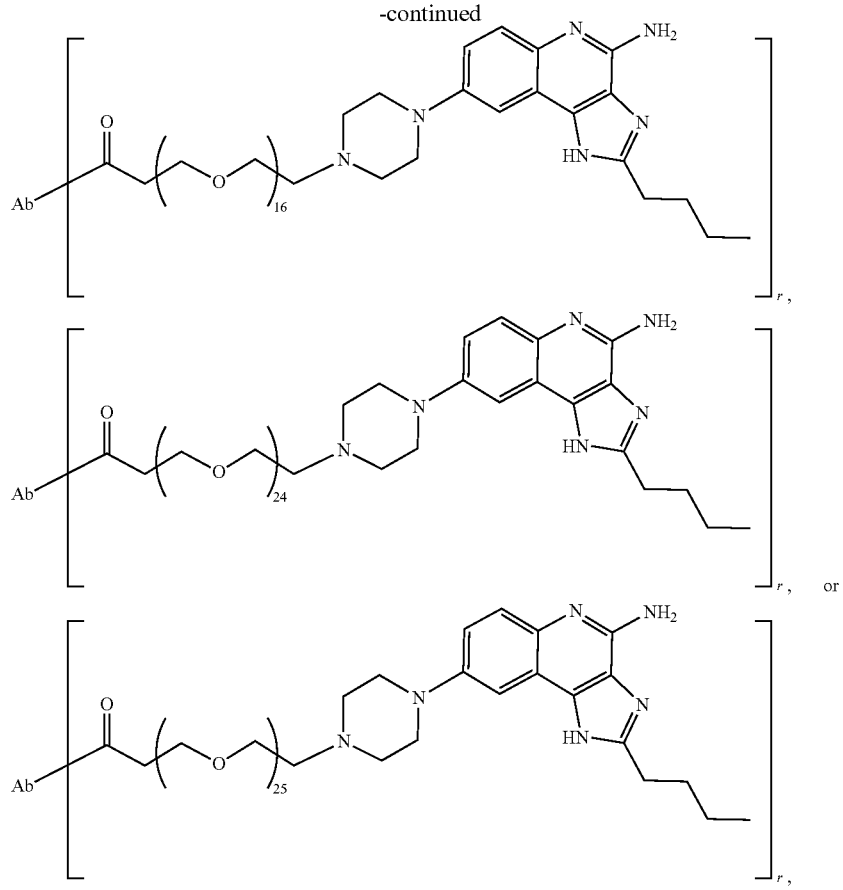

or pharmaceutically acceptable salt thereof, wherein subscript r is an integer from 1 to 10 and "Ab" is trastuzumab (also known as HERCEPTIN™).

Adjuvants

The immunoconjugate of the invention comprises an adjuvant moiety of formula:

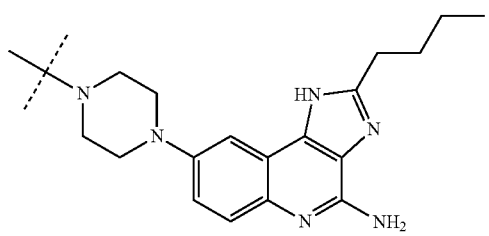

wherein the dashed line (" ") represents a point of attachment of the adjuvant moiety to the linker.

The adjuvant moiety described herein is a TLR agonist.

Antigen Binding Domain and Fc Domain

The immunoconjugates of the invention comprise an antibody construct that comprises an antigen binding domain that binds HER2. In some embodiments, the antibody construct further comprises an Fc domain. In certain embodiments, the antibody construct is an antibody. In certain embodiments, the antibody construct is a fusion protein.

The antigen binding domain can be a single-chain variable region fragment (scFv). A single-chain variable region fragment (scFv), which is a truncated Fab fragment including the variable (V) domain of an antibody heavy chain linked to a V domain of a light antibody chain via a synthetic peptide, can be generated using routine recombinant DNA technology techniques. Similarly, disulfide-stabilized variable region fragments (dsFv) can be prepared by recombinant DNA technology.

An embodiment of the invention provides antibody construct or antigen binding domain which specifically recognizes and binds to HER2 (SEQ ID NO: 1). The antibody construct or antigen binding domain may comprise one or more variable regions (e.g., two variable regions) of an antigen binding domain of an anti-HER2 antibody, each variable region comprising a CDR1, a CDR2, and a CDR3.

An embodiment of the invention provides an antibody construct or antigen binding domain comprising the CDR regions of trastuzumab. In this regard, the antibody construct or antigen binding domain may comprise a first variable region comprising a CDR1 comprising the amino acid sequence of SEQ ID NO: 2 (CDR1 of first variable region), a CDR2 comprising the amino acid sequence of SEQ ID NO: 3 (CDR2 of first variable region), and a CDR3 comprising the amino acid sequence of SEQ ID NO: 4 (CDR3 of first variable region), and a second variable region comprising a CDR1 comprising the amino acid sequence of SEQ ID NO: 5 (CDR1 of second variable region), a CDR2 comprising the amino acid sequence of SEQ ID NO: 6 (CDR2 of second variable region), and a CDR3 comprising the amino acid sequence of SEQ ID NO: 7 (CDR3 of second variable region). In this regard, the antibody construct can comprise (i) all of SEQ ID NOs: 2-4, (ii) all of SEQ ID NOs: 5-7, or (iii) all of SEQ ID NOs: 2-7. Preferably, the antibody construct or antigen binding domain comprises all of SEQ ID NOs: 2-7.

In an embodiment of the invention, the antibody construct or antigen binding domain comprising the CDR regions of trastuzumab further comprises the framework regions of the trastuzumab. In this regard, the antibody construct or antigen binding domain comprising the CDR regions of the trastuzumab further comprises the amino acid sequence of SEQ ID NO: 8 (framework region ("FR") 1 of first variable region), the amino acid sequence of SEQ ID NO: 9 (FR2 of first variable region), the amino acid sequence of SEQ ID NO: 10 (FR3 of first variable region), the amino acid sequence of SEQ ID NO: 11 (FR4 of first variable region), the amino acid sequence of SEQ ID NO: 12 (FR1 of second variable region), the amino acid sequence of SEQ ID NO: 13 (FR2 of second variable region), the amino acid sequence of SEQ ID NO: 14 (FR3 of second variable region), and the amino acid sequence of SEQ ID NO: 15 (FR4 of second variable region). In this regard, the antibody construct or antigen binding domain can comprise (i) all of SEQ ID NOs: 2-4 and 8-11, (ii) all of SEQ ID NOs: 5-7 and 12-15; or (iii) all of SEQ ID NOs: 2-7 and 8-15.

An embodiment of the invention provides an antibody construct or antigen binding domain comprising one or both variable regions of trastuzumab. In this regard, the first variable region may comprise SEQ ID NO: 16. The second variable region may comprise SEQ ID NO: 17. Accordingly, in an embodiment of the invention, the antibody construct or antigen binding domain comprises SEQ ID NO: 16, SEQ ID NO: 17, or both SEQ ID NOs: 16 and 17. Preferably, the polypeptide comprises both of SEQ ID NOs: 16-17.

An embodiment of the invention provides an antibody construct or antigen binding domain comprising the CDR regions of pertuzumab. In this regard, the antibody construct or antigen binding domain may comprise a first variable region comprising a CDR1 comprising the amino acid sequence of SEQ ID NO: 18 (CDR1 of first variable region), a CDR2 comprising the amino acid sequence of SEQ ID NO: 19 (CDR2 of first variable region), and a CDR3 comprising the amino acid sequence of SEQ ID NO: 20 (CDR3 of first variable region), and a second variable region comprising a CDR1 comprising the amino acid sequence of SEQ ID NO: 21 (CDR1 of second variable region), a CDR2 comprising the amino acid sequence of SEQ ID NO: 22 (CDR2 of second variable region), and a CDR3 comprising the amino acid sequence of SEQ ID NO: 23 (CDR3 of second variable region). In this regard, the antibody construct can comprise (i) all of SEQ ID NOs: 18-20, (ii) all of SEQ ID NOs: 21-23, or (iii) all of SEQ ID NOs: 18-23. Preferably, the antibody construct or antigen binding domain comprises all of SEQ ID NOs: 18-23.

In an embodiment of the invention, the antibody construct or antigen binding domain comprising the CDR regions of pertuzumab further comprises the framework regions of the pertuzumab. In this regard, the antibody construct or antigen binding domain comprising the CDR regions of the pertuzumab further comprises the amino acid sequence of SEQ ID NO: 24 (framework region ("FR") 1 of first variable region), the amino acid sequence of SEQ ID NO: 25 (FR2 of first variable region), the amino acid sequence of SEQ ID NO: 26 (FR3 of first variable region), the amino acid sequence of SEQ ID NO: 27 (FR4 of first variable region), the amino acid sequence of SEQ ID NO: 28 (FR1 of second variable region), the amino acid sequence of SEQ ID NO: 29 (FR2 of second variable region), the amino acid sequence of SEQ ID NO: 30 (FR3 of second variable region), and the amino acid sequence of SEQ ID NO: 31 (FR4 of second variable region). In this regard, the antibody construct or antigen binding domain can comprise (i) all of SEQ ID NOs: 18-20 and 24-26, (ii) all of SEQ ID NOs: 21-23 and 27-31; or (iii) all of SEQ ID NOs: 18-21 and 24-31.

An embodiment of the invention provides an antibody construct or antigen binding domain comprising one or both variable regions of pertuzumab. In this regard, the first variable region may comprise SEQ ID NO: 32. The second variable region may comprise SEQ ID NO: 33. Accordingly, in an embodiment of the invention, the antibody construct or antigen binding domain comprises SEQ ID NO: 32, SEQ ID NO: 33, or both SEQ ID NOs: 32 and 33. Preferably, the polypeptide comprises both of SEQ ID NOs: 32-33.

Included in the scope of the embodiments of the invention are functional variants of the antibody constructs or antigen binding domain described herein. The term "functional variant" as used herein refers to an antibody construct having an antigen binding domain with substantial or significant sequence identity or similarity to a parent antibody construct or antigen binding domain, which functional variant retains the biological activity of the antibody construct or antigen binding domain of which it is a variant. Functional variants encompass, for example, those variants of the antibody constructs or antigen binding domain described herein (the parent antibody construct or antigen binding domain) that retain the ability to recognize target cells expressing HER2 to a similar extent, the same extent, or to a higher extent, as the parent antibody construct or antigen binding domain.

In reference to the antibody construct or antigen binding domain, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the antibody construct or antigen binding domain.

A functional variant can, for example, comprise the amino acid sequence of the parent antibody construct or antigen binding domain with at least one conservative amino acid substitution. Alternatively, or additionally, the functional variants can comprise the amino acid sequence of the parent antibody construct or antigen binding domain with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent antibody construct or antigen binding domain.

Amino acid substitutions of the inventive antibody constructs or antigen binding domains are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g., Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The antibody construct or antigen binding domain can consist essentially of the specified amino acid sequence or sequences described herein, such that other components, e.g., other amino acids, do not materially change the biological activity of the antibody construct or antigen binding domain functional variant.

The antibody constructs and antigen binding domains of embodiments of the invention (including functional portions and functional variants) can be of any length, i.e., can comprise any number of amino acids, provided that the antibody constructs (or functional portions or functional variants thereof) retain their biological activity, e.g., the ability to specifically bind to HER2, detect cancer cells in a mammal, or treat or prevent cancer in a mammal, etc. For example, the antibody construct or antigen binding domain can be about 50 to about 5,000 amino acids long, such as 50, 70, 75, 100, 125, 150, 175, 200, 300, 400, 500, 600, 700, 800, 900, 1,000, or more amino acids in length.

The antibody constructs and antigen binding domains of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The antibody constructs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized.

In some embodiments, the antibody construct is a monoclonal antibody of a defined sub-class (e.g., $IgG_1$, $IgG_2$, $IgG_3$, $IgG_4$, $IgA_1$, or $IgA_2$). If combinations of antibodies are used, the antibodies can be from the same subclass or from different subclasses. Typically, the antibody construct is an $IgG_1$ antibody. Various combinations of different subclasses, in different relative proportions, can be obtained by those of skill in the art. In some embodiments, a specific subclass or a specific combination of different subclasses can be particularly effective at cancer treatment or tumor size reduction. Accordingly, some embodiments of the invention provide immunoconjugates wherein the antibody is a monoclonal antibody. In some embodiments, the monoclonal antibody is a humanized monoclonal antibody.

In some embodiments, the antibody construct or antigen binding domain binds to HER2 on a cancer or immune cell at a higher affinity than a corresponding HER2 antigen on a non-cancer cell. For example, the antibody construct or antigen binding domain may preferentially recognize HER2 containing a polymorphism that is found on a cancer or immune cell as compared to recognition of a corresponding wild-type HER2 antigen on the non-cancer. In some embodiments, the antibody construct or antigen binding domain binds a cancer cell with greater avidity than a non-cancer cell. For example, the cancer cell can express a higher density of HER2, thereby providing for a higher affinity binding of a multivalent antibody to the cancer cell.

In some embodiments, the antibody construct or antigen binding domain does not significantly bind non-cancer antigens (e.g., the antibody binds one or more non-cancer antigens with at least 10, 100, 1,000, 10,000, 100,000, or 1,000,000-fold lower affinity (higher Kd) than HER2). In some embodiments, the corresponding non-cancer cell is a cell of the same tissue or origin that is not hyperproliferative or otherwise cancerous. HER2 need not be specific to the cancer cell or even enriched in cancer cells relative to other cells (e.g., HER2 can be expressed by other cells). Thus, in the phrase "an antibody construct that specifically binds to an antigen of a cancer cell," the term "specifically" refers to the specificity of the antibody construct and not to the uniqueness of the presence of HER2 in that particular cell type.

Modified Fc Region

In some embodiments, the antibodies in the immunoconjugates contain a modified Fc region, wherein the modification modulates the binding of the Fc region to one or more Fc receptors.

The terms "Fc receptor" or "FcR" refer to a receptor that binds to the Fc region of an antibody. There are three main classes of Fc receptors: (1) FcγR which bind to IgG, (2) FcαR which binds to IgA, and (3) FcεR which binds to IgE. The FcγR family includes several members, such as FcγI (CD64), FcγRIIA (CD32A), FcγRIIB (CD32B), FcγRIIIA (CD16A), and FcγRIIIB (CD16B). The Fcγ receptors differ in their affinity for IgG and also have different affinities for the IgG subclasses (e.g., IgG1, IgG2, IgG3, and IgG4).

In some embodiments, the antibodies in the immunoconjugates (e.g., antibodies conjugated to at least two adjuvant moieties) contain one or more modifications (e.g., amino acid insertion, deletion, and/or substitution) in the Fc region that results in modulated binding (e.g., increased binding or decreased binding) to one or more Fc receptors (e.g., FcγRI (CD64), FcγRIIA (CD32A), FcγRIIB (CD32B), FcγRIIIA (CD16a), and/or FcγRIIIB (CD16b)) as compared to the native antibody lacking the mutation in the Fc region. In some embodiments, the antibodies in the immunoconjugates contain one or more modifications (e.g., amino acid insertion, deletion, and/or substitution) in the Fc region that reduce the binding of the Fc region of the antibody to FcγRIIB In some embodiments, the antibodies in the immunoconjugates contain one or more modifications (e.g., amino acid insertion, deletion, and/or substitution) in the Fc region of the antibody that reduce the binding of the antibody to FcγRIIB while maintaining the same binding or having increased binding to FcγRI (CD64), FcγRIIA (CD32A), and/or FcRγIIIA (CD16a) as compared to the native antibody lacking the mutation in the Fc region. In some embodiments, the antibodies in the immunoconjugates contain one of more modifications in the Fc region that increase the binding of the Fc region of the antibody to FcγRIIB In some embodiments, the modulated binding is provided by mutations in the Fc region of the antibody relative to the native Fc region of the antibody. The mutations can be in a CH2 domain, a CH3 domain, or a combination thereof. A "native Fc region" is synonymous with a "wild-type Fc region" and comprises an amino acid sequence that is identical to the amino acid sequence of an Fc region found in nature or identical to the amino acid sequence of the Fc region found in the native antibody (e.g., trastuzumab). Native sequence human Fc regions include a native sequence human IgG1 Fc region, native sequence human IgG2 Fc region, native sequence human IgG3 Fc region, and native sequence human IgG4 Fc region, as well as naturally occurring variants thereof. Native sequence Fc includes the various allotypes of Fcs (see, e.g., Jefferis et al., *mAbs*, 1(4): 332-338 (2009)).

In some embodiments, the mutations in the Fc region that result in modulated binding to one or more Fc receptors can include one or more of the following mutations: SD (S239D), SDIE (S239D/I332E), SE (S267E), SELF (S267E/L328F), SDIE (S239D/I332E), SDIEAL (S239D/I332E/A330L), GA (G236A), ALIE (A330L/I332E), GASDALIE (G236A/S239D/A330L/I332E), V9 (G237D/P238D/P271G/A330R), and V11 (G237D/P238D/H268D/P271G/A330R), and/or one or more mutations at the following amino acids: E233, G237, P238, H268, P271, L328 and A330. Additional Fc region modifications for modulating Fc receptor binding are described in, for example, U.S. Patent Application Publication 2016/0145350 and U.S. Pat. Nos. 7,416,726 and 5,624,821, which are hereby incorporated by reference in their entireties.

In some embodiments, the Fc region of the antibodies of the immunoconjugates are modified to have an altered glycosylation pattern of the Fc region compared to the native non-modified Fc region.

Human immunoglobulin is glycosylated at the Asn297 residue in the Cγ2 domain of each heavy chain. This N-linked oligosaccharide is composed of a core heptasaccharide, N-acetylglucosamine4Mannose3 (GlcNAc4Man3). Removal of the heptasaccharide with endoglycosidase or PNGase F is known to lead to conformational changes in the antibody Fc region, which can significantly reduce antibody-binding affinity to activating FcγR and lead to decreased effector function. The core heptasaccharide is often decorated with galactose, bisecting GlcNAc, fucose, or sialic acid, which differentially impacts Fc binding to activating and inhibitory FcγR. Additionally, it has been demonstrated that α2,6-sialyation enhances anti-inflammatory activity in vivo, while defucosylation leads to improved FcγRIIIa binding and a 10-fold increase in antibody-dependent cellular cytotoxicity and antibody-dependent phagocytosis. Specific glycosylation patterns, therefore, can be used to control inflammatory effector functions.

In some embodiments, the modification to alter the glycosylation pattern is a mutation. For example, a substitution at Asn297. In some embodiments, Asn297 is mutated to glutamine (N297Q). Methods for controlling immune response with antibodies that modulate FcγR-regulated signaling are described, for example, in U.S. Pat. No. 7,416,726 and U.S. Patent Application Publications 2007/0014795 and 2008/0286819, which are hereby incorporated by reference in their entireties.

In some embodiments, the antibodies of the immunoconjugates are modified to contain an engineered Fab region with a non-naturally occurring glycosylation pattern. For example, hybridomas can be genetically engineered to secrete afucosylated mAb, desialylated mAb or deglycosylated Fc with specific mutations that enable increased FcRγIIIa binding and effector function. In some embodiments, the antibodies of the immunoconjugates are engineered to be afucosylated.

In some embodiments, the entire Fc region of an antibody construct in the immunoconjugates is exchanged with a different Fc region, so that the Fab region of the antibody is conjugated to a non-native Fc region. For example, the Fab region of trastuzumab, which normally comprises an IgG1 Fc region, can be conjugated to IgG2, IgG3, IgG4, or IgA, or the Fab region of nivolumab, which normally comprises an IgG4 Fc region, can be conjugated to IgG1, IgG2, IgG3, IgA1, or IgG2. In some embodiments, the Fc modified antibody with a non-native Fc domain also comprises one or more amino acid modification, such as the S228P mutation within the IgG4 Fc, that modulate the stability of the Fc domain described. In some embodiments, the Fc modified antibody with a non-native Fc domain also comprises one or more amino acid modifications described herein that modulate Fc binding to FcR.

In some embodiments, the modifications that modulate the binding of the Fc region to FcR do not alter the binding of the Fab region of the antibody to its antigen when compared to the native non-modified antibody. In other embodiments, the modifications that modulate the binding of the Fc region to FcR also increase the binding of the Fab region of the antibody to its antigen when compared to the native non-modified antibody.

Linker

Some of the immunoconjugates disclosed herein can be easier to purify than an immunoconjugate comprising the same adjuvant, the same antibody construct, and a different PEG linker length (e.g., PEG6 to PEG12 vs. PEG2 or PEG25). Without wishing to be bound by any particular theory, it is believed that the PEG6 to PEG12 immunoconjugates described herein provide a good balance of hydrophobicity and hydrophilicity to facilitate the purification process. Some of the immunoconjugates disclosed herein can be easier to solubilize than an immunoconjugate comprising the same adjuvant, the same antibody construct, and a different PEG linker length (e.g., PEG6 to PEG12 vs. PEG2 or PEG25). Without wishing to be bound by any particular theory, it is believed that the PEG6 to PEG12 immunoconjugate described herein provide a good balance of hydrophobicity and hydrophilicity to maintain solubility and be effective under biological conditions. It is also believed that the PEG6 to PEG12 immunoconjugate include a desirable number PEG units to provide enough hydrophobicity to be readily purified and/or isolated, while maintaining enough hydrophilicity to be easily solubilized. In preferred embodiments, the immunoconjugate comprises a PEG10 linker.

Immunoconjugate Composition

The invention provides a composition, e.g., a pharmaceutically acceptable composition or formulation, comprising a plurality of immunoconjugates as described herein and optionally a carrier therefor, e.g., a pharmaceutically acceptable carrier. The immunoconjugates can be the same or different in the composition, i.e., the composition can comprise immunoconjugates that have the same number of adjuvants linked to the same positions on the antibody construct and/or immunoconjugates that have the same number of adjuvants linked to different positions on the antibody construct, that have different numbers of adjuvants linked to the same positions on the antibody construct, or that have different numbers of adjuvants linked to different positions on the antibody construct.

As described herein, the adjuvant can be linked via the PEG linker to any suitable residue of the antibody construct, desirably to a lysine residue of the antibody construct. Thus, for example, the composition can comprise a plurality of immunoconjugates, wherein, for each immunoconjugate, one or more adjuvants are linked via PEG linkers to one or more lysine residues selected from K103, K107, K149, K169, K183, and K188 of the light chain of the antibody construct, and K30, K43, K65, K76, K136, K216, K217, K225, K293, K320, K323, K337, K395, and K417 of the heavy chain of the antibody construct, as numbered using the Kabat numbering system. Without wishing to be bound by any particular theory, the composition generally has a distribution of conjugation sites such that there is an average adjuvant to antibody construct ratio with a given profile of preferred conjugation sites. In some embodiments, at least about 40% (e.g., at least about 50%, at least about 60%, at least about 70%, at least about 80%, or at least about 90%) of the sum total of lysine linkages occur at K188 of the light chain of the antibody construct.

A composition of immunoconjugates of the invention can have an average adjuvant to antibody construct ratio of about 0.4, 0.6, 0.8, 1, 1.2, 1.4, 1.6, 1.8, 2, 2.2, 2.4, 2.6, 2.8, 3, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, or 10, or within a range bounded by any two of the aforementioned values. A skilled artisan will recognize that the number of adjuvant conjugated to the antibody construct may vary from immunoconjugate to immunoconjugate in a composition comprising multiple immunoconjugates of the invention, and, thus, the adjuvant to antibody construct (e.g., antibody) ratio can be measured as an average. The adjuvant to antibody construct (e.g., antibody) ratio can be assessed by any suitable means, many of which are known in the art.

In some embodiments, the composition further comprises one or more pharmaceutically acceptable excipients. For example, the immunoconjugates of the invention can be formulated for parenteral administration, such as IV administration or administration into a body cavity or lumen of an organ. Alternatively, the immunoconjugates can be injected intra-tumorally. Compositions for injection will commonly comprise a solution of the immunoconjugate dissolved in a pharmaceutically acceptable carrier. Among the acceptable vehicles and solvents that can be employed are water and an isotonic solution of one or more salts such as sodium chloride, e.g., Ringer's solution. In addition, sterile fixed oils can conventionally be employed as a solvent or suspending medium. For this purpose, any bland fixed oil can be employed, including synthetic monoglycerides or diglycerides. In addition, fatty acids such as oleic acid can likewise be used in the preparation of injectables. These compositions desirably are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The composition can contain any suitable concentration of the immunoconjugate. The concentration of the immunoconjugate in the composition can vary widely, and will be selected primarily based on fluid volumes, viscosities, body weight, and the like, in accordance with the particular mode of administration selected and the patient's needs. In certain embodiments, the concentration of an immunoconjugate in a solution formulation for injection will range from about 0.1% (w/w) to about 10% (w/w).

Methods of Using the Immunoconjugate

The invention provides a method for treating cancer. The method includes comprising administering a therapeutically effective amount of an immunoconjugate as described herein (e.g., as a composition as described herein) to a subject in need thereof, e.g., a subject that has cancer and is in need of treatment for the cancer.

Trastuzumab and pertuzumab, biosimilars thereof, and biobetters thereof are known to be useful in the treatment of cancer, particularly breast cancer, especially HER2-overexpressing breast cancer, gastric cancer, especially HER2-overexpressing gastric cancer, and gastroesophageal junction adenocarcinoma. The immunoconjugate described herein can be used to treat the same types of cancers as trastuzumab, pertuzumab, biosimilars thereof, and biobetters thereof particularly breast cancer, especially HER2-overexpressing breast cancer, gastric cancer, especially HER2-overexpressing gastric cancer, and gastroesophageal junction adenocarcinoma.

The immunoconjugate is administered to a subject in need thereof in any therapeutically effective amount using any suitable dosing regimen, such as the dosing regimens utilized for trastuzumab, pertuzumab, biosimilars thereof, and biobetters thereof. For example, the methods can include administering the immunoconjugate to provide a dose of from about 100 ng/kg to about 50 mg/kg to the subject. The immunoconjugate dose can range from about 5 mg/kg to about 50 mg/kg, from about 10 μg/kg to about 5 mg/kg, or from about 100 μg/kg to about 1 mg/kg. The immunoconjugate dose can be about 100, 200, 300, 400, or 500 μg/kg. The immunoconjugate dose can be about 1, 2, 3, 4, 5, 6, 7, 8, 9, or 10 mg/kg. The immunoconjugate dose can also be outside of these ranges, depending on the particular conjugate as well as the type and severity of the cancer being treated. Frequency of administration can range from a single dose to multiple doses per week, or more frequently. In some embodiments, the immunoconjugate is administered from about once per month to about five times per week. In some embodiments, the immunoconjugate is administered once per week.

In another aspect, the invention provides a method for preventing cancer. The method comprises administering a therapeutically effective amount of an immunoconjugate (e.g., as a composition as described above) to a subject. In certain embodiments, the subject is susceptible to a certain cancer to be prevented. For example, the methods can include administering the immunoconjugate to provide a dose of from about 100 ng/kg to about 50 mg/kg to the subject. The immunoconjugate dose can range from about 5 mg/kg to about 50 mg/kg, from about 10 μg/kg to about 5 mg/kg, or from about 100 μg/kg to about 1 mg/kg. The immunoconjugate dose can be about 100, 200, 300, 400, or 500 μg/kg. The immunoconjugate dose can be about 1, 2, 3, 4, 5, 6, 7, 8, 9, or 10 mg/kg. The immunoconjugate dose can also be outside of these ranges, depending on the particular conjugate as well as the type and severity of the cancer being treated. Frequency of administration can range from a single dose to multiple doses per week, or more frequently. In some embodiments, the immunoconjugate is administered from about once per month to about five times per week. In some embodiments, the immunoconjugate is administered once per week.

Some embodiments of the invention provide methods for treating cancer as described above, wherein the cancer is breast cancer. Breast cancer can originate from different areas in the breast, and a number of different types of breast cancer have been characterized. For example, the immunoconjugates of the invention can be used for treating ductal carcinoma in situ; invasive ductal carcinoma (e.g., tubular carcinoma; medullary carcinoma; mucinous carcinoma; papillary carcinoma; or cribriform carcinoma of the breast); lobular carcinoma in situ; invasive lobular carcinoma; inflammatory breast cancer; and other forms of breast cancer. In some embodiments, methods for treating breast cancer include administering an immunoconjugate containing an antibody construct that is capable of binding HER2 (e.g., trastuzumab, pertuzumab, biosimilars thereof, and biobetters thereof).

Some embodiments of the invention provide methods for treating cancer as described above, wherein the cancer is gastric cancer. Gastric (stomach) cancer can originate from different cells in the stomach and several types of gastric cancer have been characterized including adenocarcinoma, carcinoid tumors, squamous cell carcinoma, small cell carcinoma, leiomyosarcoma, and gastrointestinal stromal tumors. In some embodiments, methods for treating gastric cancer include administering an immunoconjugate containing an antibody construct that is capable of binding HER2 (e.g., trastuzumab).

Some embodiments of the invention provide methods for treating cancer as described above, wherein the cancer is gastroesophageal junction carcinoma. This carcinoma occurs in the area where the esophagus meats the stomach. There are three types of gastroesophageal junction carcinoma. In Type 1, the cancer the cancer grows down from above and into the gastroesophageal junction. The normal lining of the lower end of the esophagus is replaced by mutations (also called Barrett's esophagus). In Type 2, the cancer grows at the gastroesophageal junction by itself. In Type 3, the cancer grows up into the gastroesophageal junction from the stomach upwards. In some embodiments, methods for treating gastroesophageal junction carcinoma include administering an immunoconjugate containing an antibody construct that is capable of binding HER2 (e.g., trastuzumab).

In some embodiments, the cancer is susceptible to a pro-inflammatory response induced by TLR7 and/or TLR8.

Examples of Non-Limiting Aspects of the Disclosure

Aspects, including embodiments, of the invention described herein may be beneficial alone or in combination, with one or more other aspects or embodiments. Without limiting the foregoing description, certain non-limiting aspects of the disclosure numbered 1-33 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. An immunoconjugate of formula:

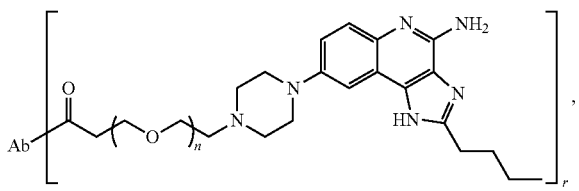

or pharmaceutically acceptable salt thereof, wherein subscript r is an integer from 1 to 10, subscript n is an integer from about 2 to about 25, and "Ab" is an antibody construct that has an antigen binding domain that binds HER2.

2. The immunoconjugate of aspect 1, wherein subscript r is an integer from 1 to 6.

3. The immunoconjugate of aspect 2, wherein subscript r is an integer from 1 to 4.

4. The immunoconjugate of aspect 3, wherein subscript r is 1.

5. The immunoconjugate of aspect 3, wherein subscript r is 2.

6. The immunoconjugate of aspect 3, wherein subscript r is 3.

7. The immunoconjugate of aspect 3, wherein subscript r is 4.

8. The immunoconjugate of any one of aspects 1-7, wherein subscript n is an integer from 6 to 12.

9. The immunoconjugate of aspect 8, wherein subscript n is an integer from 8 to 12.

10. The immunoconjugate of aspect 1, wherein the immunoconjugate is of formula:

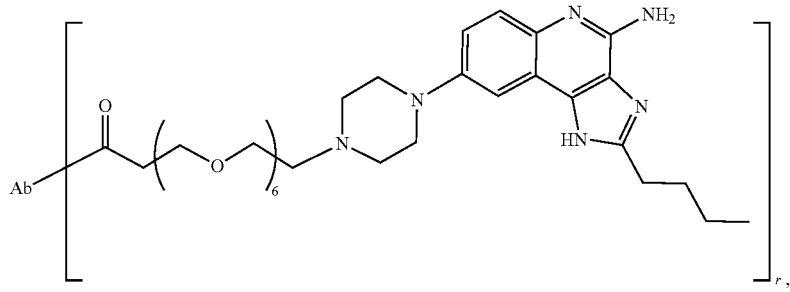

-continued
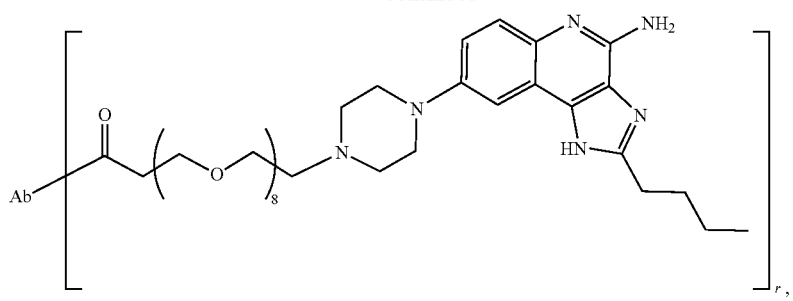
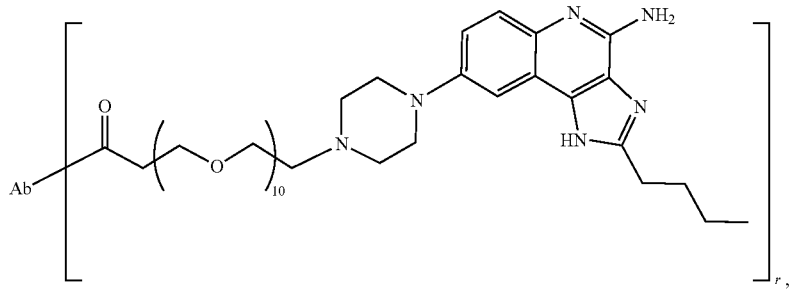
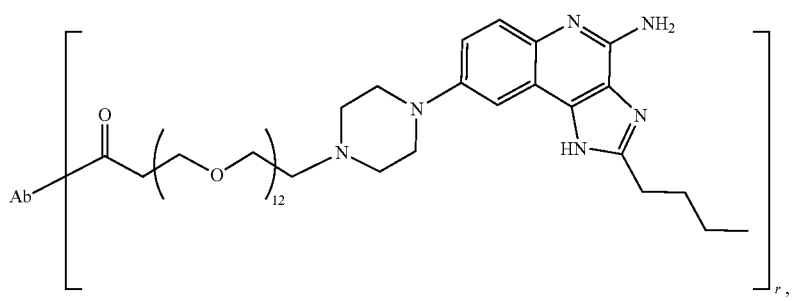
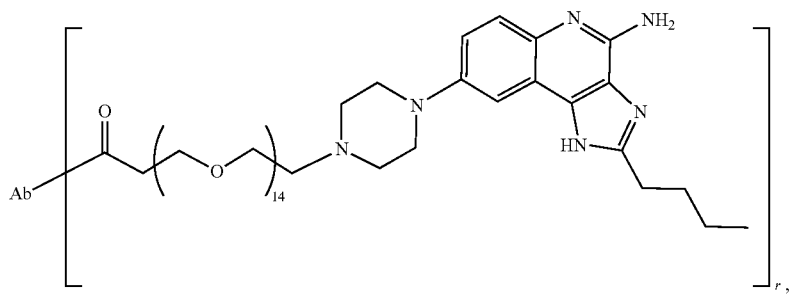
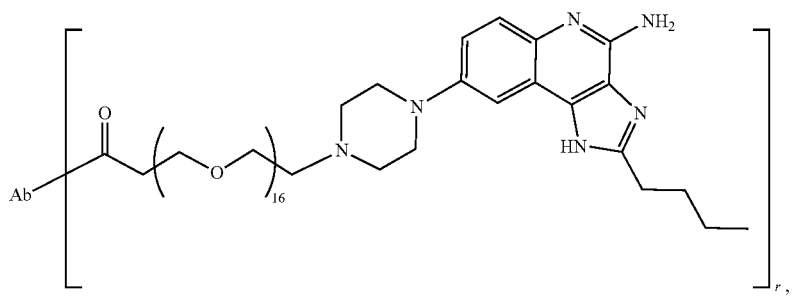

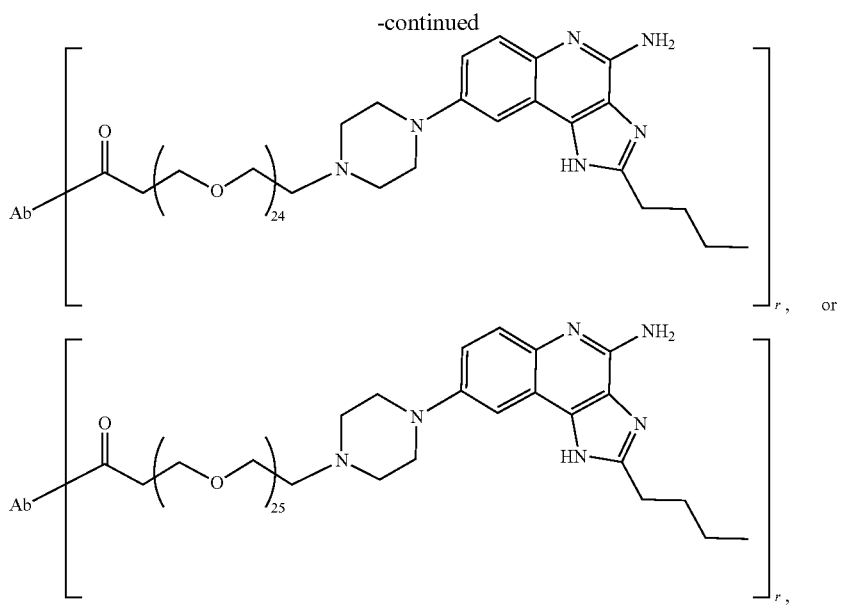

or pharmaceutically acceptable salt thereof, wherein subscript r is an integer from 1 to 10 and "Ab" is an antibody construct that has an antigen binding domain that binds HER2 (e.g., trastuzumab (also known as HERCEPTIN™), a biosimilar thereof, or a biobetter thereof).

11. The immunoconjugate of aspect 1, wherein the immunoconjugate is of formula:

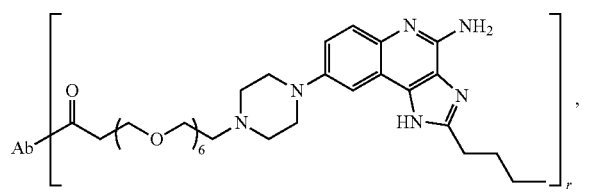

or pharmaceutically acceptable salt thereof, wherein subscript r is an integer from 1 to 10 and "Ab" is an antibody construct that has an antigen binding domain that binds HER2 (e.g., trastuzumab (also known as HERCEPTIN™), a biosimilar thereof, or a biobetter thereof).

12. The immunoconjugate of aspect 1, wherein the immunoconjugate is of formula:

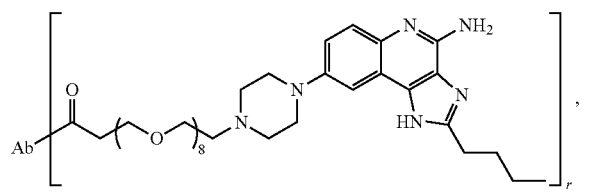

or pharmaceutically acceptable salt thereof, wherein subscript r is an integer from 1 to 10 and "Ab" is an antibody construct that has an antigen binding domain that binds HER2 (e.g., trastuzumab (also known as HERCEPTIN™), a biosimilar thereof, or a biobetter thereof).

13. The immunoconjugate of aspect 1, wherein the immunoconjugate is of formula:

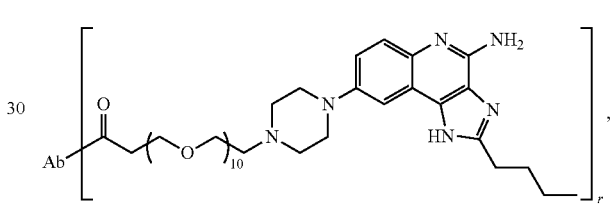

or pharmaceutically acceptable salt thereof, wherein subscript r is an integer from 1 to 10 and "Ab" is an antibody construct that has an antigen binding domain that binds HER2 (e.g., trastuzumab (also known as HERCEPTIN™), a biosimilar thereof, or a biobetter thereof).

14. The immunoconjugate of aspect 1, wherein the immunoconjugate is of formula:

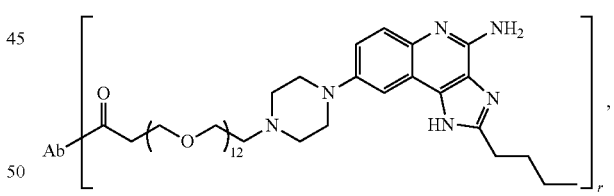

or pharmaceutically acceptable salt thereof, wherein subscript r is an integer from 1 to 10 and "Ab" is an antibody construct that has an antigen binding domain that binds HER2 (e.g., trastuzumab (also known as HERCEPTIN™), a biosimilar thereof, or a biobetter thereof).

15. The immunoconjugate of any one of aspects 1-14, wherein "Ab" is trastuzumab, a biosimilar thereof, or a biobetter thereof.

16. The immunoconjugate of any one of aspects 1-14, wherein "Ab" is pertuzumab, a biosimilar thereof, or a biobetter thereof.

17. The immunoconjugate of aspect 15, wherein "Ab" is trastuzumab.

18. The immunoconjugate of aspect 15, wherein "Ab" is a biosimilar of trastuzumab.

19. A composition comprising a plurality of immunoconjugates according to any one of aspects 1-18.

20. The composition of aspect 19, wherein the average adjuvant to antibody construct ratio is from about 0.01 to about 10.

21. The composition of aspect 20, wherein the average adjuvant to antibody construct ratio is from about 1 to about 10.

22. The composition of aspect 21, wherein the average adjuvant to antibody construct ratio is from about 1 to about 6.

23. The composition of aspect 22, wherein the average adjuvant to antibody construct ratio is from about 1 to about 4.

24. The composition of aspect 23, wherein the average adjuvant to antibody construct ratio is from about 1 to about 3.

25. A method for treating cancer comprising administering a therapeutically effective amount of an immunoconjugate according to any one of aspects 1-18 or a composition according to any one of aspects 19-24 to a subject in need thereof.

26. The method of aspect 25, wherein the cancer is susceptible to a pro-inflammatory response induced by TLR7 and/or TLR8 agonism.

27. The method of aspect 25 or 26, wherein the cancer is a HER2-expressing cancer.

28. The method of any one of aspects 25-27, wherein the cancer is breast cancer.

29. The method of aspect 28, wherein the breast cancer is HER2 overexpressing breast cancer.

30. The method of any one of aspect 25-27, wherein the cancer is gastric cancer.

31. The method of aspect 30, wherein the gastric cancer is HER2 overexpressing gastric cancer.

32. The method of any one of aspect 25-27, 30, or 31, wherein the cancer is gastroesophageal junction adenocarcinoma.

33. Use of an immunoconjugate according to any one of aspect 1-18 or a composition according to any one of aspects 19-24 for treating cancer.

Examples

The following examples further illustrate the invention but, of course, should not be construed as in any way limiting its scope.

Example 1: Synthesis of Compound 2

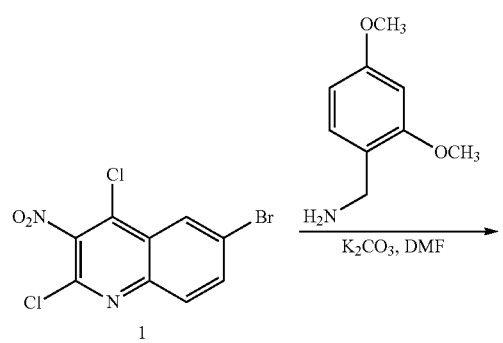

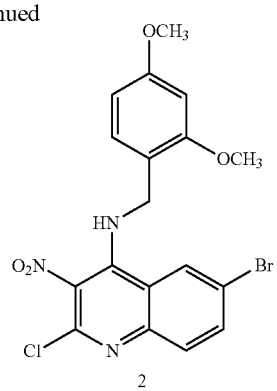

To a solution of 6-bromo-2,4-dichloro-3-nitroquinoline (5.6 g, 17.4 mmol, 1 eq.) and solid K$_2$CO$_3$ (3.6 g, 26 mmol, 1.5 eq.) in dimethylformamide (DMF, 100 mL) at room temperature was added neat 2,4-dimethoxybenzylamine (3.5 g, 20.1 mmol, 1.2 eq.). The mixture was stirred for 15 minutes, water (300 mL) was added, and then the mixture was stirred for 5 minutes. The resultant solid was filtered and then dissolved in ethyl acetate (100 mL). The solution was washed with water (100 mL), brine (100 mL), separated, dried (Na$_2$SO$_4$), then filtered and concentrated in vacuo. The brown solid was triturated with 1:1 hexanes/diethyl ether (150 mL) and filtered to obtain 6-bromo-2-chloro-4-(2,4-dimethoxybenzyl)amino-3-nitroquinoline (6.9 g, 15.3 mmol, 88%) as a yellow solid. The compound was used without further purification.

Example 2: Synthesis of Compound 3

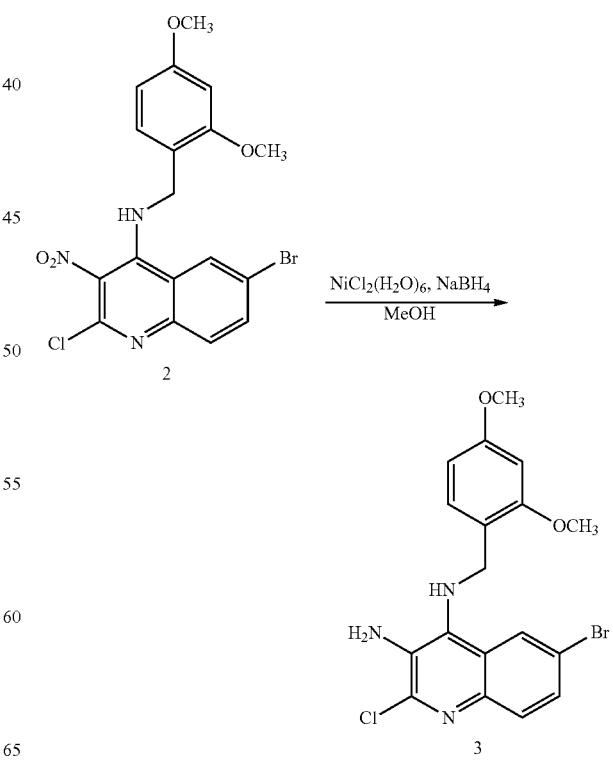

NiCl$_2$·6H$_2$O (0.36 g, 1.5 mmol, 0.1 eq.) was added to 6-bromo-2-chloro-4-(2,4-dimethoxybenzyl)amino-3-nitroquinoline (6.9 g, 15.3 mmol, 88%) in methanol (200 mL) at 0° C. Sodium borohydride (pellets, 1.42 g, 38 mmol, 2.5 eq.) was added and the reaction was stirred for 1 h at 0° C. then warmed to room temperature and stirred for another 15 minutes. Glacial acetic acid (5 mL) was added until a pH of ~5 was obtained. The solvent was evaporated in vacuo and the crude solid was re-dissolved in ethyl acetate (150 mL) then filtered through a bed of diatomaceous earth to remove a black insoluble material. The ethyl acetate was removed in vacuo. The dark brown solid was triturated with ether (75 mL) then filtered to obtain 3-amino-6-bromo-2-chloro-4-(2,4-dimethoxybenzyl)aminoquinoline (5.81 g, 13.7 mmol, 90%) as a tan solid. The compound was used without further purification.

Example 3: Synthesis of Compound 4

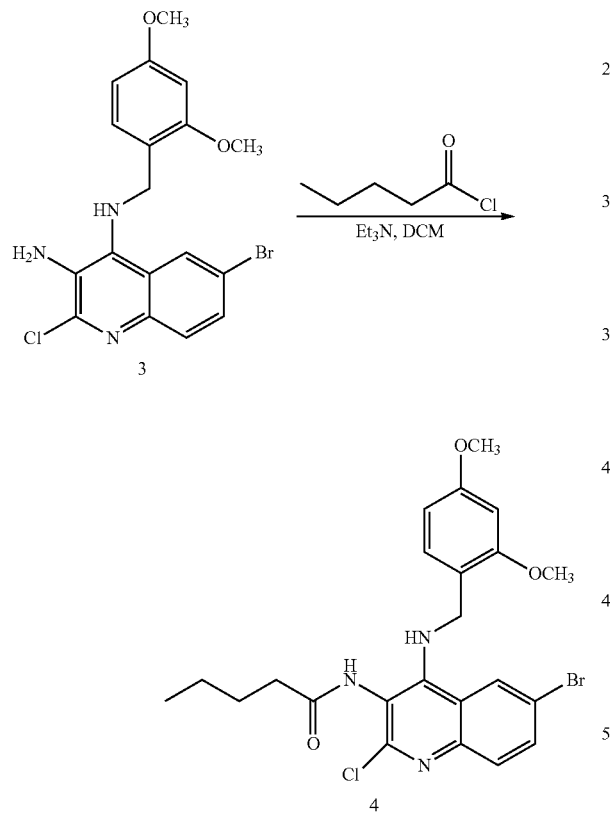

Neat valeroyl chloride (2.0 mL, 2.0 g, 16 mmol, 1.2 eq) was added to a solution of 3-amino-6-bromo-2-chloro-4-(2,4-dimethoxybenzyl)aminoquinoline (5.75 g, 13.6 mmol, 1 eq.) in dichloromethane (100 mL) containing triethylamine (2.1 g, 2.8 mL, 20 mmol, 1.5 eq.) while stirred at room temperature. The mixture was washed with water (150 mL), brine (150 mL), separated, then dried (Na$_2$SO$_4$), filtered, and concentrated. The solid was triturated with ether, filtered, and then dried under vacuum. N-(6-bromo-2-chloro-4-((2,4-dimethoxybenzyl)amino)quinolin-3-yl)pentanamide was obtained as a brown solid (5.8 g, 11.4 mmol, 84%). The compound was used without further purification.

Example 4: Synthesis of Compound 5

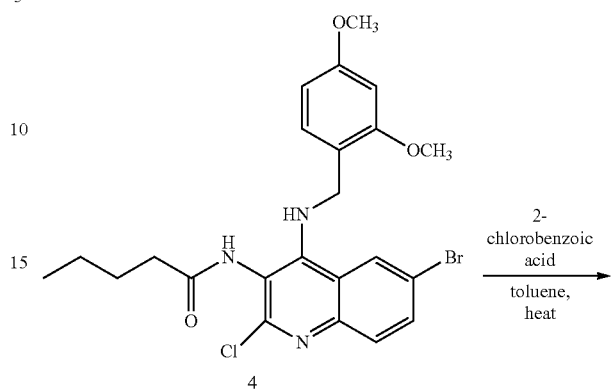

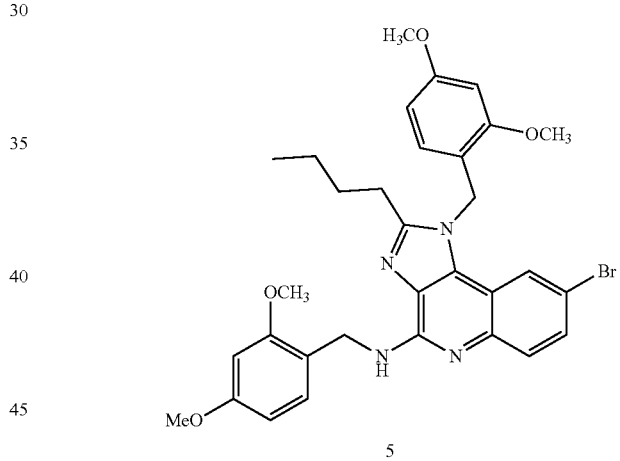

In a 100 mL beaker a mixture of N-(6-bromo-2-chloro-4-((2,4-dimethoxybenzyl)amino)quinolin-3-yl)pentanamide (5.8 g, 11.4 mmol, 1 eq.) and 2-chlorobenzoic (0.90 g, 5.7 mmol. 0.5 eq.) was boiled in 50 mL toluene for 2 hours. Toluene was added to 50 mL each time the volume reached 25 mL. 2,4-dimethoxybenzylamine (9.5 g, 57 mmol, 5 eq.) was added and the reaction was maintained at 120° C. for 2 hours. The reaction was cooled to room temperature and water (80 mL) then acetic acid (3.5 mL) was added. The supernatant was decanted and the crude product was washed with water (80 mL). The wet solid was triturated with methanol (100 mL) to provide 8-bromo-2-butyl-N,1-bis(2,4-dimethoxybenzyl)-1H-imidazo[4,5-c]quinolin-4-amine (4.80 g, 7.7 mmol, 68%) as an off-white solid. The compound was used without further purification.

Example 5: Synthesis of Compound 6

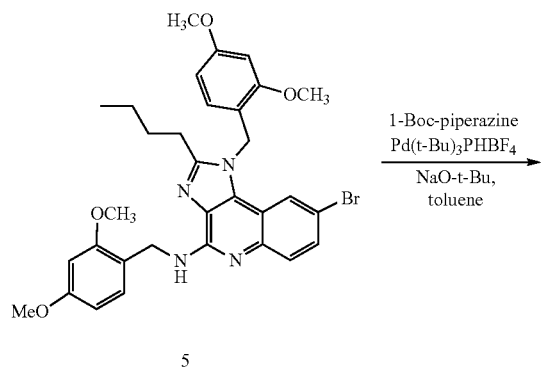

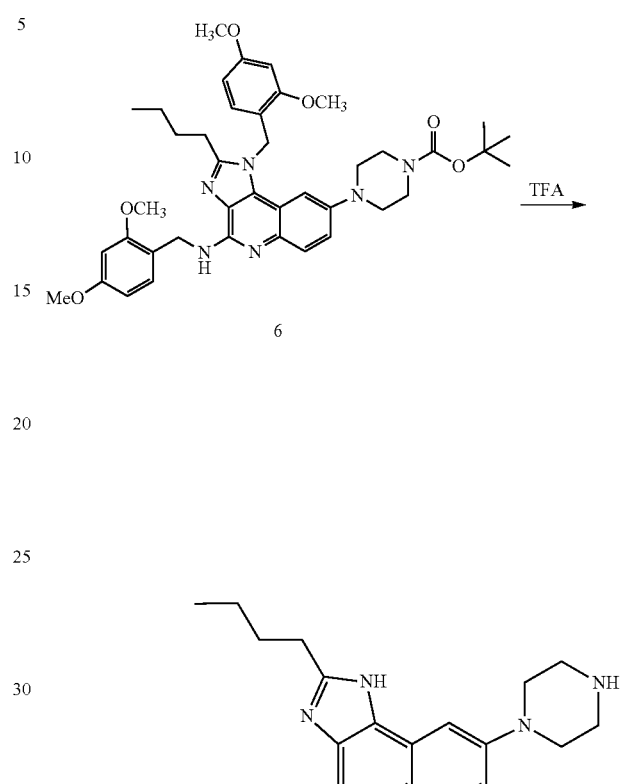

A mixture of 8-bromo-2-butyl-N,1-bis(2,4-dimethoxybenzyl)-1H-imidazo[4,5-c]quinolin-4-amine (0.31 g, 0.5 mmol, 1 eq.) and tert-butyl piperazine-1-carboxylate (0.19 g, 1 mmol, 2 eq.) were combined in toluene (2 mL) then degassed with argon. Pd₂dba₃ (45 mg, 0.05 mmol, 0.1 eq.), tri-tert-butylphosphine tetrafluoroborate (29 mg, 0.10 mmol, 0.2 eq) and sodium tert-butoxide (144 mg, 1.5 mmol, 3 eq) were added. The mixture was heated in a capped vial at 110° C. for 30 minutes. The mixture was cooled then partitioned between ethyl acetate (50 mL) and water (50 mL). The organic layer was washed with brine (50 mL), dried with sodium sulfate, filtered and concentrated in vacuo. The crude product was purified on silica gel (20 g) and then eluted with 50% ethyl acetate/hexanes to yield tert-butyl 4-(2-butyl-1-(2,4-dimethoxybenzyl)-4-((2,4-dimethoxybenzyl)amino)-1H-imidazo[4,5-c]quinolin-8-yl)piperazine-1-carboxylate (0.28 g, 0.39 mmol, 78%) as an off-white solid. LC/MS [M+H] 725.40 (calculated); LC/MS [M+H] 725.67 (observed).

Example 6: Synthesis of Compound 7

Tert-butyl 4-(2-butyl-1-(2,4-dimethoxybenzyl)-4-((2,4-dimethoxybenzyl)amino)-1H-imidazo[4,5-c]quinolin-8-yl)piperazine-1-carboxylate (0.28 g, 0.39 mmol, 1 eq.) was dissolved in TFA (3 mL) and heated to reflux for 5 min. The TFA was removed in vacuo and the crude product was dissolved in acetonitrile, filtered then concentrated to obtain the TFA salt of 2-butyl-8-(piperazin-1-yl)-1H-imidazo[4,5-c]quinolin-4-amine (0.16 g, 0.37 mmol, 95%) as an off-white solid. LC/MS [M+H] 325.21 (calculated); LC/MS [M+H] 325.51 (observed).

Example 7: Synthesis of Compound 8

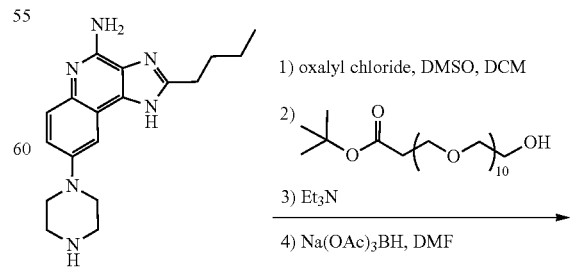

-continued

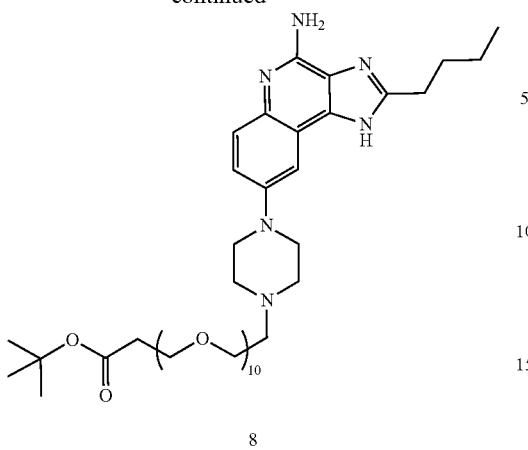

8

Example 8: Synthesis of Compound 9

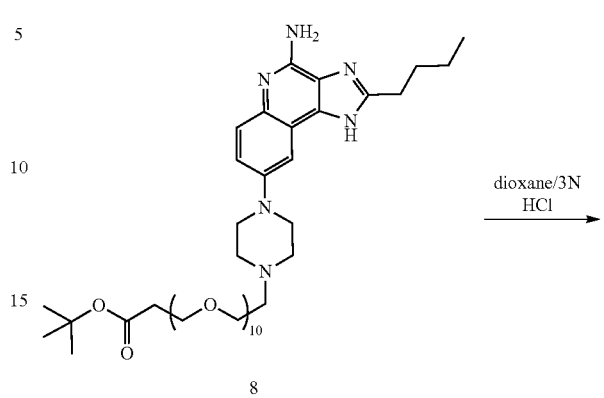

8

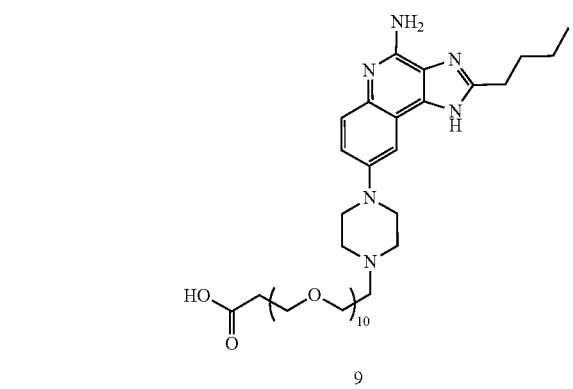

9

In a 40 mL vial flushed with nitrogen, oxalyl chloride (1.84 g, 1.24 mL, 14.5 mmol, 2.5 eq) was added then dichloromethane (10 mL). The solution was cooled to −78° C. A solution of DMSO (2.26 g, 2.05 mL, 29 mmol, 5 eq) in dichloromethane (9 mL) was added dropwise and the mixture was stirred for 15 minutes. A solution of tert-butyl 1-hydroxy-3,6,9,12,15,18,21,24,27,30-decaoxatritriacontan-33-oate (3.4 g, 5.8 mmol, 1 eq) in dichloromethane (9 mL) was added dropwise and the mixture was stirred for 30 minutes at −78° C. Triethylamine (4.4 g, 6.0 mL, 43.5 mmol, 7.5 eq) was added dropwise. This mixture was stirred for 30 min at −78° C. then warmed to room temperature over 30 minutes. To a 100 mL round bottom flask containing 2-butyl-8-(piperazin-1-yl)-1H-imidazo[4,5-c]quinolin-4-amine hydrochloride (2.1 g, 5.8 mmol, 1 eq) and sodium triacetoxyborohydride (5.5 g, 26 mmol, 4.5 eq) in DMF (30 mL) was slowly added tert-butyl 1-oxo-3,6,9,12,15,18,21, 24,27,30-decaoxatritriacontan-33-oate (theoretical amount 5.8 mmol, 1 eq) and the reaction was stirred at room temperature for 1 hour. The dichloromethane was removed under reduced pressure, and then 20% $Na_2CO_3$ (20 mL) was added and the mixture was stirred vigorously for 15 minutes. All of the solvent was removed and the solid material was suspended and sonicated in 10% methanol/dichloromethane, then filtered through diatomaceous earth. The filter cake was washed with 10% methanol/dichloromethane and the combined filtrates were concentrated. Purification by flash chromatography (80 g REDISEP™ gold silica column) was performed using a 2-20% MeOH/dichloromethane+0.1% triethylamine (55 mL/min) gradient over 28 min. The pure fractions were combined and concentrated to obtain tert-butyl 1-(4-(4-amino-2-butyl-1H-imidazo[4,5-c]quinolin-8-yl)piperazin-1-yl)-3,6,9,12,15,18,21,24,27,30-decaoxatritriacontan-33-oate (3.9 g, 4.4 mmol, 75%) as a slightly golden syrup. The impure fractions containing were re-purified then combined to give a final mass (4.26 g, 4.8 mmol, 83%). LC/MS [M+H] 893.55 (calculated); LC/MS [M+H] 893.98 (observed).

Tert-butyl 1-(4-(4-amino-2-butyl-1H-imidazo[4,5-c]quinolin-8-yl)piperazin-1-yl)-3,6,9,12,15,18,21,24,27,30-decaoxatritriacontan-33-oate (4.26 g, 4.8 mmol) was dissolved in a 1:1 mixture of 3 M aq. HCl and dioxane (100 mL) and heated at 60° C. for 60 min. After hydrolysis was complete the solvent was removed under reduced pressure. The 1-(4-(4-amino-2-butyl-1H-imidazo[4,5-c]quinolin-8-yl)piperazin-1-yl)-3,6,9,12,15,18,21,24,27,30-decaoxatritriacontan-33-oic acid hydrochloride obtained was azeotroped 4 times with acetonitrile (75 mL) then suspended in acetonitrile (75 mL) and centrifuged at 4000 rpm for 4 minutes. This process was repeated. The solid was transferred to a 100 mL round bottom flask with acetonitrile and concentrated by under reduced pressure to obtain a yellow, hygroscopic solid (4.0 g, 4.6 mmol, 95%) that was used as is in the next reaction. LC/MS [M+H] 837.49 (calculated); LC/MS [M+H] 837.84 (observed).

Example 9: Synthesis of Compound 10

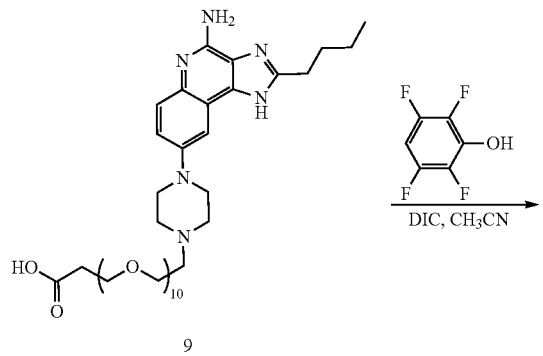

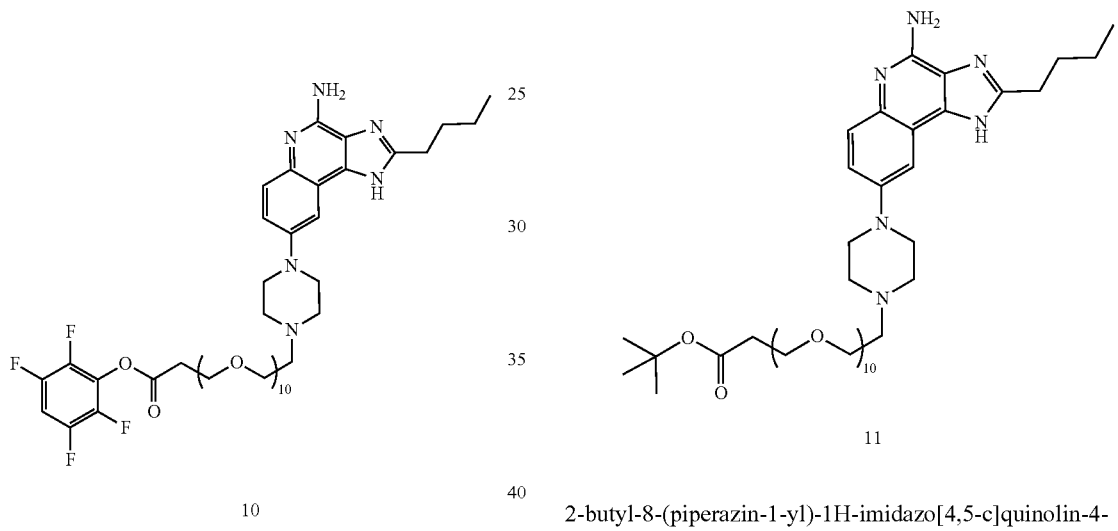

To a 250 mL round bottom flask containing the 1-(4-(4-amino-2-butyl-1H-imidazo[4,5-c]quinolin-8-yl)piperazin-1-yl)-3,6,9,12,15,18,21,24,27,30-decaoxatritriacontan-33-oic acid hydrochloride (4.0 g, 4.6 mmol, 1 eq) was added a suspension of 2,3,5,6-tetrafluorophenol (1.64 g, 10 mmol, 2.4 eq) and EDC (2.0 g, 11 mmol, 2.3 eq.) in anhydrous DMF (50 mL) and the mixture was allowed to stir at room temperature for 30 minutes. The mixture was then heated at 50° C. for 30 minutes. Most of the DMF (~90%) was removed by azeotroping with toluene (80 mL) under reduced pressure with the bath temperature set to 50° C. To this crude material was added diethyl ether (100 mL) and the pasty solid was stirred vigorously. The supernatant was discarded. This process was repeated. The crude material was dissolved in 40 mL ethyl acetate/acetone/acetic acid/water (6:2:1:1). The crude solution was divided into two equal portions and each was purified on a 40 g REDISEP™ gold silica column (Teledyne Isco, Lincoln, Nebr.) using isocratic eluent ethyl acetate/acetone/acetic acid/water (6:2:1:1) to obtain 2,3,5,6-tetrafluorophenyl 1-(4-(4-amino-2-butyl-1H-imidazo[4,5-c]quinolin-8-yl)piperazin-1-yl)-3,6,9,12,15,18,21,24,27,30-decaoxatritriacontan-33-oate (3.34 g, 3.4 mmol, 74%) as an orange paste. LC/MS [M+H] 985.49 (calculated); LC/MS [M+H] 985.71 (observed).

Example 10: Synthesis of Compound 11

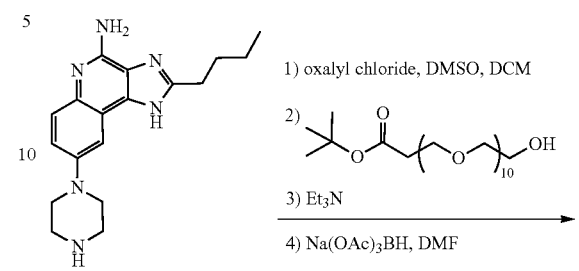

2-butyl-8-(piperazin-1-yl)-1H-imidazo[4,5-c]quinolin-4-amine was converted into tert-butyl 1-(4-(4-amino-2-butyl-1H-imidazo[4,5-c]quinolin-8-yl)piperazin-1-yl)-3,6,9,12,15,18-hexaoxahenicosan-21-oate according to the procedure described in Example 7. LC/MS [M+H] 717.45 (calculated); LC/MS [M+H] 717.75 (observed).

Example 11: Synthesis of Compound 12

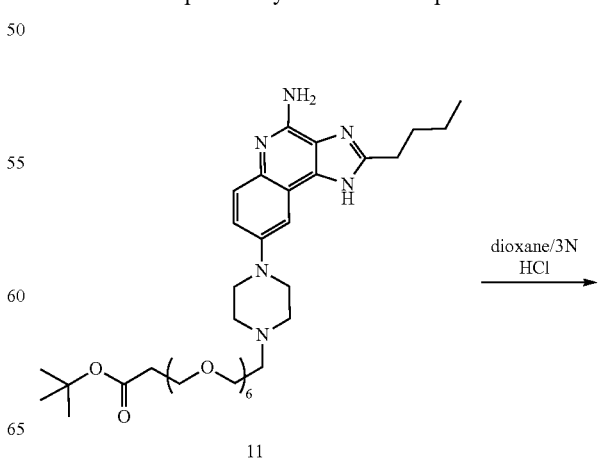

-continued

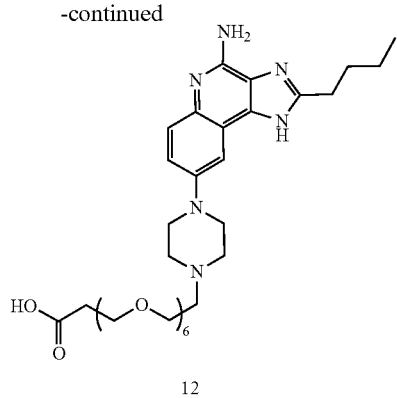

12

Tert-butyl 1-(4-(4-amino-2-butyl-1H-imidazo[4,5-c]quinolin-8-yl)piperazin-1-yl)-3,6,9,12,15,18-hexaoxahenicosan-21-oate was converted into 1-(4-(4-amino-2-butyl-1H-imidazo[4,5-c]quinolin-8-yl)piperazin-1-yl)-3,6,9,12,15,18-hexaoxahenicosan-21-oic acid according to the procedure described in Example 8. LC/MS [M+H] 661.39 (calculated); LC/MS [M+H] 661.60 (observed).

Example 12: Synthesis of Compound 13

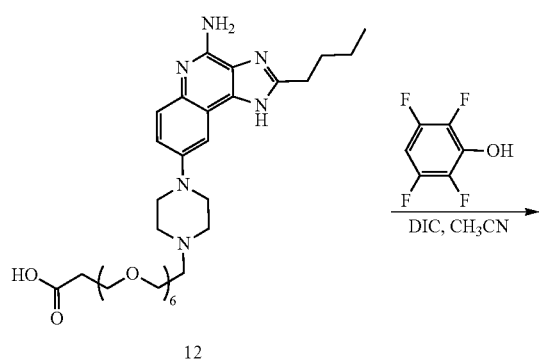

12

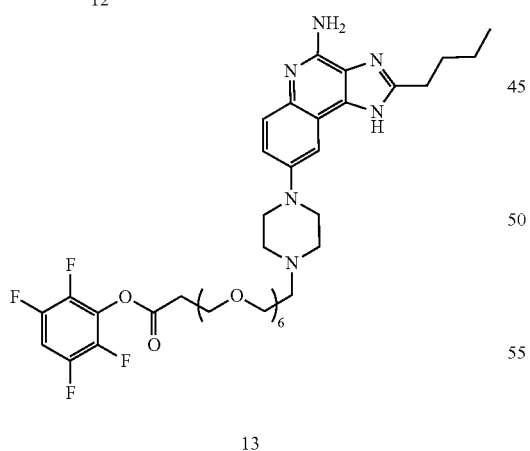

13

1-(4-(4-amino-2-butyl-1H-imidazo[4,5-c]quinolin-8-yl)piperazin-1-yl)-3,6,9,12,15,18-hexaoxahenicosan-21-oic acid was converted into 2,3,5,6-tetrafluorophenyl 1-(4-(4-amino-2-butyl-1H-imidazo[4,5-c]quinolin-8-yl)piperazin-1-yl)-3,6,9,12,15,18-hexaoxahenicosan-21-oate according to the procedure described in Example 9. LC/MS [M+H] 809.39 (calculated); LC/MS [M+H] 809.62 (observed).

Example 13: Synthesis of Compound 14

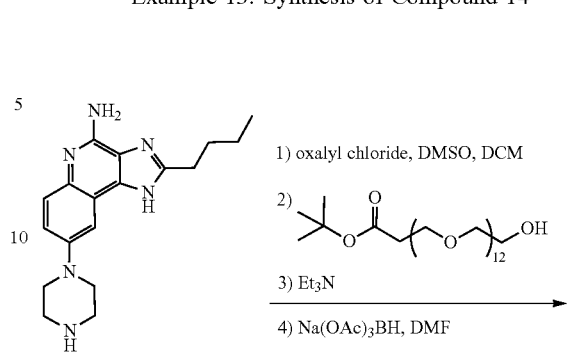

7

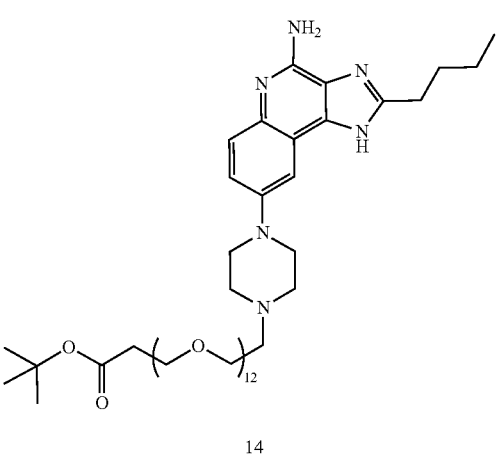

14

2-butyl-8-(piperazin-1-yl)-1H-imidazo[4,5-c]quinolin-4-amine was converted into tert-butyl 1-(4-(4-amino-2-butyl-1H-imidazo[4,5-c]quinolin-8-yl)piperazin-1-yl)-3,6,9,12,15,18,21,24,27,30,33,36-dodecaoxanonatriacontan-39-oate according to the procedure described in Example 7. LC/MS [M+H] 981.61 (calculated); LC/MS [M+H] 981.86 (observed).

Example 14: Synthesis of Compound 15

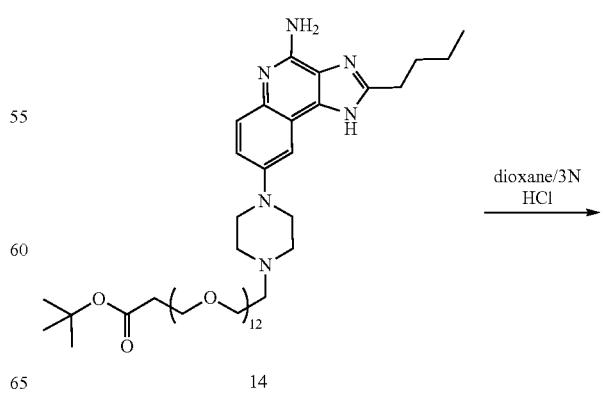

14

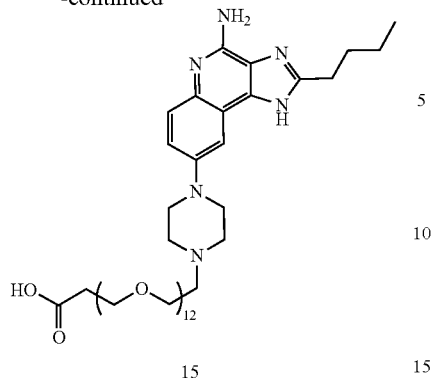

Tert-butyl 1-(4-(4-amino-2-butyl-1H-imidazo[4,5-c]qui-nolin-8-yl)piperazin-1-yl)-3,6,9,12,15,18,21,24,27,30,33,36-dodecaoxanonatriacontan-39-oate was converted into 1-(4-(4-amino-2-butyl-1H-imidazo[4,5-c]quinolin-8-yl)piperazin-1-yl)-3,6,9,12,15,18,21,24,27,30,33,36-dodecaoxanonatriacontan-39-oic acid according to the procedure described in Example 8. Compound was used without further purification.

Example 15: Synthesis of Compound 16

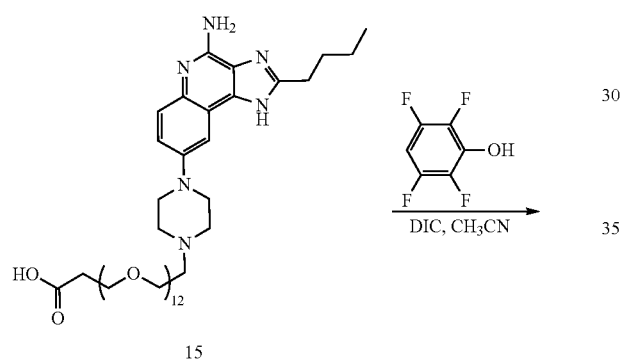

1-(4-(4-amino-2-butyl-1H-imidazo[4,5-c]quinolin-8-yl)piperazin-1-yl)-3,6,9,12,15,18,21,24,27,30,33,36-dodecaoxanonatriacontan-39-oic acid was converted into 2,3,5,6-tetrafluorophenyl 1-(4-(4-amino-2-butyl-1H-imidazo[4,5-c]quinolin-8-yl)piperazin-1-yl)-3,6,9,12,15,18,21,24,27,30,33,36-dodecaoxanonatriacontan-39-oate according to the procedure described in Example 9. LC/MS [M+H] 1073.54 (calculated); LC/MS [M+H] 1073.81 (observed).

Example 16: Synthesis of Immunoconjugate A

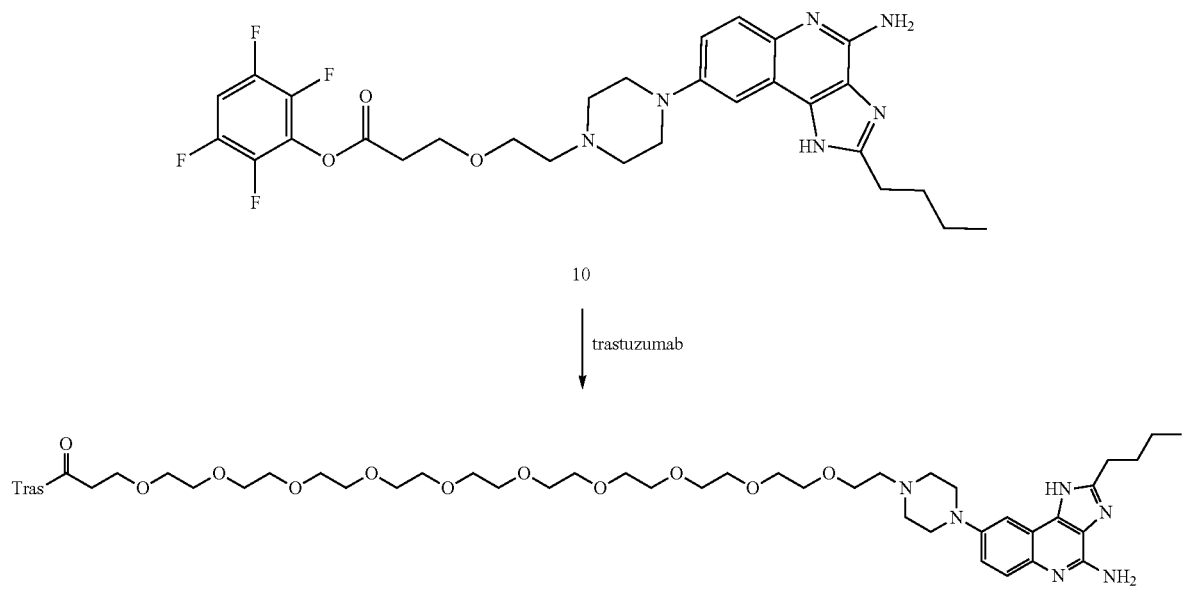

Immunoconjugate A

This example demonstrates the synthesis of Immunoconjugate A with trastuzumab as the antibody construct (Tras).

Trastuzumab was buffer exchanged into the conjugation buffer containing 100 mM boric acid, 50 mM sodium chloride, 1 mM ethylenediaminetetraacetic acid at pH 8.3, using G-25 SEPHADEX™ desalting columns (Sigma-Aldrich, St. Louis, Mo.). The eluates were then each adjusted to 6 mg/ml using the buffer and sterile filtered. Trastuzumab at 6 mg/ml was pre-warmed to 30° C. and rapidly mixed with 7 molar equivalents of Compound 10. The reaction was allowed to proceed for 16 hours at 30° C. and Immunoconjugate A was separated from reactants by running over two successive G-25 desalting columns equilibrated in phosphate buffered saline at pH 7.2. Adjuvant-antibody ratios (DAR) was determined by liquid chromatography mass spectrometry analysis using a C4 reverse phase column on an ACQUITY™ UPLC H-class (Waters Corporation, Milford, Mass.) connected to a XEVO™ G2-XS TOF mass spectrometer (Waters Corporation). Immunoconjugate A had a DAR of 2.5.

Example 17: Synthesis of Immunoconjugate B

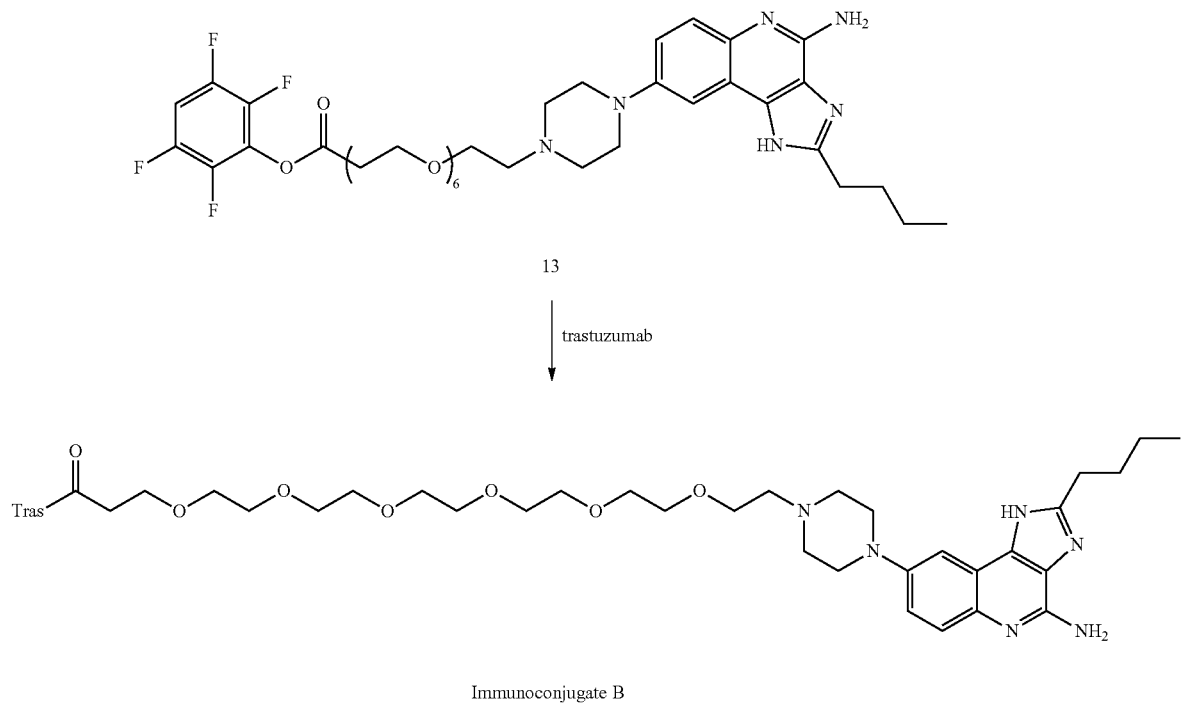

Immunoconjugate B

This example demonstrates the synthesis of Immunoconjugate B with trastuzumab as the antibody construct (Tras).

Trastuzumab was buffer exchanged into the conjugation buffer containing 100 mM boric acid, 50 mM sodium chloride, 1 mM ethylenediaminetetraacetic acid at pH 8.3, using G-25 SEPHADEX™ desalting columns (Sigma-Aldrich). The eluates were then each adjusted to 6 mg/ml using the buffer and sterile filtered. Trastuzumab at 6 mg/ml was pre-warmed to 30° C. and rapidly mixed with 8.5 molar equivalents of Compound 13. The reaction was allowed to proceed for 16 hours at 30° C. and Immunoconjugate B was separated from reactants by running over two successive G-25 SEPHADEX™ desalting columns (Sigma-Aldrich) equilibrated in phosphate buffered saline at pH 7.2. Adjuvant-antibody ratios (DAR) was determined by liquid chromatography mass spectrometry analysis using a C4 reverse phase column on an ACQUITY™ UPLC H-class (Waters Corporation, Milford, Mass.) connected to a XEVO™ G2-XS TOF mass spectrometer (Waters Corporation). Immunoconjugate B had a DAR of 2.37.

Example 18: Synthesis of Immunoconjugate C

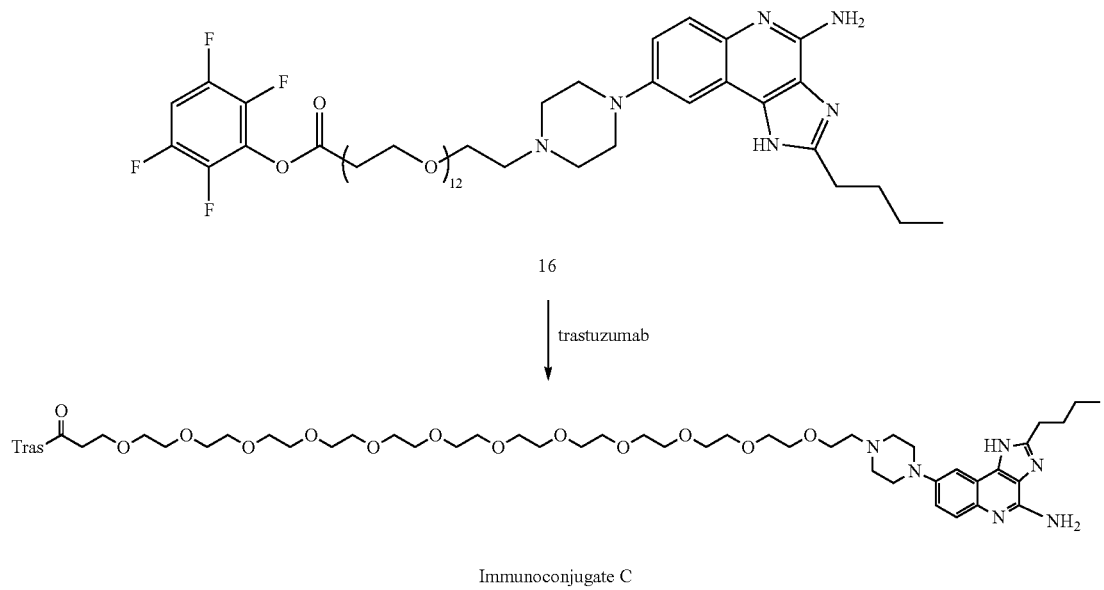

Immunoconjugate C

This example demonstrates the synthesis of Immunoconjugate C with trastuzumab as the antibody construct (Tras).

Trastuzumab was buffer exchanged into the conjugation buffer containing 100 mM boric acid, 50 mM sodium chloride, 1 mM ethylenediaminetetraacetic acid at pH 8.3, using G-25 SEPHADEX™ desalting columns (Sigma-Aldrich). The eluates were then each adjusted to 6 mg/ml using the buffer and sterile filtered. Trastuzumab at 6 mg/nil was pre-warmed to 30° C. and rapidly mixed with 6 molar equivalents of Compound 16. The reaction was allowed to proceed for 16 hours at 30° C. and Immunoconjugate C was separated from reactants by running over two successive G-25 desalting columns equilibrated in phosphate buffered saline at pH 7.2. Adjuvant-antibody ratios (DAR) was determined by liquid chromatography mass spectrometry analysis using a C4 reverse phase column on an ACQUITY™ UPLC H-class (Waters Corporation, Milford, Mass.) connected to a XEVO™ G-2-XS TOF mass spectrometer (Waters Corporation). Immunoconjugate C had a DAR of 2.15.

Example 19. Assessment of Immunoconjugate Activity In Vitro

This example shows that Immunoconjugate A, Immunoconjugate B, and Immunoconjugate C are effective at eliciting myeloid activation, and therefore are useful for the treatment of cancer.

Isolation of Human Antigen Presenting Cells. Human myeloid antigen presenting cells (APCs) were negatively selected from human peripheral blood obtained from healthy blood donors (Stanford Blood Center, Palo Alto, Calif.) by density gradient centrifugation using a ROSETTESEP™ Human Monocyte Enrichment Cocktail (Stem Cell Technologies, Vancouver, Canada) containing monoclonal antibodies against CD14, CD16, CD40, CD86, CD123, and HLA-DR. Immature APCs were subsequently purified to >97% purity via negative selection using an EASYSEP™ Human Monocyte Enrichment Kit (Stem Cell Technologies) without CD16 depletion containing monoclonal antibodies against CD14, CD16, CD40, CD86, CD123, and HLA-DR.

Preparation of Tumor Cells. Three tumor cell lines were used: HCC1954, JIMT-1, and COLO 205. HCC1954 (American Type Culture Collection (ATCC), Manassas, Va.) was derived from a primary stage IIA, grade 3 invasive ductal carcinoma with no lymph node metastases. HCC1954 is positive for the epithelial cell specific marker Epithelial Glycoprotein 2 and for cytokeratin 19, and is negative for expression of estrogen receptor (ER) and progesterone receptor (PR). HCC1954 overexpresses HER2 (as determined by enzyme-linked immunosorbent assay (ELISA)). JIMT-1 (DSMZ, Braunschweig, Germany) was derived from the pleural effusion of a woman with ductal breast cancer (grade 3 invasive, stage IIB) following postoperative radiation. JIMT-1 overexpresses HER2 at what is considered to be a "medium" level of overexpression, but is insensitive to HER2-inhibiting drugs (e.g. trastuzumab). COLO 205 (ATCC) was derived from the ascites fluid of man with carcinoma of the colon. COLO 205 expresses carcinoembryonic antigen (CEA), keratin, interleukin 10 (IL-10), and is considered to overexpress HER2 at relatively "low" level of overexpression.

Tumor cells from each cell line were separately resuspended in PBS with 0.1% fetal bovine serum (FBS) at 1 to $10 \times 10^6$ cells/mL. Cells were subsequently incubated with 2 µM carboxyfluorescein succinimidyl ester (CF SE) to yield a final concentration of 1 µM. The reaction was quenched after 2 minutes via the addition of 10 mL complete medium with 10% FBS and washed twice with complete medium. Cells were either fixed in 2% paraformaldehyde and washed three times with PBS or left viable prior to use.

APC-Tumor Co-cultures. $2 \times 10^5$ APCs were incubated with (e.g., FIG. 1A-1I) or without (e.g., FIG. 2A-3D) CFSE-labeled tumor cells between a 5:1 and 10:1 effector to target (tumor) cell ratio in 96-well plates (Corning, Corning, N.Y.) containing iscove's modified dulbecco's medium (IMDM) (Thermo Fisher Scientific, Waltham, Mass.) supplemented with 10% FBS, 100 U/mL penicillin, 100 µg/mL streptomycin, 2 mM L-glutamine, sodium pyruvate, non-essential amino acids, and, where indicated, various concentrations of unconjugated HER2 antibody, Immunoconjugate A, Immunoconjugate B, and Immunoconjugate C of the invention (as prepared according to the examples above). Cells and cell-free supernatants were analyzed after 18 hours via flow cytometry or ELISA.

Figure 1B:
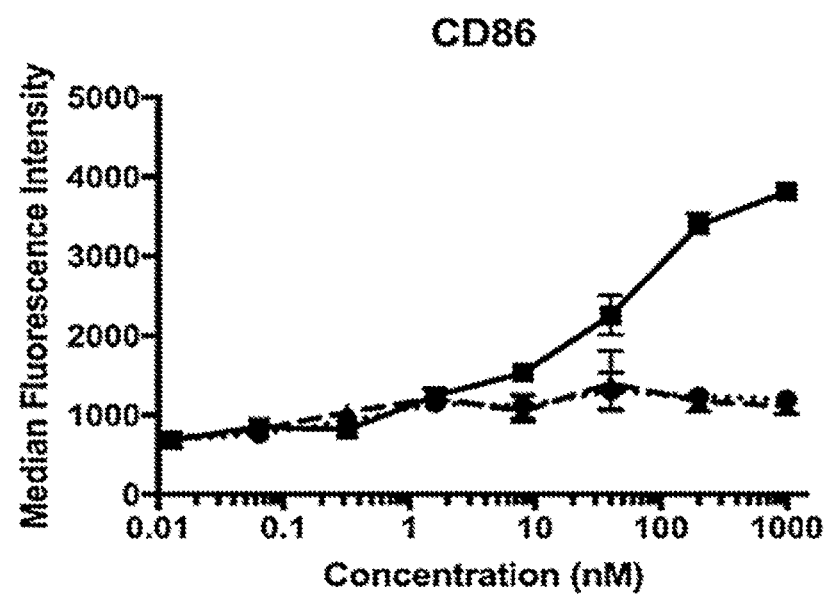
FIG. 1B shows the effect of Immunoconjugate A on myeloid activation in myeloid APC-tumor co-cultures, using the HCC1954 human ductal carcinoma tumor cell line. Median fluorescence intensity of co-stimulatory molecule CD86 (cells gated on viable CD45+CD11c+HLA-DR+) was measured by flow cytometry and is shown for trastuzumab (dotted line, circle), trastuzumab+Compound 7 (dashed line, triangle) or Immunoconjugate A (solid line, square).
Figure 1C:
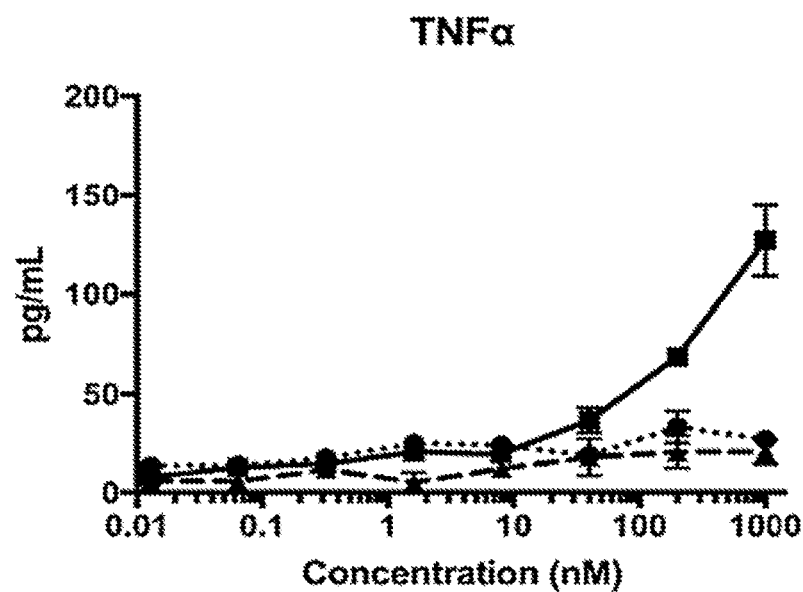
FIG. 1C shows the effect of Immunoconjugate A on myeloid activation in myeloid APC-tumor co-cultures, using the HCC1954 human ductal carcinoma tumor cell. TNFα secretion was measured by cytokine bead array (cells gated on viable CD45+CD11c+HLA-DR+) for trastuzumab (dotted line, circle), trastuzumab+Compound 7 (dashed line, triangle) or Immunoconjugate A (solid line, square).
Figure 1D:
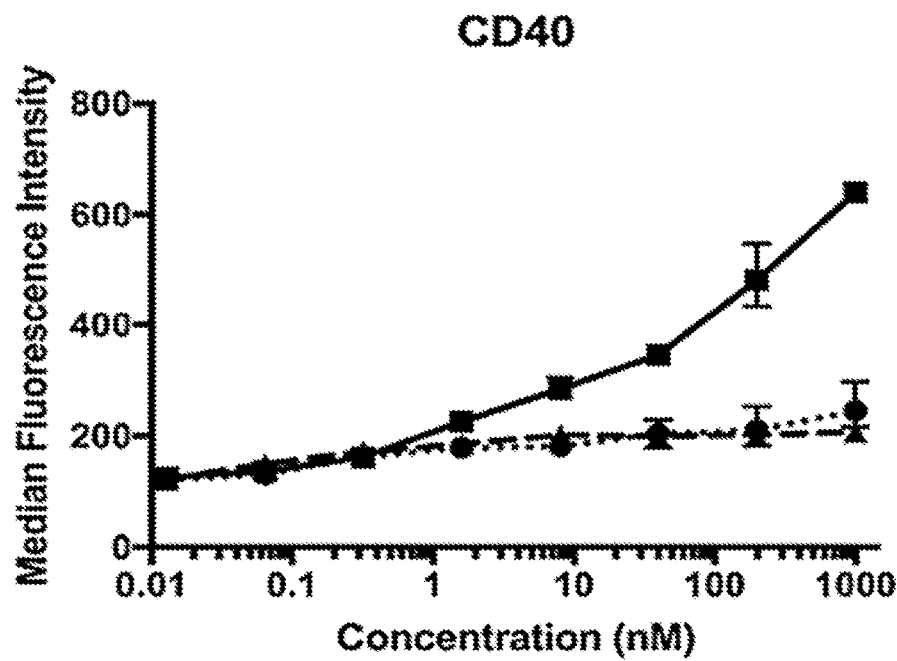
FIG. 1D shows the effect of Immunoconjugate A on myeloid activation in myeloid APC-tumor co-cultures, using the JIMT-1 human ductal carcinoma tumor cell line. Median fluorescence intensity of co-stimulatory molecule CD40 (cells gated on viable CD45+CD11c+HLA-DR+) was measured by flow cytometry and is shown for trastuzumab (dotted line, circle), trastuzumab+Compound 7 (dashed line, triangle) or Immunoconjugate A (solid line, square).
Figure 1E:
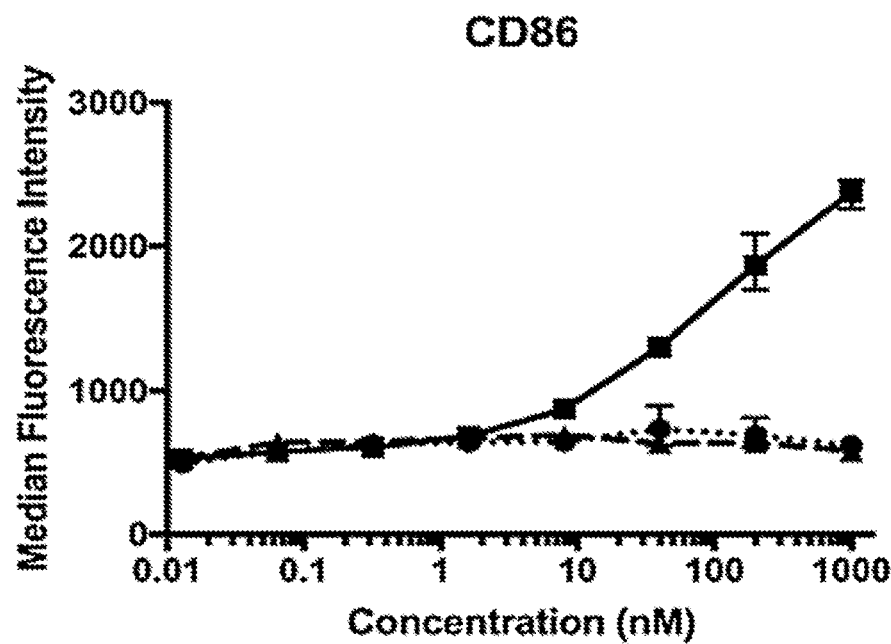
FIG. 1E shows the effect of Immunoconjugate A on myeloid activation in myeloid APC-tumor co-cultures, using the JIMT-1 human ductal carcinoma tumor cell line. Median fluorescence intensity of co-stimulatory molecule CD86 (cells gated on viable CD45+CD11c+HLA-DR+) was measured by flow cytometry and is shown for trastuzumab (dotted line, circle), trastuzumab+Compound 7 (dashed line, triangle) or Immunoconjugate A (solid line, square).
Figure 1F:
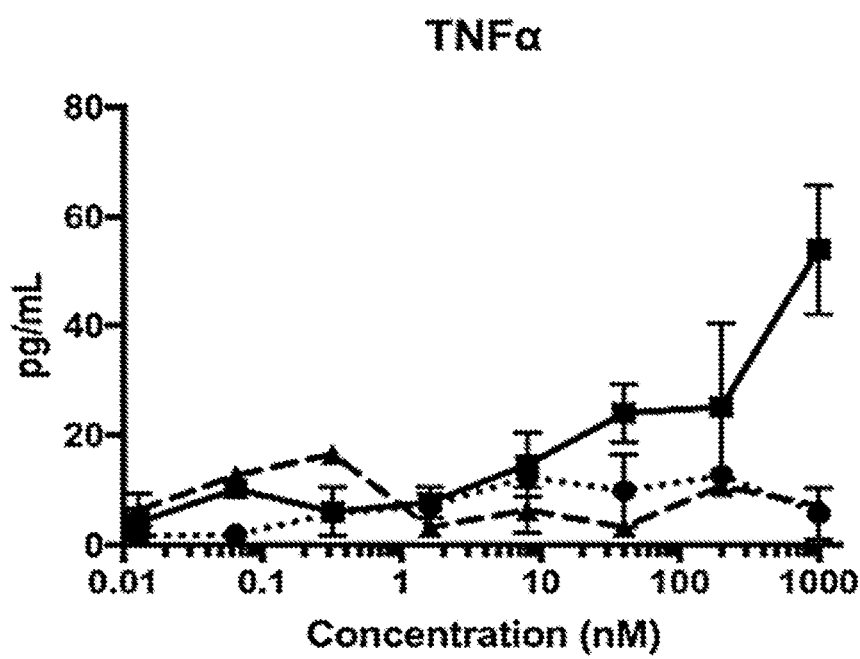
FIG. 1F shows the effect of Immunoconjugate A on myeloid activation in myeloid APC-tumor co-cultures, using the JIMT-1 human ductal carcinoma tumor cell. TNFα secretion was measured by cytokine bead array (cells gated on viable CD45+CD11c+HLA-DR+) for trastuzumab (dotted line, circle), trastuzumab+Compound 7 (dashed line, triangle) or Immunoconjugate A (solid line, square).
Figure 1G:
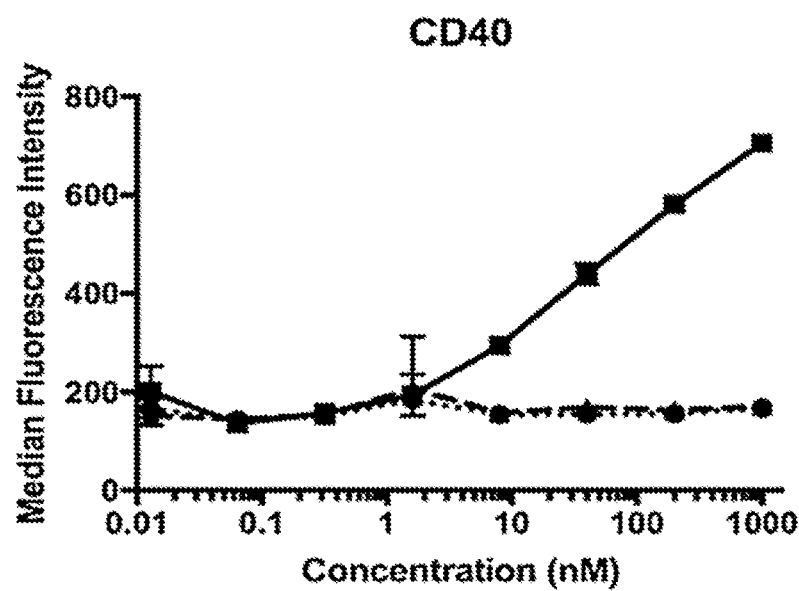
FIG. 1G shows the effect of Immunoconjugate A on myeloid activation in myeloid APC-tumor co-cultures, using the COLO 205 human colon adenocarcinoma cell line. Median fluorescence intensity of co-stimulatory molecule CD40 (cells gated on viable CD45+CD11c+HLA-DR+) was measured by flow cytometry and is shown for trastuzumab (dotted line, circle), trastuzumab+Compound 7 (dashed line, triangle) or Immunoconjugate A (solid line, square).
Figure 1H:
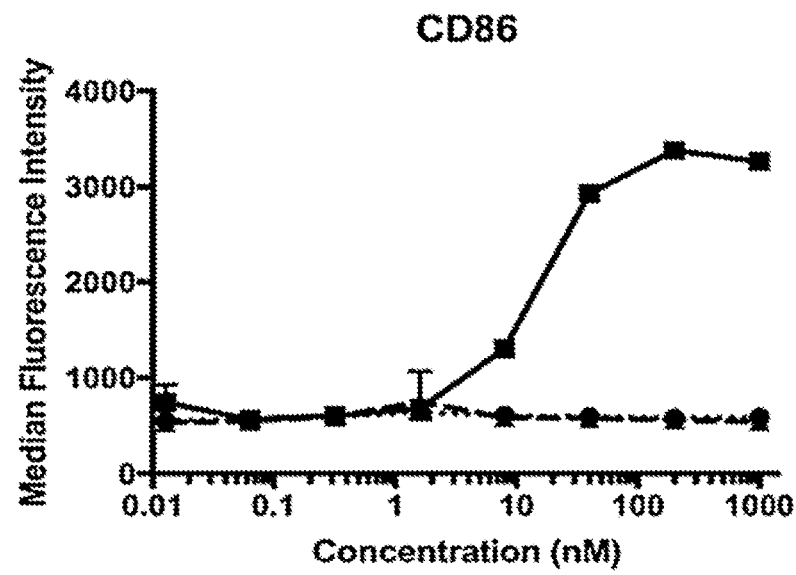
FIG. 1H shows the effect of Immunoconjugate A on myeloid activation in myeloid APC-tumor co-cultures, using the COLO 205 human colon adenocarcinoma cell line. Median fluorescence intensity of co-stimulatory molecule CD86 (cells gated on viable CD45+CD11c+HLA-DR+) was measured by flow cytometry and is shown for trastuzumab (dotted line, circle), trastuzumab+Compound 7 (dashed line, triangle) or Immunoconjugate A (solid line, square).
Figure 1I:
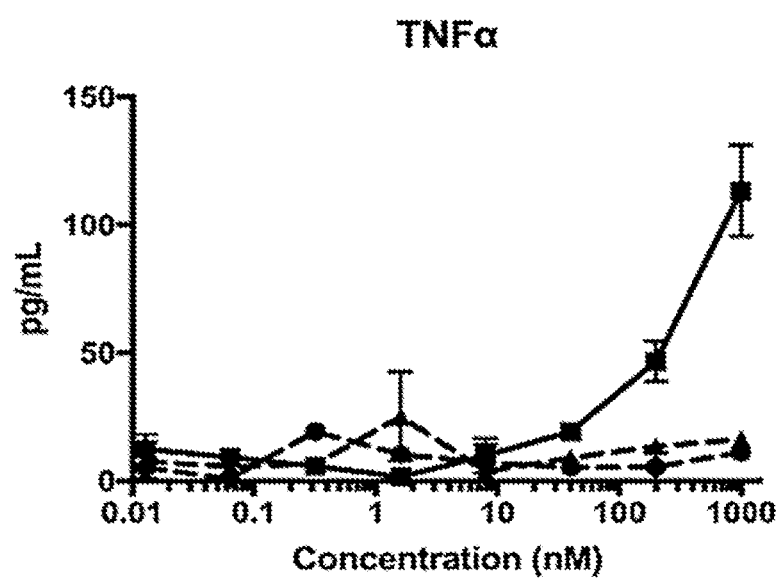
FIG. 1I shows the effect of Immunoconjugate A on myeloid activation in myeloid APC-tumor co-cultures, using the COLO 205 human colon adenocarcinoma cell line. TNFα secretion was measured by cytokine bead array (cells gated on viable CD45+CD11c+HLA-DR+) for trastuzumab (dotted line, circle), trastuzumab+Compound 7 (dashed line, triangle) or Immunoconjugate A (solid line, square).

The results of this assay are shown in the figures, for example, FIG. 1A (CD40) and FIG. 1B (CD86) for Immunoconjugate A on the HCC1954 cell line, FIG. 1D (CD40) and FIG. 1E (CD86) for Immunoconjugate A on the JIMT-1 cell line, and FIG. 1G (CD40) and FIG. 1H (CD86) for Immunoconjugate A on the COLO 205 cell line.

Figure 2A:
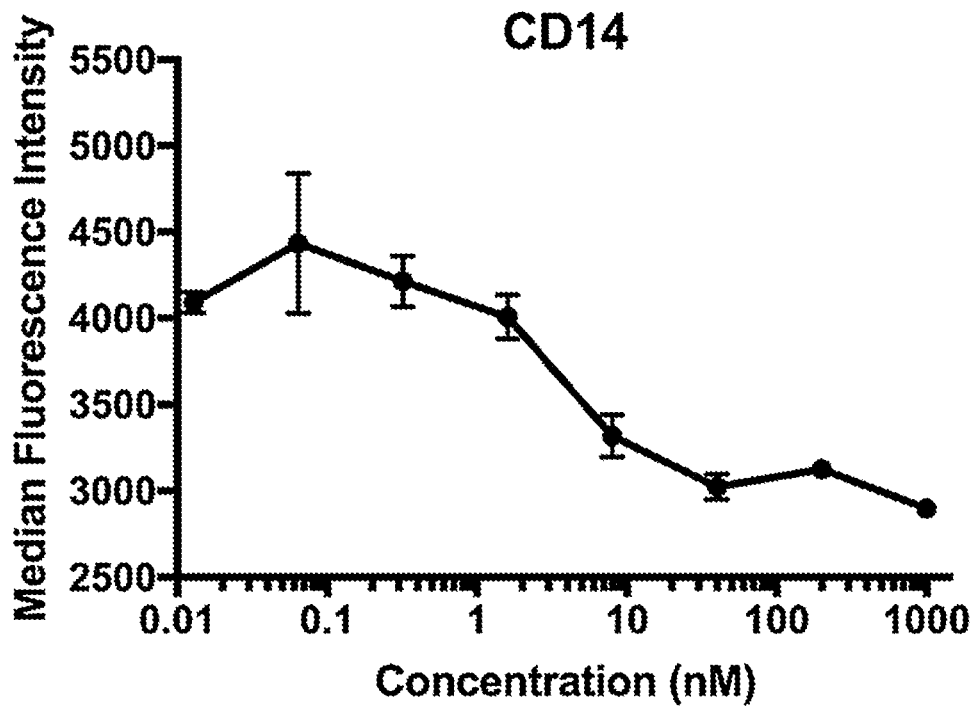
FIG. 2A shows that Immunoconjugate B elicits myeloid differentiation as indicated by CD14 downregulation.
Figure 2B:
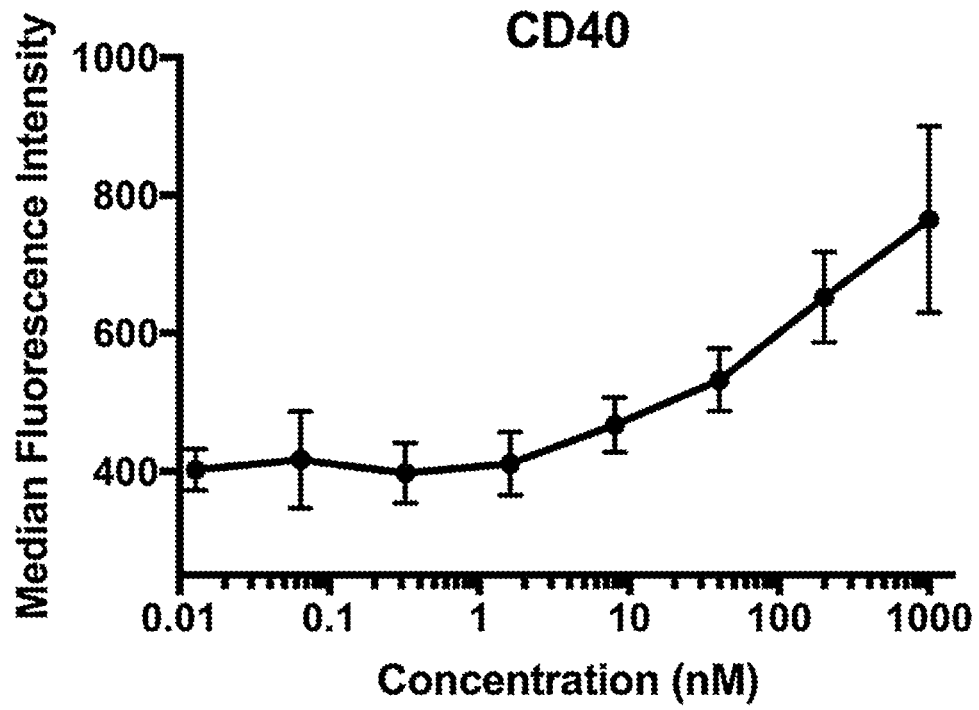
FIG. 2B shows that Immunoconjugate B elicits myeloid activation as indicated by CD40 upregulation.
Figure 2C:
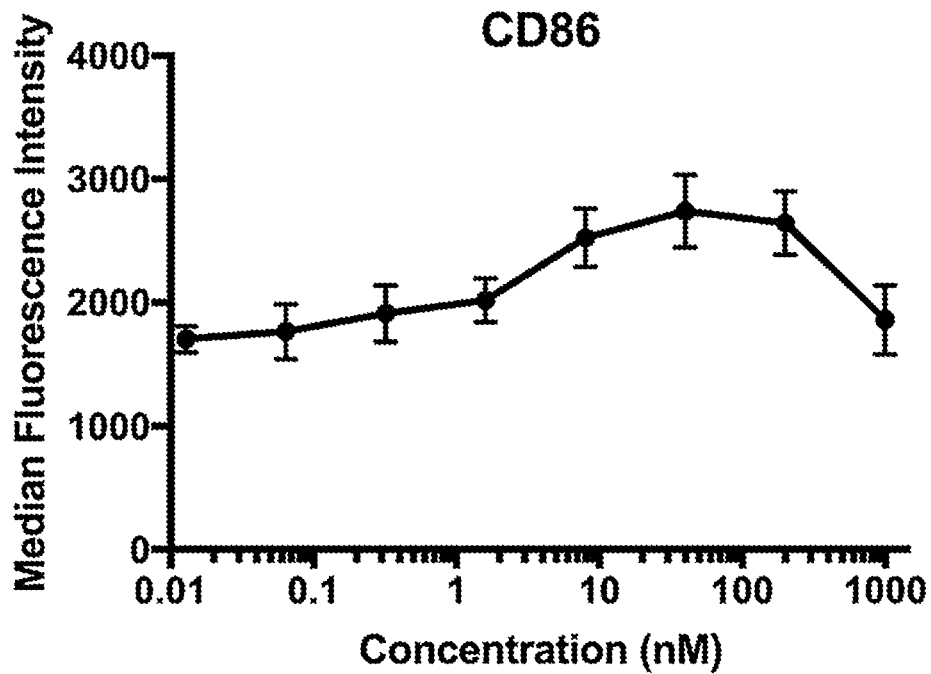
FIG. 2C shows that Immunoconjugate B elicits myeloid activation as indicated by CD86 upregulation.
Figure 3A:
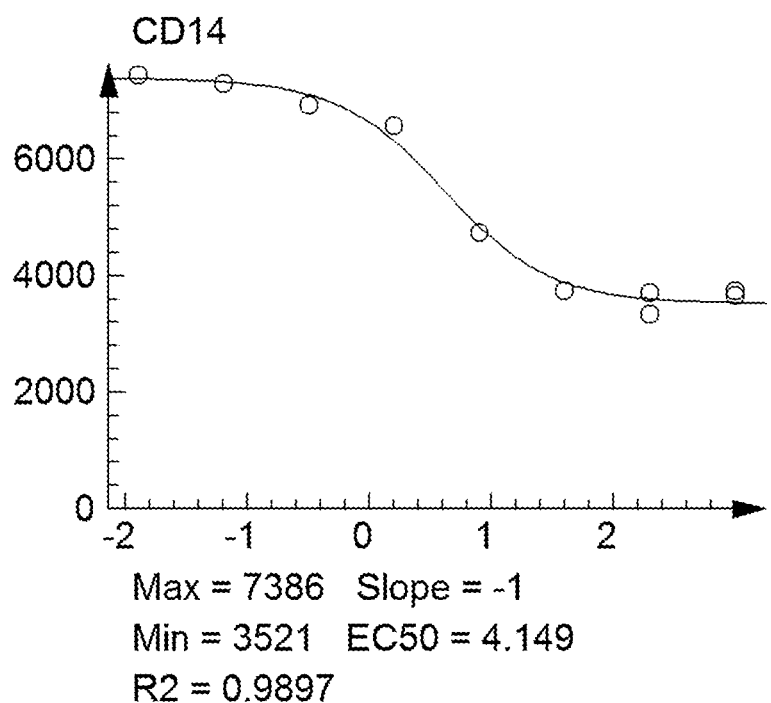
FIG. 3A shows that Immunoconjugate C elicits myeloid differentiation as indicated by CD14 downregulation.
Figure 3B:
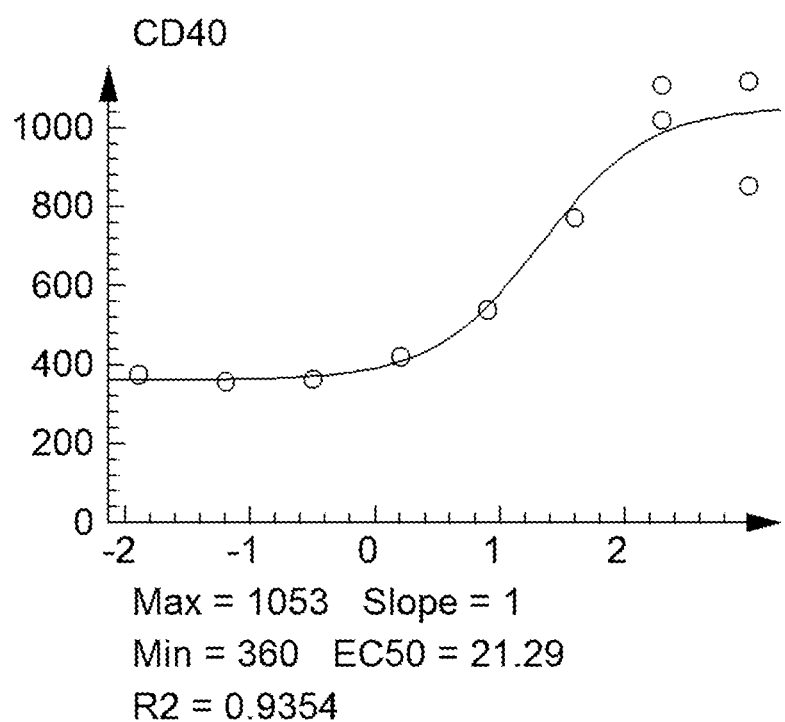
FIG. 3B shows that Immunoconjugate C elicits myeloid activation as indicated by CD40 upregulation.
Figure 3C:
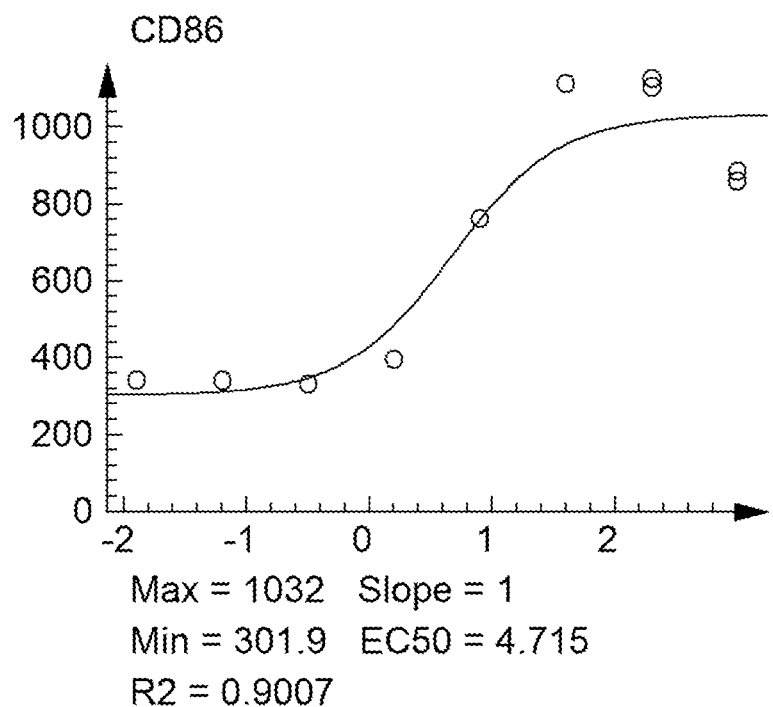
FIG. 3C shows that Immunoconjugate C elicits myeloid activation as indicated by CD86 upregulation.

FIG. 2A shows that Immunoconjugate B elicits myeloid differentiation as indicated by CD14 downregulation. FIG. 2B shows that Immunoconjugate B elicits myeloid activation as indicated by CD40 upregulation. FIG. 2C shows that Immunoconjugate B elicits myeloid activation as indicated by CD86 upregulation. FIG. 3A shows that Immunoconjugate C elicits myeloid differentiation as indicated by CD14 downregulation. FIG. 3B shows that Immunoconjugate C elicits myeloid activation as indicated by CD40 upregulation. FIG. 3C shows that Immunoconjugate C elicits myeloid activation as indicated by CD86 upregulation.

Figure 2D:
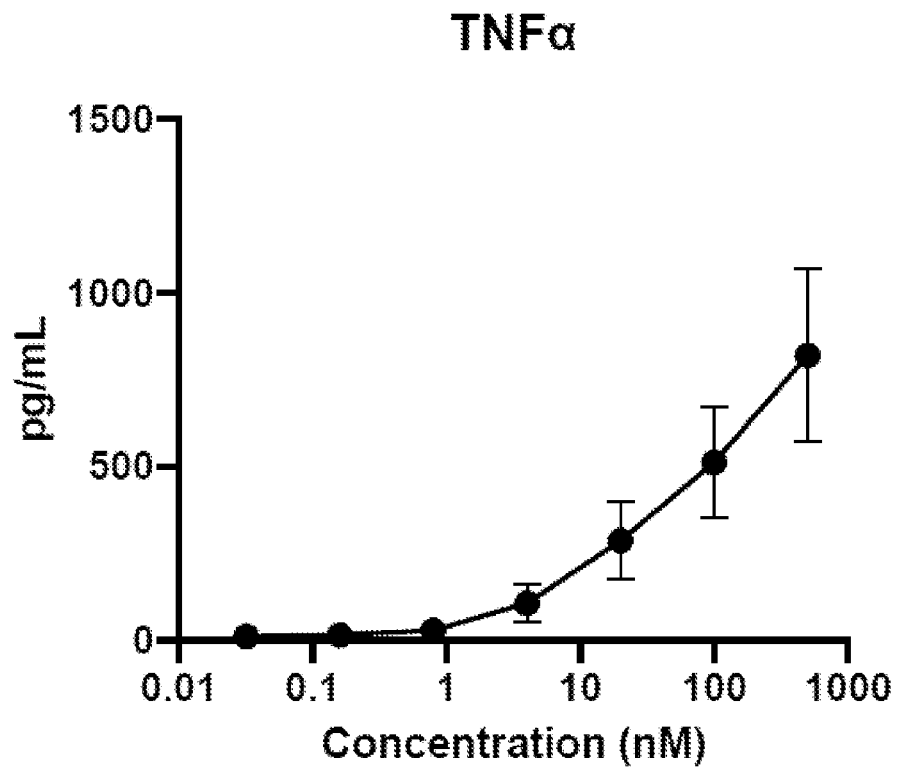
FIG. 2D shows TNFα secretion from myeloid cells following an 18 hour incubation with Immunoconjugate B.
Figure 3D:
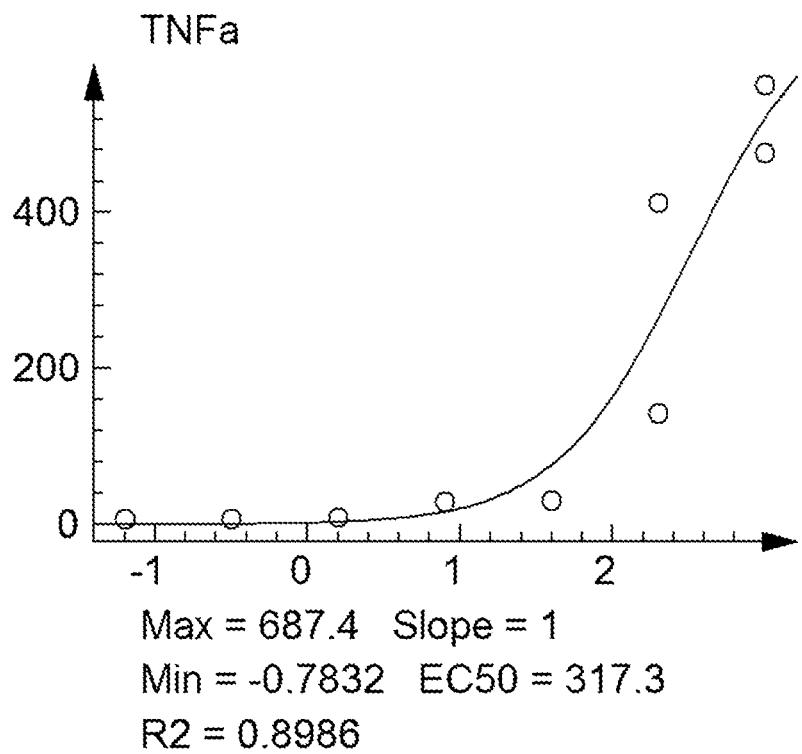
FIG. 3D shows TNFα secretion from myeloid cells following an 18 hour incubation with Immunoconjugate C.

While the expression of T cell stimulatory molecules such as CD40 and CD86 are necessary for effective T cell activation, APCs also influence the nature of the ensuing immune response through the secretion of proinflammatory cytokines. Therefore, the capacity of immunoconjugates to elicit cytokine secretion in human APCs following stimulation was investigated. The data indicate that the immunoconjugate-stimulated cells secreted high levels of TNFα. See FIG. 1C for Immunoconjugate A co-cultured with the HCC1954 cell line, FIG. 1F for Immunoconjugate A co-cultured with the JIMT-1 cell line, and FIG. 1I for Immunoconjugate A co-cultured with the COLO 205 cell line. FIG. 2D shows TNFα secretion from myeloid cells following an 18 hour incubation with Immunoconjugate B. FIG. 3D shows TNFα secretion from myeloid cells following an 18 hour incubation with Immunoconjugate C.

Example 20. Assessment of the Pharmacokinetics (PK) Properties of Immunoconjugate B and Immunoconjugate C This example shows that Immunoconjugate B and Immunoconjugate C have favorable PK properties.

Cynomolgus primates (*Macaca fascicularis*) were dosed with 10 mg/kg of Immunoconjugate B, Immunoconjugate C, Immunoconjugate D, Immunoconjugate E, Immunoconjugate F, or Immunoconjugate G, as shown in Scheme 1, and the PK properties were assessed for 28 days following administration.

Scheme 1.

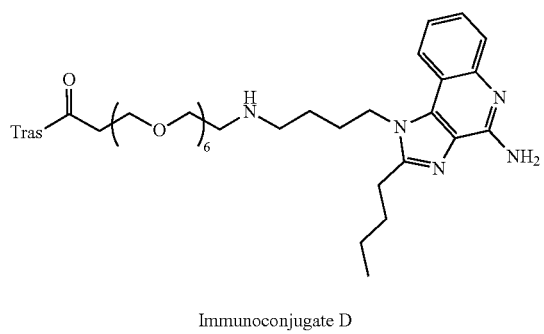

Immunoconjugate D

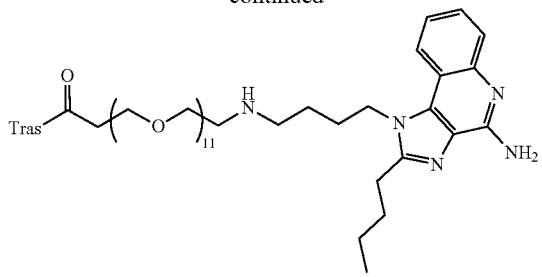

Immunoconjugate E

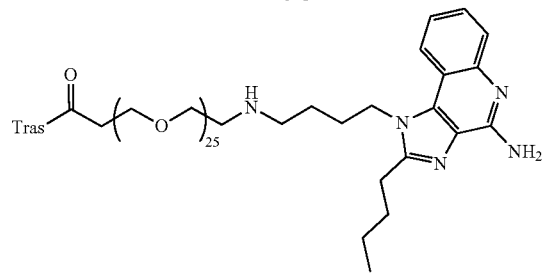

Immunoconjugate F

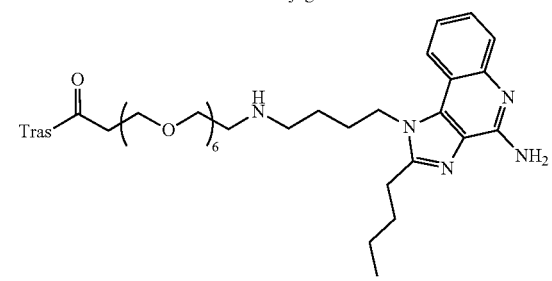

Immunoconjugate G

A trastuzumab PK assay was configured to capture trastuzumab with HCA169 anti-idiotype mAb and to detect with peroxidase labeled HCA176 (HCA176P). An antibody drug conjugate assay was configured to capture trastuzumab with HCA169 anti-idiotype mAb and to detect with a rabbit mAb to A103 followed by detection with peroxidase labeled Goat anti-rabbit IgG. Immunoconjugate B and Immunoconjugate C demonstrated higher serum levels in both PK assays as compared to Immunoconjugate D, Immunoconjugate E, Immunoconjugate, F, and Immunoconjugate G.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An immunoconjugate of formula:

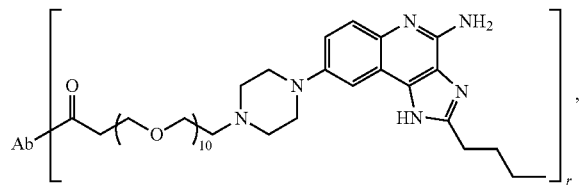

or pharmaceutically acceptable salt thereof, wherein subscript r is an integer from 1 to 10, and "Ab" is trastuzumab.

2. The immunoconjugate of claim 1, or pharmaceutically acceptable salt thereof, wherein subscript r is an integer from 1 to 6.

3. The immunoconjugate of claim 1, or pharmaceutically acceptable salt thereof, wherein subscript r is 1.

4. The immunoconjugate of claim 1, or pharmaceutically acceptable salt thereof, wherein subscript r is 2.

5. The immunoconjugate of claim 1, or pharmaceutically acceptable salt thereof, wherein subscript r is 3.

6. The immunoconjugate of claim 1, or pharmaceutically acceptable salt thereof, wherein subscript r is 4.

7. A method for treating cancer comprising administering a therapeutically effective amount of an immunoconjugate or pharmaceutically acceptable salt thereof according to claim 1 to a subject in need thereof.

8. The method of claim 7, wherein the cancer is a HER2-expressing cancer.

9. The method of claim 7, wherein the cancer is breast cancer.

10. The method of claim 7, wherein the breast cancer is HER2 overexpressing breast cancer.

11. The method of claim 7, wherein the cancer is gastric cancer.

12. The method of claim 7, wherein the gastric cancer is HER2 overexpressing gastric cancer.

13. The method of claim 7, wherein the cancer is gastroesophageal junction adenocarcinoma.

14. The method of claim 7, wherein the cancer is endometrial cancer.

15. The method of claim 7, wherein the cancer is ovarian cancer.

16. The method of claim 7, wherein the cancer is uterine cancer.

17. The method of claim 7, wherein the cancer is bladder cancer.

18. The method of claim 7, wherein the cancer is lung cancer.

19. The method of claim 7, wherein the cancer is head and neck cancer.

20. The method of claim 7, wherein the cancer is liver cancer.

21. The method of claim 7, wherein the cancer is colon cancer.

22. The method of claim 7, wherein the cancer is melanoma.

23. A composition comprising a plurality of immunoconjugates or pharmaceutically acceptable salts thereof according to claim 1 and a pharmaceutically acceptable carrier.

24. The composition of claim 23, wherein

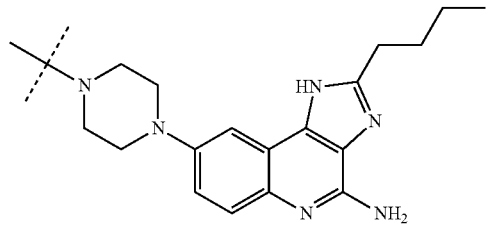

in the immunoconjugate is an adjuvant, and the composition has an average adjuvant to trastuzumab ratio of from about 1 to about 10.

25. The composition of claim 24, wherein the composition has an average adjuvant to trastuzumab ratio of from about 1 to about 4.

26. The composition of claim 24, wherein the composition has an average adjuvant to trastuzumab ratio of from about 1 to about 6.

27. The composition of claim 24, wherein the composition has an average adjuvant to trastuzumab ratio of from about 1 to about 3.

28. The composition of claim 23, wherein the composition further comprises one or more pharmaceutically acceptable excipients.

29. A method for treating cancer comprising administering a therapeutically effective amount of a composition according to claim 23 to a subject in need thereof.

30. The method of claim 29, wherein the cancer is a HER2-expressing cancer.

31. The method of claim 29, wherein the cancer is breast cancer.

32. The method of claim 29, wherein the breast cancer is HER2 overexpressing breast cancer.

33. The method of claim 29, wherein the cancer is gastric cancer.

34. The method of claim 29, wherein the gastric cancer is HER2 overexpressing gastric cancer.

35. The method of claim 29, wherein the cancer is gastroesophageal junction adenocarcinoma.

36. The method of claim 20, wherein the cancer is endometrial cancer.

37. The method of claim 29, wherein the cancer is ovarian cancer.

38. The method of claim 29, wherein the cancer is uterine cancer.

39. The method of claim 29, wherein the cancer is bladder cancer.

40. The method of claim 29, wherein the cancer is lung cancer.

41. The method of claim 29, wherein the cancer is head and neck cancer.

42. The method of claim 29, wherein the cancer is liver cancer.

43. The method of claim 29, wherein the cancer is colon cancer.

44. The method of claim 29, wherein the cancer is melanoma.

* * * * *